United States Patent
Locher et al.

(10) Patent No.: US 9,572,809 B2
(45) Date of Patent: *Feb. 21, 2017

(54) **COMBINATION THERAPY TO TREAT *MYCOBACTERIUM* DISEASES**

(71) Applicant: SPERO TRINEM, INC., Cambridge, MA (US)

(72) Inventors: Christopher Phillip Locher, Lexington, MA (US); Youssef Laafiret Bennani, Lorraine (CA); Anne-Laure Grillot, Milton, MA (US); Hardwin O'Dowd, Boston, MA (US); Emanuele Perola, Brookline, MA (US); Arnaud Le Tiran, Croissy sur Seine (FR); Paul S. Charifson, Framingham, MA (US)

(73) Assignee: SPERO TRINEM, INC., Cambridge, MA (US)

( * ) Notice: Subject to any disclaimer, the term of this patent is extended or adjusted under 35 U.S.C. 154(b) by 480 days.

This patent is subject to a terminal disclaimer.

(21) Appl. No.: 13/942,342

(22) Filed: Jul. 15, 2013

(65) Prior Publication Data

US 2014/0045791 A1  Feb. 13, 2014

Related U.S. Application Data

(60) Provisional application No. 61/673,109, filed on Jul. 18, 2012, provisional application No. 61/782,496, filed on Mar. 14, 2013.

(51) Int. Cl.

| | | |
|---|---|---|
| *A61K 31/34* | (2006.01) | |
| *A61K 31/4168* | (2006.01) | |
| *A61K 31/506* | (2006.01) | |
| *A61K 45/06* | (2006.01) | |
| *A61K 31/132* | (2006.01) | |
| *A61K 31/454* | (2006.01) | |
| *A61K 31/47* | (2006.01) | |
| *A61K 31/496* | (2006.01) | |
| *A61K 31/4965* | (2006.01) | |
| *A61K 31/498* | (2006.01) | |

(Continued)

(52) U.S. Cl.
CPC .......... *A61K 31/506* (2013.01); *A61K 31/132* (2013.01); *A61K 31/34* (2013.01); *A61K 31/4168* (2013.01); *A61K 31/454* (2013.01); *A61K 31/47* (2013.01); *A61K 31/4709* (2013.01); *A61K 31/496* (2013.01); *A61K 31/498* (2013.01); *A61K 31/4965* (2013.01); *A61K 31/5377* (2013.01); *A61K 31/675* (2013.01); *A61K 45/06* (2013.01)

(58) Field of Classification Search
CPC .. A61K 31/685; A61K 31/34; A61K 31/4168; A61K 31/506

See application file for complete search history.

(56) References Cited

U.S. PATENT DOCUMENTS

| | | |
|---|---|---|
| 3,856,957 A | 12/1974 | Seng et al. |
| 4,174,400 A | 11/1979 | Mrozik |

(Continued)

FOREIGN PATENT DOCUMENTS

| | | |
|---|---|---|
| CA | 2739505 | 5/1991 |
| CN | 102276598 | 12/2011 |

(Continued)

OTHER PUBLICATIONS

Beers, M. H., and Berkow, R., "The Merck Manual of Diagnosis and Therapy", 7th Edition, Chapter 156—Bacteremia and Septic Shock, Merck Research Laboratories, Whitehouse Station, NJ pp. 1143-1147 (1999).

Bogatcheva, E. et al., "Discovery of dipiperidines as new antitubercular agents," Bioorganic & Medicinal Chemistry Letters 20 (2010), pp. 201-205.

Bogatcheva, E. et al., "Identification of SQ609 as a lead compound from a library of dipiperidines," Bioorganic & Medicinal Chemistry Letters 21 (2001), pp. 5353-5357.

(Continued)

*Primary Examiner* — Yong Chong
(74) *Attorney, Agent, or Firm* — Cantor Colburn LLP

(57) ABSTRACT

The present invention relates to a compound of formula (I)

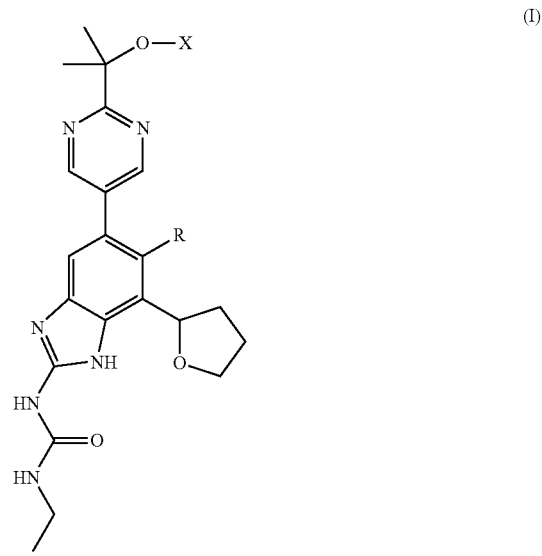

(I)

or a pharmaceutically acceptable salt thereof wherein X and R are as defined herein. The compounds of formula (I) are useful as gyrase and/or topoisomerase IV inhibitors for treating bacterial infections. The compounds of formula (I) either possess a broad range of anti-bacterial activity and advantageous toxicological properties or are prodrugs of compounds having said activity.

28 Claims, 1 Drawing Sheet

(51) Int. Cl.
  *A61K 31/5377* (2006.01)
  *A61K 31/4709* (2006.01)
  *A61K 31/675* (2006.01)

(56) References Cited

U.S. PATENT DOCUMENTS

| | | | |
|---|---|---|---|
| 4,512,998 | A | 4/1985 | Nafissi-Varchei |
| 5,283,248 | A | 2/1994 | Hubschwerlen et al. |
| 5,529,998 | A | 6/1996 | Habich et al. |
| 5,643,935 | A | 7/1997 | Dykstra et al. |
| 5,981,528 | A | 11/1999 | Gravestock |
| 6,069,160 | A | 5/2000 | Stolle et al. |
| 6,268,393 | B1 * | 7/2001 | Xu .................. A61K 31/366 514/453 |
| 6,605,630 | B1 | 8/2003 | Gravestock |
| 6,632,809 | B2 | 10/2003 | Grillot et al. |
| 6,951,961 | B2 | 10/2005 | Protopopova et al. |
| 7,262,212 | B2 | 8/2007 | Tsubouchi et al. |
| RE40,245 | E | 4/2008 | Grillot et al. |
| 7,368,579 | B2 | 5/2008 | Goto et al. |
| 7,414,046 | B2 | 8/2008 | Grillot et al. |
| 7,495,014 | B2 | 2/2009 | Charifson et al. |
| 7,569,591 | B2 | 8/2009 | Charifson et al. |
| 7,582,641 | B2 | 9/2009 | Charifson et al. |
| 7,618,974 | B2 | 11/2009 | Charifson et al. |
| 7,674,801 | B2 | 3/2010 | Basarab et al. |
| 7,727,992 | B2 | 6/2010 | Charifson et al. |
| 7,977,340 | B2 | 7/2011 | Haydon et al. |
| 8,034,832 | B2 | 10/2011 | Charifson et al. |
| 8,067,606 | B2 | 11/2011 | Charifson et al. |
| 8,188,095 | B2 | 5/2012 | Charifson et al. |
| 8,193,352 | B2 | 6/2012 | Charifson et al. |
| 8,404,852 | B2 | 3/2013 | Charifson et al. |
| 8,426,426 | B2 | 4/2013 | Charifson et al. |
| 8,471,014 | B2 | 6/2013 | Shannon et al. |
| 8,476,281 | B2 | 7/2013 | Shannon et al. |
| 8,481,551 | B2 | 7/2013 | Le Tiran et al. |
| 8,481,552 | B2 | 7/2013 | Shannon et al. |
| 2003/0119868 | A1 | 6/2003 | Grillot et al. |
| 2004/0043989 | A1 | 3/2004 | Grillot et al. |
| 2004/0235886 | A1 | 11/2004 | Charifson et al. |
| 2005/0038247 | A1 | 2/2005 | Charifson et al. |
| 2005/0256136 | A1 | 11/2005 | Charifson et al. |
| 2006/0025424 | A1 | 2/2006 | Charifson et al. |
| 2006/0122196 | A9 | 6/2006 | Charifson et al. |
| 2008/0132546 | A1 | 6/2008 | Basarab et al. |
| 2009/0176771 | A1 | 7/2009 | Charifson et al. |
| 2009/0197877 | A1 | 8/2009 | Haydon et al. |
| 2009/0325935 | A1 | 12/2009 | Charifson et al. |
| 2009/0325955 | A1 | 12/2009 | Charifson et al. |
| 2010/0063069 | A1 | 3/2010 | Charifson et al. |
| 2010/0105701 | A1 | 4/2010 | Charifson et al. |
| 2010/0234410 | A1 | 9/2010 | Ono et al. |
| 2010/0311766 | A1 | 12/2010 | Haydon et al. |
| 2011/0104207 | A1 | 5/2011 | Charifson et al. |
| 2011/0166088 | A1 | 7/2011 | Sattigeri et al. |
| 2011/0263590 | A1 | 10/2011 | Haydon et al. |
| 2012/0004221 | A1 | 1/2012 | Haydon et al. |
| 2012/0010222 | A1 | 1/2012 | Charifson et al. |
| 2012/0114601 | A1 | 5/2012 | Bradbury et al. |
| 2012/0184512 | A1 | 7/2012 | Le Tiran et al. |
| 2012/0184564 | A1 | 7/2012 | Shannon et al. |
| 2012/0184741 | A1 | 7/2012 | Shannon et al. |
| 2012/0184742 | A1 | 7/2012 | Shannon et al. |
| 2013/0157979 | A1 | 6/2013 | Bennani et al. |
| 2013/0261305 | A1 | 10/2013 | Shannon et al. |
| 2013/0267540 | A1 | 10/2013 | Shannon et al. |
| 2013/0289002 | A1 | 10/2013 | Le Tiran et al. |
| 2013/0317222 | A1 | 11/2013 | Shannon et al. |
| 2014/0031318 | A1 | 1/2014 | O'Dowd et al. |
| 2014/0045791 | A1 | 2/2014 | Locher et al. |

FOREIGN PATENT DOCUMENTS

| | | |
|---|---|---|
| EP | 0433648 | 6/1991 |
| EP | 0738726 | 10/1996 |
| EP | 1055668 | 11/2000 |
| EP | 2468746 | 6/2012 |
| JP | 2005330266 | 12/2005 |
| WO | WO 99/35155 | 7/1999 |
| WO | WO 00/49015 | 8/2000 |
| WO | WO 00/71522 | 11/2000 |
| WO | WO 01/40236 | 6/2001 |
| WO | WO 02/060879 | 8/2002 |
| WO | WO 03/096987 | 11/2003 |
| WO | WO 03/105846 | 12/2003 |
| WO | WO 2004/011436 | 2/2004 |
| WO | WO 2004/033463 | 4/2004 |
| WO | WO 2004/035547 | 4/2004 |
| WO | WO 2005/012292 | 10/2005 |
| WO | WO 2006/022773 | 3/2006 |
| WO | WO 2006/125769 | 11/2006 |
| WO | WO 2007/056330 | 5/2007 |
| WO | WO 2007/111023 | 10/2007 |
| WO | WO 2007/148093 | 12/2007 |
| WO | WO 2008/020560 | 2/2008 |
| WO | WO 2008/068470 | 6/2008 |
| WO | WO 2009/074810 | 6/2009 |
| WO | WO 2009/074812 | 6/2009 |
| WO | WO 2009/156966 | 12/2009 |
| WO | WO 2010/038874 | 4/2010 |
| WO | WO 2011/032050 | 3/2011 |
| WO | WO 2011/047323 | 4/2011 |
| WO | WO 2012/045124 | 4/2012 |
| WO | WO 2012/097269 | 7/2012 |
| WO | WO 2012/097270 | 7/2012 |
| WO | WO 2012/097273 | 7/2012 |
| WO | WO 2012/177707 | 12/2012 |
| WO | WO 2013/138860 | 9/2013 |

OTHER PUBLICATIONS

Champoux, J.J., Annu. Rev. Biochem., 2001, 70, pp. 369-413.
Charifson et al., J. Med. Chem., 2008, 51, pp. 5243-5263.
Charles W. Stratton, MD. "In Vitro Susceptibility Testing Versus in Vivo-Effectiveness" The Medical Clinics of North America 2006, 90, pp. 1077-1088.
Cho, S. H. et al., "Low-Oxygen-Recovery Assay for High-Throughput Screening of Compounds against Nonreplicating *Mycobacterium tuberculosis*," Antimicrobial Agents and Chemotherapy, Apr. 2007, vol. 51, No. 4, pp. 1380-1385.
Drlica and Zhao, Microbiology and Molecular Biology Reviews, 1997, 61, pp. 377-392.
Drlica, Molecular Microbiology, 1992, 6, 425.
Eckert et al., "The antifungal activity of . . . " CA 93:39290 (1980).
Ejim, L., et al., "Combinations of antibiotics and nonantibiotic drugs enhance antimicrobial efficacy," Nature Chemical Biology, Jun. 2011, 7(6), pp. 348-350.
Fridman et al. "Chemoenzymatic Formation of Novel Aminocoumarin Antibiotics by the Enzymes CouN1 and CouN7," Biochemistry 2007, 46, pp. 8462-8471.
Gershman in The Medical Reporter, 1997.
Gumbo, T., et al., "Selection of a Moxifloxacin Dose That Suppresses Drug Resistance in *Mycobacterium tuberculosis*, by Use of an In Vitro Pharmacodynamic Infection Model and Mathematical Modeling," Journal of Infectious Diseases, 2004, 190, pp. 1642-1651.
Guven et al. "Synthesis and Antimicrobial Activity of Some Novel Furyl and Benzimidazole Substituted Benzyl Ethers" Journal of Heterocyclic Chemistry 2007, 44, 731.
He et al. "Synthesis and biological evaluation of novel benzimidazoles as potential antibacterial agents." Bioorganic & Medicinal Chemistry Letters 2004, 14, pp. 1217-1220.
Hubschwerlen et al., "Pyrimido[1,6-1]benzimidazoles: A New Class of DNA Gyrase Inhibitors" J. Med. Chem, vol. 35, No. 8, pp. 1385-1392, 1992.

(56) References Cited

OTHER PUBLICATIONS

International Search Report and Written Opinion of the International Searching Authority, International Patent Application No. PCT/US2012/021270 (Mar. 16, 2012).
International Search Report and Written Opinion of the International Searching Authority, International Patent Application No. PCT/US2012/021281 (May 3, 2012).
International Search Report and Written Opinion of the International Searching Authority, International Patent Application No. PCT/US2012/021280 (Mar. 23, 2012).
International Search Report and Written Opinion of the International Searching Authority, International Patent Application No. PCT/US2012/021275 (Mar. 23, 2012).
International Search Report and Written Opinion of the International Searching Authority, International Patent Application No. PCT/US2012/043266 (Aug. 28, 2012).
International Search Report and Written Opinion of the International Searching Authority, International Patent Application No. PCT/US2012/051008 (Oct. 14, 2013).
International Search Report and Written Opinion of the International Searching Authority, International Patent Application No. PCT/US2012/050564 (Oct. 8, 2013).
Joseph E. Drumm et al., "Facile preparation of fused ring azolylureas," 48 Tetrahedron Lett. pp. 5535-5538 (2007).
Kornberg and Baker, DNA Replication, 2d Ed., Chapter 12, 1992, W. H. Freeman and Co.
Kus, C., "Synthesis and Antimicrobial Activities of 5-fluoro-1, 2, 6-trisubstituted benzimidazole carboxamide and acetamide derivatives," Arch. Pharm. Pharm. Med. Chem. 334(11):361-365 (2001).
Levy, "The Challenge of Antibiotic Resistance", Scientific American, Mar. 1998).
Lewis, "The Rise of Antibiotic-Resistant Infections", FDA Consumer magazine, Sep. 1995.
Li, S.M., et al., "New Aminocoumarin Antibiotics from Genetically Engineered *Streptomyces* Strains," Current Medicinal Chemistry, 2005, 12, 419-427.
Maxwell, Mol. Microbiol., 1993, 9, 681.
Maxwell, Trends in Microbiology, 1997, 5, 102.
MayoClinic "Antibiotic associated diarrhea" Mayoclinic.com. (2007).
MMWR (Morbidity and Mortality Weekly Report). "Treatment of Tuberculosis, American Thoracic Society," 2003, 52, No. RR-11, pp. 1-80, p. 31.
Nicolaus B.J.R., "Symbiotic Approach to Drug Design," Decision Making in Drug Research, pp. 173-186 (1983).
Pea et al., PubMed Abstract (Clin Pharmacokinet. 44(10):1009-34) 2005.
Pucci, M.J. et al., "In Vitro and In Vivo Profiles of ACH-702, an Isothiazoloquinolone, against Bacterial Pathogens," Antimicrobial Agents and Chemotherapy, Jun. 2011, 55, 6, pp. 2860-2871.
Sasaki, H. et al., "Synthesis and Antituberculosis Activity of a Novel Series of Optically Active 6-Nitro-2,3-dihydroimidazo[2,1-b]oxazoles," J. Med. Chem., 2006, 49, pp. 7854-7860.
Singh, S.K., et al., "Studies in antiparastic agents: Part 13—Synthtesis of 4-aryl-2-substitutedamino-thiazoles as potential anthelmintics," Indian J. Chem., 28B (9):786-789 (1989).
Skopenka, V.V., et al., "Organotin Carbamoyldicyanomethanide, nitrosocarbamoylcyanomethanide, and Carbamoylcyanides," retrieved from STN Database accession No. 101:230674, XP002254350 abstract and Dopovidi Akademii Nauk Ukrains'Koi RSR, Seriya B: Geologichni, Khimichni Ta Biologichni Nauki, 7:44-46 (1984).
Snyder et al., PubMed Abstract (J. Med Liban. 48(4):208-14), Jul.-Aug. 2000.
Stephen P. East et al., "DNA gyrase (GyrB)/topoisomerase IV (ParE) inhibitors," 19 Bioorg. Med. Chem. Lett. 894-899 (2009).
Sun et al., "Synthesis and Evaluation of Terbenzimidazoles as Topoisomerase I Inhibitors" J. Med. Chem., vol. 38, No. 18, pp. 3638-3644, 1995.
Tamura, James K. and Gellert, Martin, "Characterization of the ATP Binding Site on *Escherichia coli* DNA Gyrase," The Journal of Biological Chemistry, vol. 265, No. 34, (1990), pp. 21342-21349.
Tanitame et al. "Design, synthesis and structure-activity relationship studies of novel indazole analogues as DNA gyrase inhibitors with Gram-positive antibacterial activity" Bioorganic & Medicinal Chemistry Letters 2004, 14, 2857-2862.
Wallis, R.S., et al., "Pharmacokinetics and Whole-Blood Bactericidal Activity against *Mycobacterium tuberculosis* of Single Dose of PNU-100480 in Healthy Volunteers," The Journal of Infectious Diseases, Sep. 2010, 202(5); pp. 745-751.
Wassenaar "Bacteria; more than pathogens" Am. Ins. Biol. Sci. Internet p. 1-7 (2002).
Webster's Dictionary (1984) p. 933.
WHO Report, "Use of Quinolones in Food Animals and Potential Impact on Human Health", 1998.
Matthew E. Falagas et al., "Colistin: The Revival of Polymyxins for the Management of Multidrug-Resistant Gram-Negative Bacterial Infections," Reviews of Anti-Infective Agents, CID 2005:40 (2005), pp. 1333-1341.
Silke Alt, Lesley A. Mitchenall, Anthony Maxwell, and Lutz Heide, "Inhibition of DNA gyrase and DNA topoisomerase IV of *Staphylococcus aureus* and *Escherichia coli* by aminocoumarin antibiotics," Journal of Antimicrobial Chemotherapy 66; pp. 2061-2069; (2011).
Barton J. Bradbury and Michael J. Pucci, "Recent advances in bacterial topoisomerase inhibitors," Current Opinion in Pharmacology 8, pp. 574-581; (2008).
Chabner, Bruce A. et al., "Antineoplastic Agents," The Pharmacological Basics of Therapeutics 11th edition, Chapter 51; pp. 1315-1403; (2006).
Poupaert, Jacques H., "Drug Design: Basic Principles and Application," Encyclopedia of Pharmaceutical Technology; pp. 1362-1369; (2007).
Akihiko Tanitame et al., "Synthesis and Antibacterial Activity of Novel Series of Potent DNA Gyrase Inhibitors. Pyrazole Derivatives," J. Med. Chem. 47; pp. 3693-3696; (2004).

\* cited by examiner

COMBINATION THERAPY TO TREAT *MYCOBACTERIUM* DISEASES

RELATED APPLICATIONS

This application is a non-provisional filing which claims the benefit of Provisional U.S. Patent Application Ser. No. 61/673,109, filed Jul. 18, 2012 and Provisional U.S. Patent Application Ser. No. 61/782,496, filed Mar. 14, 2013. The entire contents of these patent applications are hereby incorporated herein by reference.

BACKGROUND OF THE INVENTION

*Mycobacterium tuberculosis*, the bacterium which causes tuberculosis (TB), remains a major cause of death in the world in spite of relatively effective treatments with multi-drug combinations due to the lack of treatment accessibility, HIV co-infection, and the lengthy treatment time. Combinations of multiple drugs are required to prevent the emergence of drug resistance and to effectively treat the infection. Drug sensitive TB is treated with isoniazid, rifampicin, pyrazinamide and ethambutol or streptomycin. Importantly, there are many side effects associated with the drugs making compliance difficult and tolerability challenging. For example, isoniazid causes peripheral nervous system disorder and induces serious liver dysfunction in some people when used in combination with rifampicin; rifampicin can cause liver dysfunction or hepatopathy, malaise, drug allergy, and its use with other drugs such as HIV protease inhibitors, is compromised due to P450-associated enzyme induction. In summary, tolerability remains a major challenge for current TB drug treatment regimens.

A revitalized effort to develop new drug treatments and combinations of drugs has been inspired by medical philanthropy and cooperative efforts of public private partnerships. In addition, in spite of the total number of cases of TB having decreased in most countries, the lack of accessibility of treatment of multi-drug resistant (MDR-TB) and extensively drug resistant (XDR-TB) combined with the emergence of extremely drug resistant (XXDR-TB) or totally drug resistant (TDR-TB) raises global concerns about the sustainability of the current control measures. Furthermore, there remain too few combinations that have the potential to shorten the treatment time of drug sensitive and drug resistant TB infection (currently from six months to two years, respectively), which remains critical to treatment compliance and preventing the emergence of drug resistance. Moreover, there is mechanistic and chemical redundancy for compounds currently in clinical development and safety liabilities for most classes of drugs reflecting a lack of bold and innovative approaches. For example, two fluoroquinolones in phase 3 clinical trials do not address the problem of XDR-TB and may exacerbate drug resistance; three oxazolidinones in phase 2 clinical trials have not proven to shorten the time of treatment; and two nitroimidazoles in clinical development may be incompatible with some of the front line treatment drugs. Thus, there remains an overall dearth of drug candidates for the treatment of tuberculosis; see WGND pipeline as reference http://www.newtbdrugs.org/pipeline.php.

As a result of the need to combat drug-resistant bacteria and the increasing failure of the available drugs, there has been a resurgent interest in discovering new antibiotics. One attractive strategy for developing new antibiotics is to inhibit DNA gyrase and/or topoisomerase IV, bacterial enzymes necessary for DNA replication, and therefore, necessary for bacterial cell growth and division. Gyrase and/or topoisomerase IV activity are also associated with events in DNA transcription, repair and recombination. Gyrase is one of the topoisomerases, a group of enzymes which catalyze the interconversion of topological isomers of DNA (see generally, Kornberg and Baker, DNA Replication, 2d Ed., Chapter 12, 1992, W. H. Freeman and Co.; Drlica, Molecular Microbiology, 1992, 6, 425; Drlica and Zhao, Microbiology and Molecular Biology Reviews, 1997, 61, pp. 377-392). Gyrase itself controls DNA supercoiling and relieves topological stress that occurs when the DNA strands of a parental duplex are untwisted during the replication process. Gyrase also catalyzes the conversion of relaxed, closed circular duplex DNA to a negatively superhelical form which is more favorable for recombination. The mechanism of the supercoiling reaction involves the wrapping of gyrase around a region of the DNA, double strand breaking in that region, passing a second region of the DNA through the break, and rejoining the broken strands. Such a cleavage mechanism is characteristic of a type II topoisomerase. The supercoiling reaction is driven by the binding of ATP to gyrase. The ATP is then hydrolyzed during the reaction. This ATP binding and subsequent hydrolysis cause conformational changes in the DNA-bound gyrase that are necessary for its activity. It has also been found that the level of DNA supercoiling (or relaxation) is dependent on the ATP/ADP ratio. In the absence of ATP, gyrase is only capable of relaxing supercoiled DNA.

Bacterial DNA gyrase is a 400 kilodalton protein tetramer consisting of two A (GyrA) and two B subunits (GyrB). Binding and cleavage of the DNA is associated with GyrA, whereas ATP is bound and hydrolyzed by the GyrB protein. GyrB consists of an amino-terminal domain which has the ATPase activity, and a carboxy-terminal domain which interacts with GyrA and DNA. By contrast, eukaryotic type II topoisomerases are homodimers that can relax negative and positive supercoils, but cannot introduce negative supercoils. Ideally, an antibiotic based on the inhibition of bacterial DNA gyrase and/or topoisomerase IV would be selective for these enzymes and be relatively inactive against the eukaryotic type II topoisomerases.

Topoisomerase IV primarily resolves linked chromosome dimers at the conclusion of DNA replication.

The widely-used quinolone antibiotics inhibit bacterial DNA gyrase (GyrA) and/or Topoisomerase IV (ParC). Examples of the quinolones include the early compounds such as nalidixic acid and oxolinic acid, as well as the later, more potent fluoroquinolones such as norfloxacin, ciprofloxacin, and trovafloxacin. These compounds bind to GyrA and/or ParC and stabilize the cleaved complex, thus inhibiting overall gyrase function, leading to cell death. The fluoroquinolones inhibit the catalytic subunits of gyrase (GyrA) and/or Topoisomerase IV (Par C) (see Drlica and Zhao, Microbiology and Molecular Biology Reviews, 1997, 61, 377-392). However, drug resistance has also been recognized as a problem for this class of compounds (WHO Report, "Use of Quinolones in Food Animals and Potential Impact on Human Health", 1998). With the quinolones, as with other classes of antibiotics, bacteria exposed to earlier compounds often quickly develop cross-resistance to more potent compounds in the same class. The associated subunits responsible for supplying the energy necessary for catalytic turnover/resetting of the enzymes via ATP hydrolysis are GyrB (gyrase) and ParE (topoisomerase IV), respectively (see, Champoux, J. J., Annu. Rev. Biochem., 2001, 70, pp. 369-413). Compounds that target these same ATP binding sites in the GyrB and ParE subunits would be useful for treating various bacterial infections (see, Charifson et al., J. Med. Chem., 2008, 51, pp. 5243-5263).

There are fewer known inhibitors that bind to GyrB. Examples include the coumarins, novobiocin and coumermycin A1, cyclothialidine, cinodine, and clerocidin. The coumarins have been shown to bind to GyrB very tightly. For example, novobiocin makes a network of hydrogen bonds with the protein and several hydrophobic contacts. While novobiocin and ATP do appear to bind within the ATP binding site, there is minimal overlap in the bound orientation of the two compounds. The overlapping portions are the sugar unit of novobiocin and the ATP adenine (Maxwell, Trends in Microbiology, 1997, 5, 102).

For coumarin-resistant bacteria, the most prevalent point mutation is at a surface arginine residue that binds to the carbonyl of the coumarin ring (Arg136 in *E. coli* GyrB). While enzymes with this mutation show lower supercoiling and ATPase activity, they are also less sensitive to inhibition by coumarin drugs (Maxwell, Mol. Microbiol. 1993, 9, 681).

Despite being potent inhibitors of gyrase supercoiling, the coumarins have not been widely used as antibiotics. They are generally not suitable due to their low permeability in bacteria, eukaryotic toxicity, and poor water solubility (Maxwell, Trends in Microbiology, 1997, 5, 102). It would be desirable to have a new, effective GyrB and ParE inhibitor that overcomes these drawbacks and, preferably does not rely on binding to Arg136 for activity. Such an inhibitor would be an attractive antibiotic candidate, without a history of resistance problems that plague other classes of antibiotics.

As bacterial resistance to antibiotics has become an important public health problem, there is a continuing need to develop newer and more potent antibiotics. More particularly, there is a need for antibiotics that represent a new class of compounds not previously used to treat bacterial infection. Compounds that target the ATP binding sites in both the GyrB (gyrase) and ParE (topoisomerase IV) subunits would be useful for treating various bacterial infections. Such compounds would be particularly useful in treating nosocomial infections in hospitals where the formation and transmission of resistant bacteria are becoming increasingly prevalent. Furthermore, there is a need for new antibiotics having a broad spectrum of activity with advantageous toxicological properties.

SUMMARY OF THE INVENTION

The present invention is directed to a method of controlling, treating or reducing the advancement, severity or effects of a mycobacterium disease comprising administering to a patient in need thereof a therapeutically effective amount of gyrase and/or topoisomerase IV inhibitors of formula

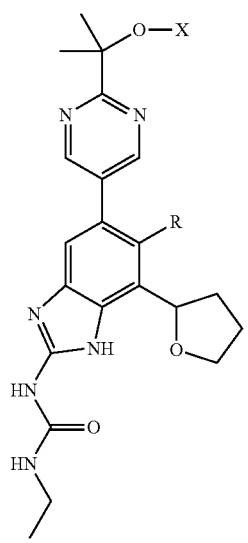

(I)

wherein R is hydrogen or fluorine;
X is hydrogen, —PO(OH)$_2$, —PO(OH)O$^-$M$^+$, —PO(O$^-$)$_2$.2M$^+$, or —PO(O$^-$)$_2$.D$^{2+}$; M$^+$ is a pharmaceutically acceptable monovalent cation; and D$^{2+}$ is a pharmaceutically acceptable divalent cation; or a pharmaceutically acceptable salt thereof; in combination with one or more antibiotic compounds comprising a diarylquinolone, rifapentine, rifalazil, a nitroimidazole, a benzothiazinone, capreomycin, clofazimine, cycloserine, dapsone, a thiocarbamide, ethambutol, DC-159a, a nitrobenzthiazole, sutezolid (PNU-100480), AZD-5847, posizolid (AZD-2563), para-aminosalicylic acid, SQ-109, SQ-609, a capuramycin, a caprazene nucleoside, an isothiazoloquinolone, thioridazine, thiacetazone, dirithromycin, roxithromycin, telithromycin, azithromycin, clarithromycin, erythromycin, amikacin, kanamycin, streptomycin, levofloxacin, moxifloxacin, gatifloxacin, linezolid, rifalazil, meropenem, clavulanate, or isoniazid, with the proviso that when the one or more antibiotic compounds is thioridazine, azithromycin, clarithromycin, erythromycin, amikacin, kanamycin, streptomycin, levofloxacin, moxifloxacin, gatifloxacin, linezolid, rifalazil, meropenem, clavulanate, and isoniazid, then an additional antibiotic is also present in the combination.

In one embodiment, the one or more antibiotic compounds comprises bedaquiline (TMC-207), delaminid (OPC67683), PA 824, TBA-354, SKLB-TB37, BTZ-043, SQ-641, cycloserine, dapsone, ethionamide, prothionamide, para-aminosalicylic acid, CPZEN45, ACH-702 or ACH-710. In another embodiment, the one or more antibiotic compounds comprises bedaquiline, rifapentine, moxifloxacin, linezolid, delaminid, or PA 824. In a furtherr embodiment, the one or more antibiotic compounds comprises moxifloxacin, linezolid, rifalazil, meropenem, clavulanate, pyrazinamide, and isoniazid. In some embodiments, the combination further comprises pyrazinamide.

In one embodiment, the mycobacterial disease is caused by *M. tuberculosis, M. avium intracellulare, M. ulcerans, M. kansasii, M. fortuitum, M. abcesses, M. leprae, M. africanum, M. marinum, M. avium* paratuberculosis, or *M. bovis, M. chelone, M. scrofulaceum, M. xenopi, M. intracellulare,* or *M. micron.* In a further embodiment, the mycobacterium disease is tuberculosis. In some embodiments, the compound of formula (I) is administered with only one antibiotic selected from rifapentine, TMC-207, SQ-109, a nitroimidazole, or an oxazolidinone.

In one embodiment, the present invention is directed to a method of inhibiting the growth of drug sensitive and drug resistant mycobacteria cells wherein the mycobacteria cell is drug sensitive and drug resistant *M. tuberculosis,* drug resistant *M. tuberculosis, M. avium intracellulare, M. ulcerans, M. kansasii, M. fortuitum, M. abcesses, M. leprae, M. africanum, M. marinum, M. avium* paratuberculosis, or *M. bovis.*

DETAILED DESCRIPTION

Figure 1:
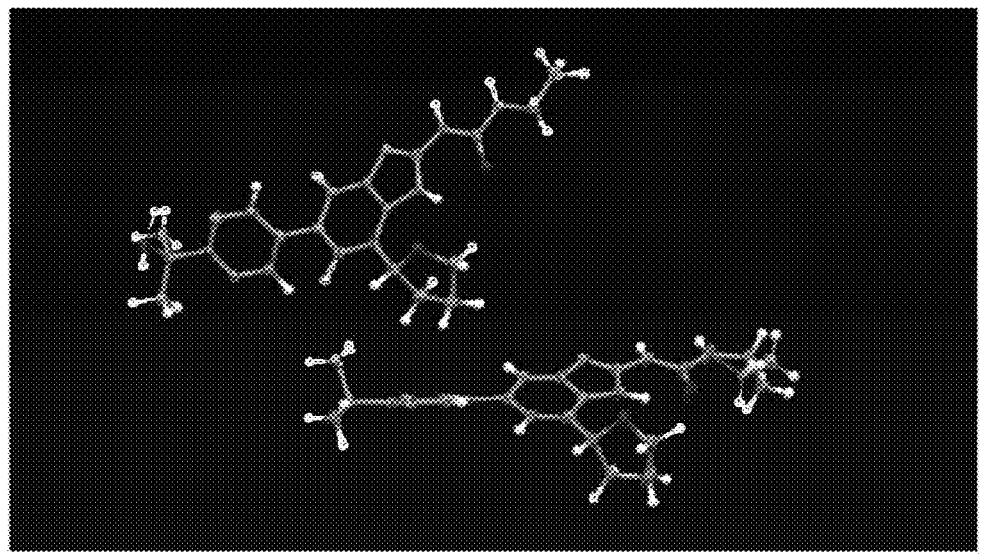
FIG. 1 is a thermal ellipsoid plot of two symmetry independent molecules of compound 12.

The present invention is directed to gyrase and/or topoisomerase IV inhibitors and pharmaceutically acceptable salts thereof, in combination with one or more antibiotics and optionally pyrazinamide.

The present invention provides methods and compositions comprising the compound of formula (I), or a pharmaceutically acceptable salt thereof, in combination with one or more antibiotic agents and, optionally, pyrazinamide effective in treatment and prevention of disease caused by microorganisms including, but not limited to, mycobacteria. In particular, the methods and compositions of the present invention are effective in inhibiting the growth of the microorganism, M. tuberculosis.

As used herein, the term "tuberculosis" comprises disease states usually associated with infections caused by mycobacteria species comprising M. tuberculosis complex. The term "tuberculosis" is also associated with mycobacterial infections caused by mycobacteria other than M. tuberculosis (MOTT). Other mycobacterial species include M. avium-intracellulare, M. kansasii, M. fortuitum, M. chelonae, M. leprae, M. africanum, and M. micron, M. avium paratuberculosis, M. intracellulare, M. scrofulaceum, M. xenopi, M. marinum, M. ulcerans.

The present invention further provides methods and compositions useful for the treatment of infectious disease, including but not limited to, tuberculosis, leprosy, Crohn's Disease, acquired immunodeficiency syndrome, Lyme disease, cat-scratch disease, Rocky Mountain Spotted Fever and influenza.

In one embodiment, the one or more antibiotic is selected from the group consisting with one or more antibiotic compounds comprising a diarylquinolone, rifapentine, rifalazil, a nitroimidazole, a benzothiazinone, capreomycin, clofazimine, cycloserine, dapsone, a thiocarbamide, ethambutol, DC-159a, a nitrobenzthiazole, sutezolid (PNU-100480), AZD-5847, posizolid (AZD-2563), para-aminosalicylic acid, SQ-109, SQ-609, a capuramycin, a caprazene nucleoside, an isothiazoloquinolone, thioridazine, thiacetazone, dirithromycin, roxithromycin, telithromycin, azithromycin, clarithromycin, erythromycin, amikacin, kanamycin, streptomycin, levofloxacin, moxifloxacin, gatifloxacin, linezolid, rifalazil, meropenem, clavulanate, or isoniazid, with the proviso that when the one or more antibiotic compounds is thioridazine, azithromycin, clarithromycin, erythromycin, amikacin, kanamycin, streptomycin, levofloxacin, moxifloxacin, gatifloxacin, linezolid, rifalazil, meropenem, clavulanate, and isoniazid, then an additional antibiotic is also present in the combination.

The combinations of the present invention are effective against disease caused by infectious organisms, including mycobacteria. One embodiment of the invention provides methods and compositions comprising the compound of formula (I), or a pharmaceutically acceptable salt thereof, in combination with one or more antibiotic agents and, optionally, pyrazinamide.

Another embodiment of the invention provides methods and compositions comprising the compound of formula (I), or a pharmaceutically acceptable salt thereof, in combination with one or more antibiotic agents and optionally pyrazinamide that have MIC values of 50 µM or lower for mycobacterial organisms. Another embodiment of the present invention comprises compositions that have an MIC value of 25 µM or lower for mycobacterial organisms. Yet another embodiment of the present invention comprises compositions that have an MIC value of 12.5 µM or lower for mycobacterial organisms. Another embodiment of the present invention comprises compositions that have an MIC value of 5 µM or lower for mycobacterial organisms. In another embodiment of the present invention, the methods and compositions comprise the compound of formula (I), or a pharmaceutically acceptable salt thereof, in combination with one or more antibiotic agents and, optionally, pyrazinamide having FITS Luc activity of 10% or greater.

The present invention contemplates treatment for animals, including, but not limited to, humans. Thus, it is an object of the present invention to provide methods and compositions for the treatment and prevention of diseases caused by mycobacteria such as tuberculosis.

Yet another object of the present invention is to provide methods and compositions for the treatment and prevention of infectious diseases using compositions comprising the compound of formula (I), or a pharmaceutically acceptable salt thereof, in combination with one or more antibiotic agents and, optionally, pyrazinamide.

Another object of the present invention is to provide methods and compositions for the treatment and prevention of mycobacterial disease using compositions comprising the compound of formula (I), or a pharmaceutically acceptable salt thereof, in combination with one or more antibiotic agents and, optionally, pyrazinamide.

Still another object of the present invention is to provide methods and compositions for the treatment and prevention of tuberculosis using compositions comprising the compound of formula (I), or a pharmaceutically acceptable salt thereof, in combination with one or more antibiotic agents and, optionally, pyrazinamide.

Another object of the present invention is to provide methods and compositions for the treatment and prevention of tuberculosis using compositions comprising the compound of formula (I), or a pharmaceutically acceptable salt thereof, in combination with one or more antibiotic agents and, optionally, pyrazinamide, wherein the composition has an MIC value of 50 µM, or less.

Another object of the present invention is to provide methods and compositions for the treatment and prevention of tuberculosis using compositions comprising the compound of formula (I), or a pharmaceutically acceptable salt thereof, in combination with one or more antibiotic agents and, optionally, pyrazinamide, wherein the composition has an MIC value of 25 µM, or less.

Another object of the present invention is to provide methods and compositions for the treatment and prevention of tuberculosis using compositions comprising the compound of formula (I), or a pharmaceutically acceptable salt thereof, in combination with one or more antibiotic agents and, optionally, pyrazinamide, wherein the composition has an MIC value of 12.5 µM, or less.

Yet another object of the present invention is to provide methods and compositions for the treatment and prevention of tuberculosis using compositions comprising the compound of formula (I), or a pharmaceutically acceptable salt thereof, in combination with one or more antibiotic agents and, optionally, pyrazinamide, wherein the composition has an MIC value of 5 µM, or less.

Yet another object of the present invention is to provide methods and compositions for the treatment and prevention of tuberculosis using compositions comprising the compound of formula (I), or a pharmaceutically acceptable salt thereof, in combination with one or more antibiotic agents and, optionally, pyrazinamide, wherein the composition has HTS/Luc activity of 10% or greater.

Yet another object of the present invention is to provide compositions for therapeutic formulations for the treatment and prevention of mycobacterial disease.

Another object of the present invention is to provide compositions for therapeutic formulations for the treatment and prevention of mycobacterial disease caused by mycobacterial species comprising M. tuberculosis complex, M. avium intracellulare, M. kansasii, M. fortuitum, M. chelonoe, M. leprae, M. africanum, M. micron, M. bovis BCG or M. bovis.

Still another object of the present invention is to provide compositions and methods for the treatment or prevention of infectious disease caused by *Mycobacterium-fortuitum, Mycobacterium marinum, Helicobacter pylori, Streptococcus pneumoniae* and *Candida albicans*.

As used herein, the terms "in combination with" and "combinations" refer to the use of two or more agents in one treatment regardless of whether the agents are in a single formulation or in multiple formulations. The use of the term "in combination with" and "combinations" do not restrict the order in which treatments are administered to a subject being treated for a disease caused by a mycobacterium. The administration of the multiple agents may be simultaneous or sequential. A first treatment can be administered prior to, concurrently with, after, or within any cycling regimen involving the administration of a second or third treatment to a subject with a disease or a condition caused by a mycobacterium. For example, one treatment may be administered 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before one or more treatments; or one treatment may be administered 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after one or more treatments. Such treatments include, for example, the administration of compounds having Formula I in combination with pyrazinamide and one or more antibiotic agents.

As used herein, the term "halogen" means F, Cl, Br, or I.

Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the present compounds are within the scope of the invention.

Isotopically-labeled forms of compounds of formula (I) wherein one or more atoms are replaced by an atom having an atomic mass or mass number different from the atomic mass or mass number usually found in nature are also included herein. Examples of isotopes that can be incorporated into compounds of the invention includes isotopes of hydrogen, carbon, nitrogen, oxygen, and fluorine, such as $^2H$, $^3H$, $^{13}C$, $^{14}C$, $^{15}N$, $^{18}O$, and $^{17}O$. Such radio-labeled and stable-isotopically labeled compounds are useful, for example, as research or diagnostic tools or gyrase and/or topoisomerase IV inhibitors with improved therapeutic profile. The structures also encompass zwitterionic forms of the compounds or salts, where appropriate.

The gyrase and/or topoisomerase IV inhibitors of the present invention may be represented by formula (I) or salts thereof:

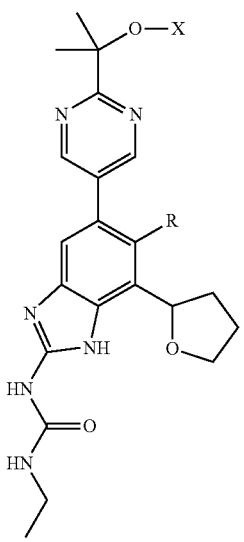

(I)

wherein R is hydrogen or fluorine; X is hydrogen, —PO(OH)$_2$, —PO(OH)O$^-$M$^+$, —PO(O$^-$)$_2$.2M$^+$, or —PO(O$^-$)$_2$.D$^{2+}$; M$^+$ is a pharmaceutically acceptable monovalent cation; and D$^{2+}$ is a pharmaceutically acceptable divalent cation. The compounds of formula (I) either possess abroad range of anti-bacterial activity and advantageous toxicological properties or are prodrugs of compounds having said activity.

The gyrase and/or topoisomerase IV inhibitors of the present invention may be represented by formula (IA):

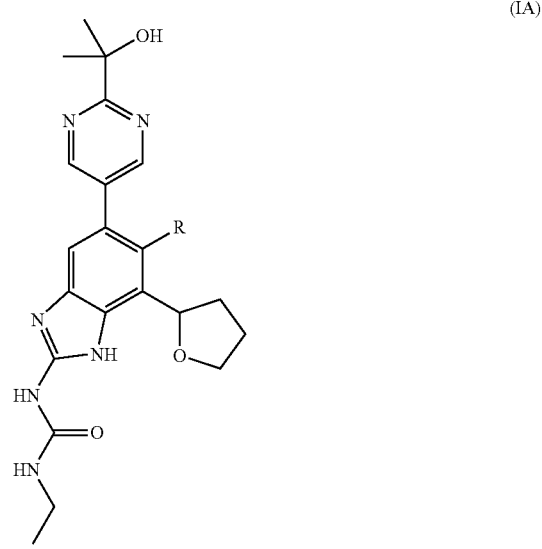

(IA)

wherein R is hydrogen or fluorine. The compounds of formula (IA) possess a broad range of anti-bacterial activity and advantageous toxicological properties.

The gyrase and/or topoisomerase IV inhibitors of the present invention may be represented by formula (IB):

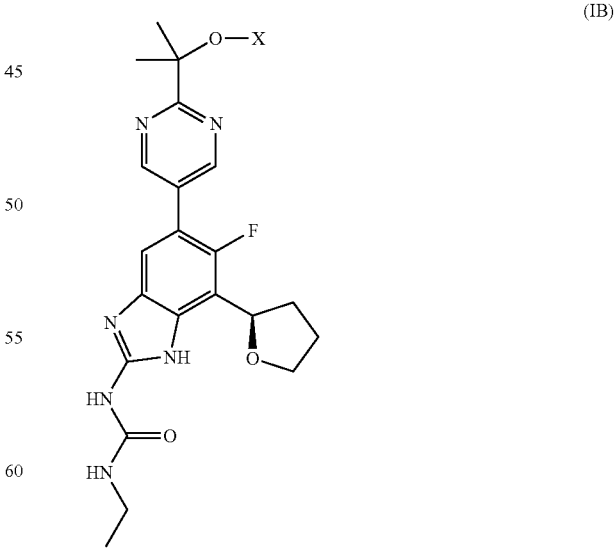

(IB)

wherein X is —PO(OH)$_2$, —PO(OH)O$^-$M$^+$, —PO(O$^-$)$_2$.2M$^+$, or —PO(O$^-$)$_2$.D$^{2+}$; M$^+$ is a pharmaceutically acceptable monovalent cation; and D$^{2+}$ is a pharmaceutically acceptable divalent cation. The compounds of formula (IB) are phosphate ester prodrugs of the compound (R)-1-ethyl-3-(6-fluoro-5-(2-(2-hydroxypropan-2-yl)pyrimidin-5-yl)-7-(tetrahydrofuran-2-yl)-1H-benzo[d]imidazol-2-yl)urea, which possesses a broad range of anti-bacterial activity and advantageous toxicological properties.

In one embodiment, compounds of formula (I) include compounds of formula (IC)

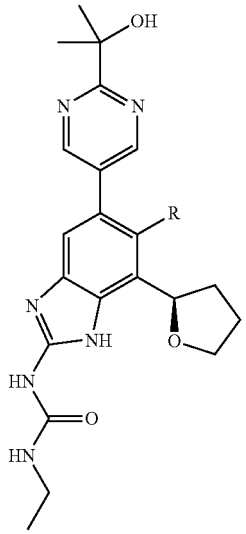

(IC)

wherein R is as defined above.

In another embodiment, compounds of formula (I) include compounds of formulae (ID) and (IE) as set forth below:

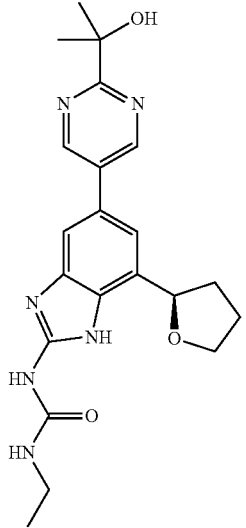

(ID)

(R)-1-ethyl-3-(5-(2-(2-hydroxypropan-2-yl)pyrimidin-5-yl)-7-(tetrahydrofuran-2-yl)-1H-benzo[d]imidazol-2-yl)urea, or a pharmaceutically acceptable salt thereof; and

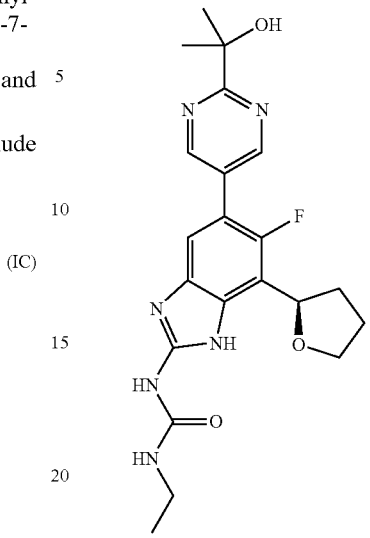

(IE)

(R)-1-ethyl-3-(6-fluoro-5-(2-(2-hydroxypropan-2-yl)pyrimidin-5-yl)-7-(tetrahydrofuran-2-yl)-1H-benzo[d]imidazol-2-yl)urea, or a pharmaceutically acceptable salt thereof. Unless otherwise stated, the phrase "compounds of formula (I)" is intended to include other formulae set forth herein that are encompassed by formula (I) including formulae (IA), (IB), (IC), (ID), and (IE).

The compounds of formula (IB) are prodrugs of their parent compound, 1-ethyl-3-[6-fluoro-5-[2-(1-hydroxy-1-methyl-ethyl)pyrimidin-5-yl]-7-[(2R)-tetrahydrofuran-2-yl]-1H-benzimidazol-2-yl]urea. Thus, the activity exhibited upon administration of the prodrug is principally due to the presence of the parent compound that results from cleavage of the prodrug.

An additional object of the present invention provides embodiments in which the one or more antibiotic compounds comprising a diarylquinolone, rifapentine, rifalazil, a nitroimidazole, a benzothiazinone, capreomycin, clofazimine, cycloserine, dapsone, a thiocarbamide, ethambutol, DC-159a, a nitrobenzthiazole, sutezolid (PNU-100480), AZD-5847, posizolid (AZD-2563), para-aminosalicylic acid, SQ-109, SQ-609, a capuramycin, a caprazene nucleoside, an isothiazoloquinolone, thioridazine, thiacetazone, dirithromycin, roxithromycin, telithromycin, azithromycin, clarithromycin, erythromycin, amikacin, kanamycin, streptomycin, levofloxacin, moxifloxacin, gatifloxacin, linezolid, rifalazil, meropenem, clavulanate, or isoniazid, with the proviso that when the one or more antibiotic compounds is thioridazine, azithromycin, clarithromycin, erythromycin, amikacin, kanamycin, streptomycin, levofloxacin, moxifloxacin, gatifloxacin, linezolid, rifalazil, meropenem, clavulanate, and isoniazid, then an additional antibiotic is also present in the combination. In one embodiment, the additional antibiotic is pyrazinamide.

In one aspect, the present invention provides embodiments in which the one or more antibiotic compounds comprise a diarylquinolone, rifapentine, rifalazil, or a nitrobenzthiazole. In another aspect, pyrazinamide may also be present in the combination. In a further embodiment, the compound of formula (I) includes compounds encompassed by formula (I) including formulae (IA), (IB), (IC), (ID), and (IE). In one aspect, the present invention provides embodiments in which the one or more antibiotic compounds comprise a nitroimidazole, a benzothiazinone, capreomycin, clofazimine, cycloserine, dapsone, a thiocarbamide, ethambutol, DC-159a, or a nitrobenzthiazole. In another aspect, pyrazinamide may also be present in the combination. In a further embodiment, the compound of formula (I) includes compounds encompassed by formula (I) including formulae (IA), (IB), (IC), (ID), and (IE).

In one aspect, the present invention provides embodiments in which the one or more antibiotic compounds comprise a nitroimidazole, a benzothiazinone, capreomycin, clofazimine, cycloserine, dapsone, a thiocarbamide, ethambutol, or DC-159a. In another aspect, pyrazinamide may also be present in the combination. In a further embodiment, the compound of formula (I) includes compounds encompassed by formula (I) including formulae (IA), (IB), (IC), (ID), and (IE).

In one aspect, the present invention provides embodiments in which the one or more antibiotic compounds comprise capreomycin, clofazimine, cycloserine, dapsone, a thiocarbamide, ethambutol, DC-159a, or a nitrobenzthiazole. In another aspect, pyrazinamide may also be present in the combination. In a further embodiment, the compound of formula (I) includes compounds encompassed by formula (I) including formulae (IA), (IB), (IC), (ID), and (IE).

In one aspect, the present invention provides embodiments in which the one or more antibiotic compounds comprise a diarylquinolone, rifapentine, rifalazil, dapsone, a thiocarbamide, ethambutol, DC-159a, or a nitrobenzthiazole. In another aspect, pyrazinamide may also be present in the combination. In a further embodiment, the compound of formula (I) includes compounds encompassed by formula (I) including formulae (IA), (IB), (IC), (ID), and (IE).

In another aspect, the present invention provides embodiments in which the one or more antibiotic compounds comprise sutezolid (PNU-100480), AZD-5847, posizolid (AZD-2563), para-aminosalicylic acid, SQ-109, SQ-609, a capuramycin, a caprazene nucleoside, an isothiazoloquinolone, thioridazine, thiacetazone, dirithromycin, roxithromycin, telithromycin, azithromycin, clarithromycin, erythromycin, amikacin, kanamycin, streptomycin, levofloxacin, moxifloxacin, gatifloxacin, linezolid, rifalazil, meropenem, clavulanate, or isoniazid, with the proviso that when the one or more antibiotic compounds is thioridazine, azithromycin, clarithromycin, erythromycin, amikacin, kanamycin, streptomycin, levofloxacin, moxifloxacin, gatifloxacin, linezolid, rifalazil, meropenem, clavulanate, and isoniazid, then an additional antibiotic is also present in the combination. In another aspect, the additional antibiotic is pyrazinamide. In a further embodiment, the compound of formula (I) includes compounds encompassed by formula (I) including formulae (IA), (IB), (IC), (ID), and (IE).

In another aspect, the present invention provides embodiments in which the one or more antibiotic compounds comprise sutezolid (PNU-100480), AZD-5847, posizolid (AZD-2563), para-aminosalicylic acid, SQ-109, SQ-609, a capuramycin, a caprazene nucleoside, an isothiazoloquinolone, thiacetazone, dirithromycin, roxithromycin, or telithromycin. In another aspect, pyrazinamide may also be present in the combination. In a further embodiment, the compound of formula (I) includes compounds encompassed by formula (I) including formulae (IA), (IB), (IC), (ID), and (IE).

In another aspect, the present invention provides embodiments in which the one or more antibiotic compounds comprise thioridazine, azithromycin, clarithromycin, erythromycin, amikacin, kanamycin, streptomycin, levofloxacin, moxifloxacin, gatifloxacin, linezolid, rifalazil, meropenem, clavulanate, or isoniazid. In another aspect, pyrazinamide may also be present in the combination. In a further embodiment, the compound of formula (I) includes compounds encompassed by formula (I) including formulae (IA), (IB), (IC), (ID), and (IE).

In one embodiment, the one or more antibiotics comprises bedaquiline (TMC-207), delaminid (OPC67683), PA 824, TBA-354, BTZ-043, SQ-641, cycloserine, dapsone, ethionamide, prothionamide, para-aminosalicylic acid, CPZEN45, ACH-702 or ACH-710.

An additional object of the present invention provides embodiments in which the one or more antibiotic agents is pyrazinamide in combination with moxifloxacin, linezolid, rifalazil, meropenem, clavulanate, or isoniazid.

In another embodiment, the oxazolidinone may be linezolid, Sutezolid (PNU-100480), 2-oxazolidone, torezolid, posizolid, eperezolid, radezolid, AZD-5847, or those described in U.S. Pat. Nos. 5,981,528 and 6,605,630.

In another embodiment, the diarylquinoline is bedaquiline (TMC-207).

In a further embodiment, the nitroimidazole may be PA 824, delaminid (OPC-67683), or TBA-354.

In a further embodiment, the one or more antibiotics suitable for the combinations of the present application comprise bedaquiline (TMC-207), delaminid (OPC67683), PA 824, TBA-354, BTZ-043, SQ-641, cycloserine, dapsone, ethionamide, prothionamide, para-aminosalicylic acid, CPZEN45, ACH-702 or ACH-710.

One embodiment of the invention provides methods and compositions comprising the compound of formula (I), or a pharmaceutically acceptable salt thereof, in combination with TMC-207. In a further embodiment, the compound of formula (I) includes compounds encompassed by formula (I) including formulae (IA), (IB), (IC), (ID), and (IE).

One embodiment of the invention provides methods and compositions comprising the compound of formula (I), or a pharmaceutically acceptable salt thereof, in combination with Rifapentine. In a further embodiment, the compound of formula (I) includes compounds encompassed by formula (I) including formulae (IA), (IB), (IC), (ID), and (IE).

One embodiment of the invention provides methods and compositions comprising the compound of formula (I), or a pharmaceutically acceptable salt thereof, in combination with oxazolidinone. In a further embodiment, the compound of formula (I) includes compounds encompassed by formula (I) including formulae (IA), (IB), (IC), (ID), and (IE).

One embodiment of the invention provides methods and compositions comprising the compound of formula (I), or a pharmaceutically acceptable salt thereof, in combination with a nitroimidazole. In a further embodiment, the nitroimidazole is delaminid. In a further embodiment, the compound of formula (I) includes compounds encompassed by formula (I) including formulae (IA), (IB), (IC), (ID), and (IE).

One embodiment of the invention provides methods and compositions comprising the compound of formula (I), or a pharmaceutically acceptable salt thereof, in combination with SQ-109. In a further embodiment, the compound of formula (I) includes compounds encompassed by formula (I) including formulae (IA), (IB), (IC), (ID), and (IE).

One embodiment of the invention provides methods and compositions comprising the compound of formula (I), or a pharmaceutically acceptable salt thereof, in combination with TMC-207 and pyrazinamide. In a further embodiment, the compound of formula (I) includes compounds encompassed by formula (I) including formulae (IA), (IB), (IC), (ID), and (IE).

One embodiment of the invention provides methods and compositions comprising the compound of formula (I), or a pharmaceutically acceptable salt thereof, in combination with rifapentine and pyrazinamide. In a further embodiment, the compound of formula (I) includes compounds encompassed by formula (I) including formulae (IA), (IB), (IC), (ID), and (IE).

One embodiment of the invention provides methods and compositions comprising the compound of formula (I), or a pharmaceutically acceptable salt thereof, in combination with oxazolidinone and pyrazinamide. In a further embodiment, the compound of formula (I) includes compounds encompassed by formula (I) including formulae (IA), (IB), (IC), (ID), and (IE).

One embodiment of the invention provides methods and compositions comprising the compound of formula (I), or a pharmaceutically acceptable salt thereof, in combination with nitroimidazole and pyrazinamide. In a further embidmnet, the nitroimidazole is delaminid. In a further embodiment, the compound of formula (I) includes compounds encompassed by formula (I) including formulae (IA), (IB), (IC), (ID), and (IE).

One embodiment of the invention provides methods and compositions comprising the compound of formula (I), or a pharmaceutically acceptable salt thereof, in combination with pyrazinamide and SQ-109. In a further embodiment, the compound of formula (I) includes compounds encompassed by formula (I) including formulae (IA), (IB), (IC), (ID), and (IE).

One embodiment of the invention provides methods and compositions comprising the compound of formula (I), or a pharmaceutically acceptable salt thereof, in combination with TMC-207, SQ-109, and pyrazinamide. In a further embodiment, the compound of formula (I) includes compounds encompassed by formula (I) including formulae (IA), (IB), (IC), (ID), and (IE).

One embodiment of the invention provides methods and compositions comprising the compound of formula (I), or a pharmaceutically acceptable salt thereof, in combination with clavulanate and meropenem. In a further embodiment, the compound of formula (I) includes compounds encompassed by formula (I) including formulae (IA), (IB), (IC), (ID), and (IE).

One embodiment of the invention provides methods and compositions comprising the compound of formula (I), or a pharmaceutically acceptable salt thereof, in combination with rifapentine, SQ-109, and pyrazinamide. In a further embodiment, the compound of formula (I) includes compounds encompassed by formula (I) including formulae (IA), (IB), (IC), (ID), and (IE).

One embodiment of the invention provides methods and compositions comprising the compound of formula (I), or a pharmaceutically acceptable salt thereof, in combination with oxazolidinone, SQ-109, and pyrazinamide. In a further embodiment, the compound of formula (I) includes compounds encompassed by formula (I) including formulae (IA), (IB), (IC), (ID), and (IE).

One embodiment of the invention provides methods and compositions comprising the compound of formula (I), or a pharmaceutically acceptable salt thereof, in combination with nitroimidazole, SQ-109, and pyrazinamide. In a further embodiment, the nitroimidazole is delaminid. In a further embodiment, the compound of formula (I) includes compounds encompassed by formula (I) including formulae (IA), (IB), (IC), (ID), and (IE).

One embodiment of the invention provides methods and compositions comprising the compound of formula (I), or a pharmaceutically acceptable salt thereof, in combination with clavulanate, meropenem, and SQ-109. In a further embodiment, the compound of formula (I) includes compounds encompassed by formula (I) including formulae (IA), (IB), (IC), (ID), and (IE).

In another embodiment, the invention provides methods and compositions comprising the compound of formula (I), or a pharmaceutically acceptable salt thereof, in combination with one or more of thiacetazone, dirithromycin, roxithromycin, telithromycin, azithromycin, clarithromycin, erythromycin, amikacin, kanamycin, streptomycin, and levofloxacin. In a further embodiment, the compound of formula (I) includes compounds encompassed by formula (I) including formulae (IA), (IB), (IC), (ID), and (IE).

In another embodiment, the invention provides methods and compositions comprising the compound of formula (I), or a pharmaceutically acceptable salt thereof, in combination with pyrazinamide one or more of thiacetazone, dirithromycin, roxithromycin, telithromycin, azithromycin, clarithromycin, erythromycin, amikacin, kanamycin, streptomycin, and levofloxacin. In a further embodiment, the compound of formula (I) includes compounds encompassed by formula (I) including formulae (IA), (IB), (IC), (ID), and (IE).

In another embodiment, the invention provides methods and compositions comprising the compound of formula (I), or a pharmaceutically acceptable salt thereof, in combination with pyrazinamide one or more of azithromycin, clarithromycin, erythromycin, amikacin, kanamycin, streptomycin, and levofloxacin. In a further embodiment, the compound of formula (I) includes compounds encompassed by formula (I) including formulae (IA), (IB), (IC), (ID), and (IE).

The term "capuramycins" as used herein refers to a class of antibiotic useful for treating bacterial infections based on capuramycin. Capuramycin (general formula $C_{23}H_{31}O_{12}N_5$) is a nucleoside antibiotic produced by *Streptomyces griseus* 446-S3 active against *streptococcus pneumoniae* and *Mycobacterium smegmatis* ATCC 607 and has the following structure:

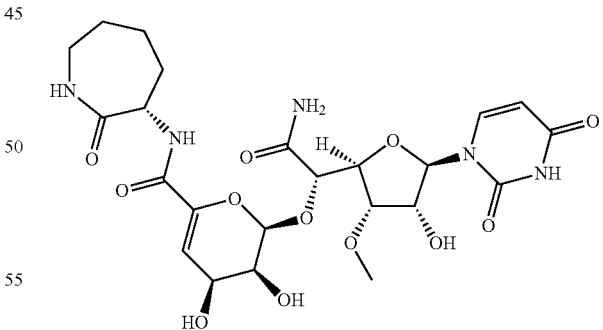

Examples of capuramycins suitable for the combinations of the present application include capuramycin and the capuramycin analogue SQ-641.

As used herein, the term "aminocoumarin" refers to a class of antibiotics that act by an inhibition of the DNA Gyrase enzyme involved in the cell division in bacteria. They are derived from *Streptomyces* species. Examples of aminocoumarin antibiotics include novobiocin, cloroblocin, coumermycin, ferulobiocin, 3-chlorocoumarobiocin and 8'-dechloro-3-chlorocoumarobiocin. Additional aminocoumarins suitable for the combinations of the present invention include those described in Li, S. M. and Heide L. *Curr. Med. Chem.* 12:419-27 (2005) and in Friedman, M. et al. *Biochem.*, 46:8462-71 (2007).

Isothiazoloquinolones suitable for the combinations of the present invention include ACH-710, ACH-702 (described by Pucci, M. J. et al. in *Antimicrob. Agents Chemother.*, 55:2860-71 (2011)), and those disclosed in U.S. Application Publication No. 2012/0114601.

The term "benzothiazinones" as used herein refers to a class of compounds based on the structure:

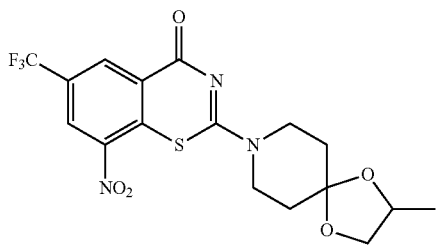 [SMILES: CC1COC2(CCN(c3nc(=O)c4cc(C(F)(F)F)cc([N+](=O)[O-])c4s3)CC2)O1]

or the structure:

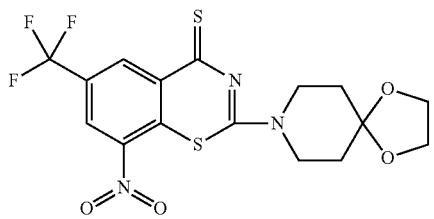 [SMILES: O=[N+]([O-])c1cc(C(F)(F)F)cc2c(=S)nc(N3CCC4(CC3)OCCO4)sc12]

useful for treating mycobacterial infection. Examples of benzothiazinones suitable for the combinations of the present invention include BTZ 043, SKLB-TB37 and those disclosed in EP 2468746 and CN102276598, Riminophenazine antibiotics suitable for the combinations of the present invention include clofazimine (B663) and B669. The term "diarylquinolone" as used herein refers to a class of compounds useful for treating mycobacterium and includes, but is not limited to, bedaquiline (TMC-207) and R207910. Bedaquiline has an IUPAC name of (1R,2S)-1-(6-Bromo-2-methoxy-3-quinolyl)-4-dimethylamino-2-(1-naphthyl)-1-phenyl-butan-2-ol and may be synthesized according to the methods disclosed in WO2004/011436 and WO2006/125769.

The term "rifapentine" as used herein refers to an antibiotic useful for treating bacterial infections. Rifapentine has an IUPAC name of (7S,9E,11S,12R,13S,14R,15R,16R,17S,18S,19E,21Z,26E)-26-{[(4-cyclopentylpiperazin-1-yl)amino]methylidene}-2,15,17,29-tetrahydroxy-1'-methoxy-3,7,12,14,16,18,22-heptamethyl-6,23,27-trioxo-8,30-dioxa-24-azatetracyclo[23.3.1.1$^{4,7}$.0$^{5,28}$]triaconta-1(28),2,4,9,19,21,25(29)-heptaen-13-yl acetate and it may be purchased commercially (e.g., Sigma-Aldrich; Cat. No. R0533).

The term "rifampin" or "rifampicin" as used herein refers to an antibiotic useful for treating bacterial infections. Rifampin has an IUPAC name of: (7S,9E,11S,12R,13S,14R,15R,16R,17S,18S,19E,21Z)-2,15,17,27,29-pentahydroxy-1'-methoxy-3,7,12,14,16,18,22-heptamethyl-26-{(E)-[(4-methylpiperazin-1-yl)imino]methyl}-6,23-dioxo-8,30-dioxa-24-azatetracyclo[23.3.1.1$^{4,7}$0.0$^{5,28}$]triaconta-1(28),2,4,9,19,21,25(29),26-octaen-13-yl acetate and it may be purchased commercially (e.g., Fisher BioReagents (Cat No. BP2679-1) or Sigma-Aldrich (Cat. No. R3501)).

The following table provides structure and sources for some of the antibiotic compounds suitable for the combinations of the present application.

TABLE 1

| Compound (Name and/or structure) | Chemical Name and/or Synthesis/Isolation/Commercial Availability |
| --- | --- |
| Bedaquiline | IUPAC name: (1R,2S)-1-(6-Bromo-2-mthoxy-3-quinolyl)-4-dimethylamino-2-(1-naphthyl)-1-phenyl-butan-2-ol |
| | Synthesis: WO2004/011436 and process for chiral resolution in WO 2006/125769. |

TABLE 1-continued

| Compound (Name and/or structure) | Chemical Name and/or Synthesis/Isolation/Commercial Availability |
|---|---|
| Rifapentine 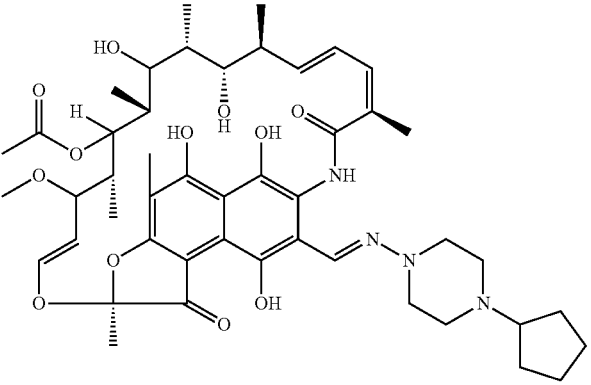 | IUPAC Name: (7S,9E,11S,12R,13S,14R,15R,16R,17S,18S,19E,21Z, 26E)-26-{[(4-cyclopentylpiperazin-1-yl)amino]methylidene}-2,15,17,29-tetrahydroxy-11-methoxy-3,7,12,14,16,18,22-heptamethyl-6,23,27-trioxo-8,30-dioxa-24-azatetracyclo[23.3.1.1$^{4,7}$.0$^{5,28}$]triaconta-1(28),2,4,9,19,21,25(29)-heptaen-13-yl acetate<br><br>*Synthesis/Isolation/Commercial Availability (Sigma-Aldrich; Cat. No. R0533) |
| Rifampin (Rifampicin or Rifadin): 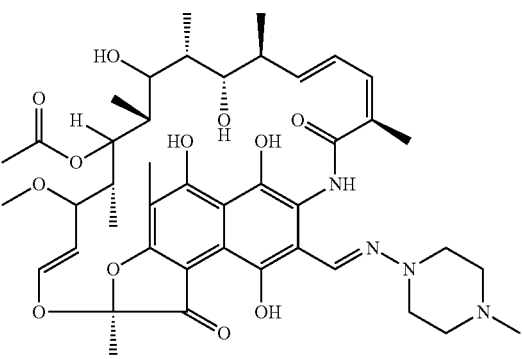 | IUPAC name: (7S,9E,11S,12R,13S,14R,15R,16R,17S,18S,19E,21Z)-2,15,17,27,29-pentahydroxy-11-methoxy-3,7,12,14,16,18,22-heptamethyl-26-{(E)-[(4-methylpiperazin-1-yl)imino]methyl}-6,23-dioxo-8,30-dioxa-24-azatetracyclo[23.3.1.1$^{4,7}$.0$^{5,28}$]triaconta-1(28),2,4,9,19,21,25(29),26-octaen-13-yl acetate.<br><br>Synthesis/Isolation/Commercial Availability: can be purchased from Fisher BioReagents (Cat No. BP2679-1) or Sigma-Aldrich (Cat. No. R3501) |
| 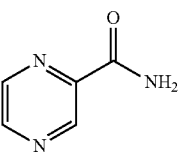<br>Pyrazinamide | *IUPAC Name: pyrazine-2-carboxamide<br><br>Synthesis/Isolation/Commercial Availability: can be purchased from several U.S. sources (Sigma-Aldrich Cat. No. P1736) |
| Isoniazid: (also abbreviated as INH; generic)<br>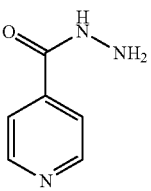 | *IUPAC Name: isonicotinohydrazide<br><br>*Synthesis/Isolation/Commercial Availability: can be purchased from Sigma Aldrich (Cat. No. I3377) |

TABLE 1-continued

| Compound (Name and/or structure) | Chemical Name and/or Synthesis/Isolation/Commercial Availability |
|---|---|
| Moxifloxacin<br />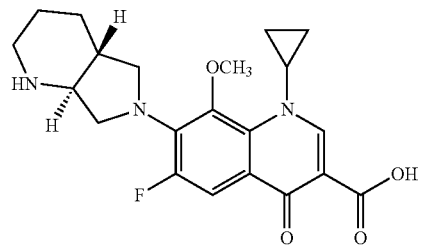 [SMILES: COc1c(N2C[C@H]3CCCN[C@@H]3C2)c(F)cc2c(=O)c(C(=O)O)cn(C3CC3)c12] | *IUPAC name: 1-cyclopropyl-7-[(1S,6S)-2,8-diazabicyclo[4.3.0]non-8-yl]-6-fluoro-8-methoxy-4-oxo-quinoline-3-carboxylic acid<br />*<br />*Synthesis/Isolation/Commercial Availability: can be purchased from Sigma Aldrich (Cat. No. 32477) |
| Gatifloxacin (Gatiflo, Tequin, Zymar, BMS, Kyorin)<br />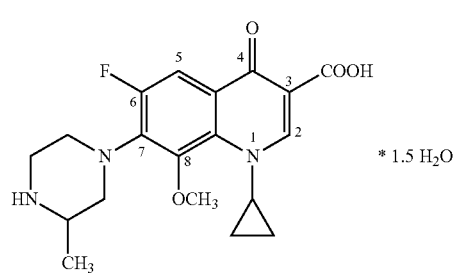 [SMILES: COc1c(N2CCNC(C)C2)c(F)cc2c(=O)c(C(=O)O)cn(C3CC3)c12] * 1.5 H$_2$O | *IUPAC name: 1-cyclopropyl-6-fluoro-8-methoxy-7-(3-methylpiperazin-1-yl)-4-oxo-quinoline-3-carboxylic acid<br /><br />*Synthesis/Isolation/Commercial Availability: can be purchased from Sigma Aldrich (Cat. No. G7298) |
| Linezolid<br />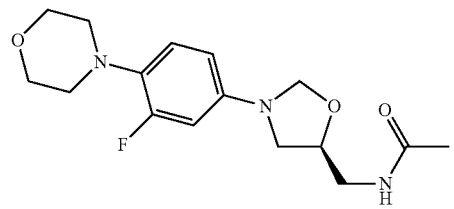 [SMILES: CC(=O)NC[C@H]1CN(c2ccc(N3CCOCC3)c(F)c2)CO1] | *IUPAC Name: (S)-N-({3-[3-fluoro-4-(morpholin-4-yl)phenyl]-2-oxo-1,3-oxazolidin-5-yl}methyl)acetamide<br /><br />Synthesis/Isolation/Commercial Availability: can be purchased from Sigma Aldrich (Cat. No. PZ0014) |
| Sutezolid (PNU-100480, Pfizer):<br />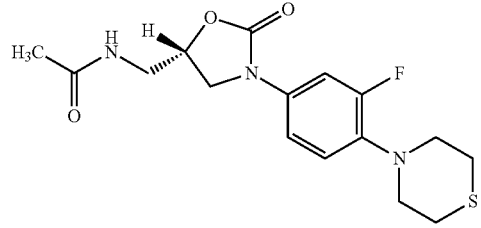 [SMILES: CC(=O)NC[C@H]1CN(c2ccc(N3CCSCC3)c(F)c2)C(=O)O1] | Synthesis/Isolation/Commercial Availability: can be purchased from Axon MedChem BV, Postbus 770 Groningen, 9700 AT Netherlands (Cat. No. Axon 1762) |
| Posizolid (Astra Zeneca)<br />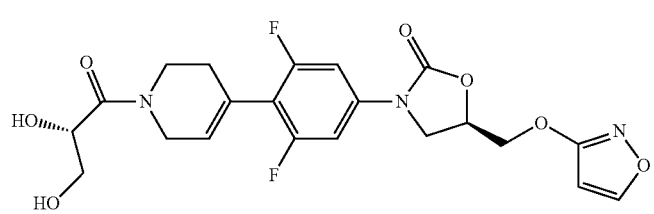 [SMILES: O=C([C@@H](O)CO)N1CC=C(c2c(F)cc(N3C[C@H](COc4ccon4)OC3=O)cc2F)CC1] | IUPAC Name: (5R)-3-[4-[1-[(2S)-2,3-Dihydroxypropanoyl]-3,6-dihydro-2H-pyridin-4-yl]-3,5-difluorophenyl]-5-(1,2-oxazol-3-yloxymethyl)-1,3-oxazolidin-2-one<br /><br />Synthesis/Isolation/Commercial Availability: can be purchased from BOC Sciences, 45-16 Ramsey Road, Shirley, NY 11967 (Cat. No. 252260-02-9) |

TABLE 1-continued

| Compound (Name and/or structure) | Chemical Name and/or Synthesis/Isolation/Commercial Availability |
|---|---|
| AZD-5847 | *Synthesis/Isolation: Process for preparing the phosphate ester prodrug WO0140236. |
| PA 824 (structure shown) | *IUPAC name: (6S)-2-nitro-6-{[4-(trifluoromethoxy)benzyl]oxy}-6,7-dihydro-5H-imidazo[2,1-b][1,3]oxazine<br><br>*Synthesis/Isolation/Commercial Availability: can be purchased from BOC Sciences, 45-16 Ramsey Road, Shirley, NY 11967 (Cat. No. 187235-37-6) |
| Ethambutol (structure shown) | IUPAC name: (2S,2'S)-2,2'-(Ethane-1,2-diyldiimino)dibutan-1-ol<br><br>*Synthesis/Isolation/Commercial Availability: can be purchased from Sigma Aldrich (Cat. No. E4630) |
| SQ-109: (Sequella) (structure shown) | *Synthesis/Isolation/Commercial Availability: can be purchased from Aurora Fire Chemicals LLC, 7929 Silverton Ave., San Diego, CA 92126 (Cat. No. K06.990.223); also see U.S. Pat. No. 6,951,961) |
| SQ-609 (Sequella): (structure shown) | *IUPAC Name: 1-{[1-(Adamantan-1-ylmethyl)-4-piperidinyl]methyl}-4-piperidinol<br><br>*Synthesis/Isolation/Commercial Availability: WO03096987; also Bioorganic and Med Chem Letters 21 (18), pp 5353-5357 (2011) and Bioorganic and Med Chem Letters 20 (1), pp. 201-205 (2010). |
| 5Q641 (structure shown) | *Synthesis/Isolation/Commercial Availability: WO2009136965; also Bioorganic and Med Chem Letters 21 (18), pp. 5353-5357 (2011) |

TABLE 1-continued

| Compound (Name and/or structure) | Chemical Name and/or Synthesis/Isolation/Commercial Availability |
|---|---|
| Delaminid (OPC-67683, Otsuka) | Chemical name: (2R)-2-methyl-6-nitro-2-[(4-{4-[4-(trifluoromethoxy)phenoxy]piperidin-1-yl}phenoxy)methyl]-2,3-dihydroimidazo[2,1-b]oxazole<br><br>*Synthesis/Isolation/Commercial Availability: JP2005330266; WO20044033463; WO2004035547 (process app) also J. Med Chem. 49 (26), pp. 7854-7860 (2006) |
| Clofazimine (Lamprine) | IUPAC name: N,5-bis(4-chlorophenyl)-3-(propan-2-ylimino)-3,5-dihydrophenazin-2-amine<br><br>*Synthesis/Isolation/Commercial Availability: can be purchased from Sigma Aldrich (Cat. No. C8895) |
| Dapsone (Aczone) | *IUPAC name: 4-[(4-aminobenzene)sulfonyl]aniline<br><br>*Synthesis/Isolation/Commercial Availability: can be purchased from Sigma Aldrich (Cat. No. A74807) |
| Rifafour | A combo tablet containing the 4 first line TB agents of Rifampicin (150 mg) + Isoniazid (75 mg) + Pyrazinamide (400 mg) + Ethambutol (275 mg). |
| BTZ 043 | *Synthesis/Isolation/Commercial Availability: can be purchased from BOC Sciences, 45-16 Ramsey Road, Shirley, NY 11967 (Cat. No. 1161233-85-7) |

TABLE 1-continued

| Compound (Name and/or structure) | Chemical Name and/or Synthesis/Isolation/Commercial Availability |
|---|---|
| Capreomycin 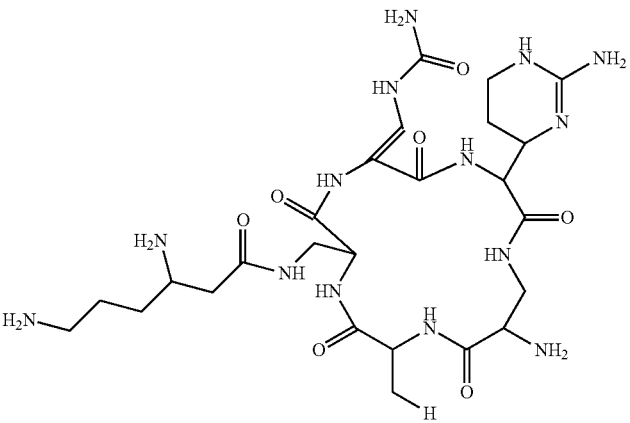 [SMILES: CC1NC(=O)C(N)CNC(=O)C(C2CCNC(N)=N2)NC(=O)/C(=C/NC(N)=O)NC(=O)C(CNC(=O)CC(N)CCCN)NC1=O] | *Synthesis/Isolation/Commercial Availability: can be purchased from Sigma Aldrich (Cat. No. C4142) |
| Cycloserine 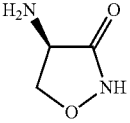 | Synthesis/Isolation/Commercial Availability: can be purchased from Sigma Aldrich (Cat. No. C7005 for DL-Cycloserine; C1159 for L-Cycloserine; C6680 for D-Cycloserine) |
| Ethionamide 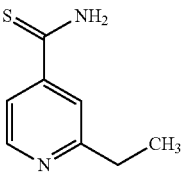 | Synthesis/Isolation/Commercial Availability: can be purchased from Sigma Aldrich (Cat. No. E6005) |
| DC-159a 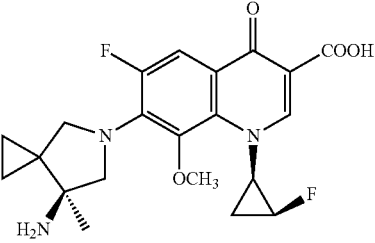 [SMILES: COc1c(N2CC3(CC3)[C@](C)(N)C2)c(F)cc2c(=O)c(C(=O)O)cn([C@@H]3C[C@@H]3F)c12] | *Synthesis/Isolation/Commercial Availability: WO2007111023 (in Japanese; Daiichi Pharmaceutical Co.); also Bioorganic and Med Chem Letters 21 (18), pp. 5353-5357 (2011) |
| Prothionamide 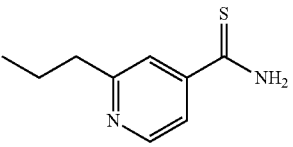 | *Synthesis/Isolation/Commercial Availability: can be purchased from BOC Sciences, 45-16 Ramsey Road, Shirley, NY 11967 (Cat. No. 14222-60-7) |
| 4-aminosalicyclic acid 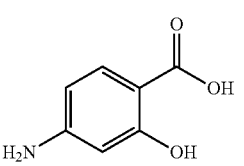 [SMILES: Nc1ccc(C(=O)O)c(O)c1] | *Synthesis/Isolation/Commercial Availability: can be purchased from Alfa Aesar, 26 Parkridge Rd., Ward Hill, MA 01835 (Cat. No. B23289) |

TABLE 1-continued

| Compound (Name and/or structure) | Chemical Name and/or Synthesis/Isolation/Commercial Availability |
|---|---|
| Rifalazil | *Synthesis/Isolation/Commercial Availability: can be purchased from BOC Sciences, 45-16 Ramsey Road, Shirley, NY 11967 (Cat. No. 129791-92-0) |
| CPZEN45 (Caprazamycin analogue) | *Synthesis/Isolation/Commercial Availability: WO2010038874 and WO2008020560 (both in Japanese); also Bioorganic and Med Chem Letters 21 (18), pp. 5353-5357 (2011) |
| ACH-710 (isothiazoloquinolone) | *Synthesis/Isolation/Commercial Availability: WO200821491 and WO2007014308 (both in Japanese); also Bioorganic and Med Chem Letters 21 (18), pp. 5353-5357 (2011) |

FIG. 1/Chemical structure of ACH-702.

TABLE 1-continued

| Compound (Name and/or structure) | Chemical Name and/or Synthesis/Isolation/Commercial Availability |
|---|---|
| Meropenem (beta lactam class and belongs to the carbapenem subgroup) | *Synthesis/Isolation/Commercial Availability: can be purchased from Sigma Aldrich (Cat. No. M2574) |
| Clavulanate (Clavulanate Potassium) (Beta lactamase inhibitors) Clavulanic acid | *Synthesis/Isolation/Commercial Availability: can be purchased from Sigma Aldrich (Cat. No. 33454) |
| Thioridiazine | Synthesis/Isolation/Commercial Availability: can be purchased from Sigma Aldrich (Cat. No. T9025) |
| Q201 (Imidazopyridine) in preclinical development by Qurient Therapeutics) | |
| Thiacetazone | Approved drug |
| Levofloxacin | *Commercial Availability: can be purchased from Sigma Aldrich (Cat. No. 28266) |

TABLE 1-continued

| Compound (Name and/or structure) | Chemical Name and/or Synthesis/Isolation/Commercial Availability |
|---|---|
| SKLB-TB37 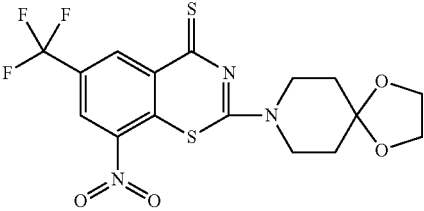 [SMILES: O=[N+]([O-])c1cc(C(F)(F)F)cc2c(=S)nc(N3CCC4(CC3)OCCO4)sc12] | *Synthesis/Isolation: CN102276598A |
| Azithromycin 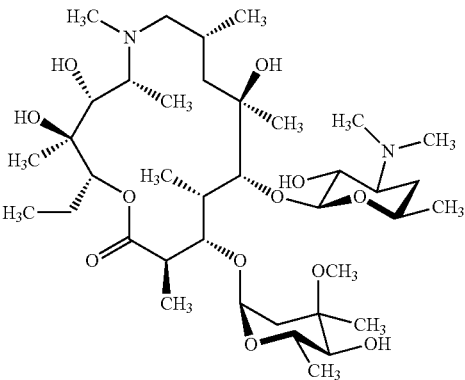 | *Commercial Availability: can be purchased from\ Sigma Aldrich (Cat. No. PZ0007) |
| Clarithromycin 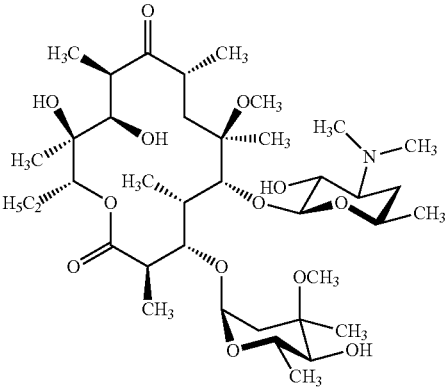 | *Commercial Availability: can be purchased from Sigma Aldrich (Cat. No. C9742) |
| Erythromycin 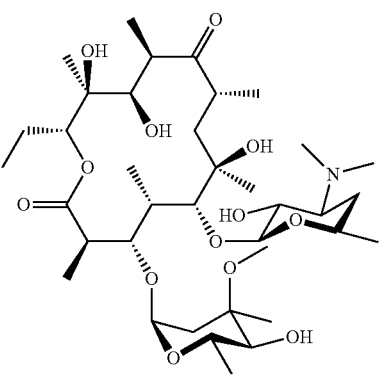 | *Commercial Availability: can be purchased from Sigma Aldrich (Cat. No. E6376) |

TABLE 1-continued

| Compound (Name and/or structure) | Chemical Name and/or Synthesis/Isolation/Commercial Availability |
|---|---|
| Dirithromycin 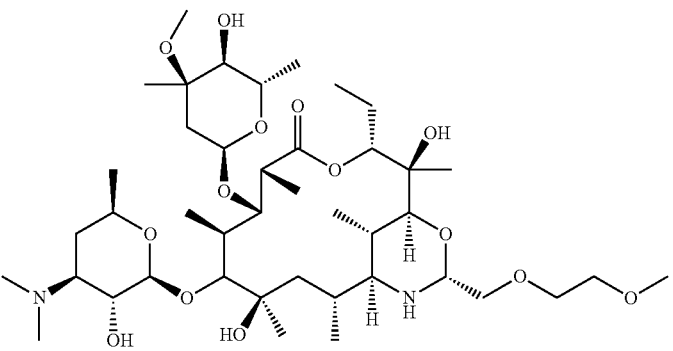 | *Commercial Availability: can be purchased from Sigma Aldrich (Cat. No. D4065) |
| Roxithromycin 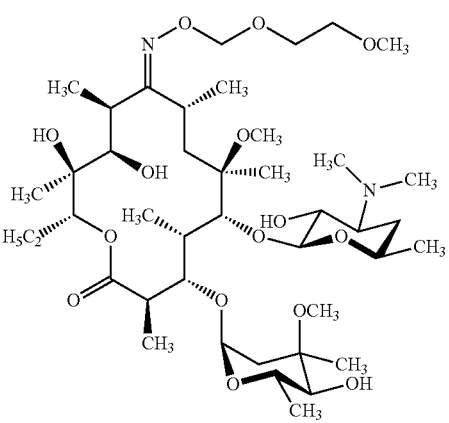 | *Commercial Availability: can be purchased from Sigma Aldrich (Cat. No. R4393) |
| Telithromycin 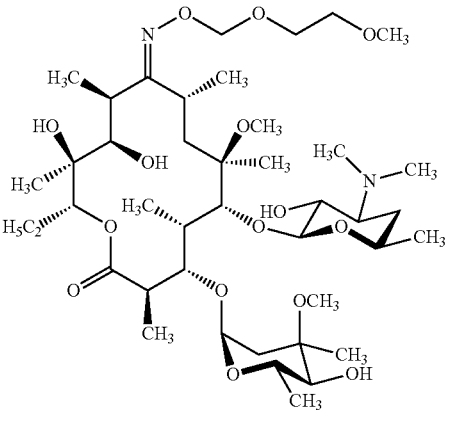 | *Approved Drug |

For the compound of formula (I), dosage levels of between about 0.01 and about 100 mg/kg body weight per day, preferably between 0.5 and about 75 mg/kg body weight per day and most preferably between about 1 and 50 mg/kg body weight per day of the active ingredient compound are useful in a monotherapy for the prevention and treatment of bacterial infections.

Typically, the pharmaceutical compositions of this invention will be administered from about 1 to 5 times per day or alternatively, as a continuous infusion. Alternatively, the compositions of the present invention may be administered in a pulsatile formulation. Such administration can be used as a chronic or acute therapy. The amount of active ingredient that may be combined with the carrier materials to produce a single dosage form will vary depending upon the host treated and the particular mode of administration A typical preparation will contain from about 5% to about 95% active compound (w/w). Preferably, such preparations contain from about 20% to about 80% active compound.

When the compositions of this invention comprise a combination of a compound of formula (I) and one or more additional therapeutic or prophylactic agents, both the compound and the additional agent should be present at dosage levels of between about 10% to 80% of the dosage normally administered in a monotherapy regime.

Upon improvement of a patient's condition, a maintenance dose of a compound, composition or combination of this invention may be administered, if necessary. Subsequently, the dosage or frequency of administration, or both, may be reduced, as a function of the symptoms, to a level at which the improved condition is retained when the symptoms have been alleviated to the desired level, treatment should cease. Patients may, however, require intermittent treatment on a long-term basis upon any recurrence or disease symptoms.

As the skilled artisan will appreciate, lower or higher doses than those recited above may be required. Specific dosage and treatment regimens for any particular patient will depend upon a variety of factors, including the activity of the specific compound employed, the age, body weight, general health status, sex, diet, time of administration, rate of excretion, drug combination, the severity and course of the disease, and the patient's disposition to the disease and the judgment of the treating physician.

According to another embodiment, the invention provides methods for treating or preventing a bacterial infection, or disease state, comprising the step of administering to a patient any compound, pharmaceutical composition, or combination described herein. The term "patient", as used herein, means an animal, preferably a mammal, and most preferably a human.

The U.S. Department of Health and Human Services Centers for Disease Control and Prevention have published recommendations for the treatment of tuberculosis. Centers for Disease Control and Prevention. *Treatment of Tuberculosis*, American Thoracic Society, CDC, and Infectious Diseases Society of America. MMWR 2003; 52(No. RR-11):1-80, incorporated by reference herein as if fully set forth. In these recommendations are disclosed various first-line and second-line drugs used to treat TB as well as recommended treatment regimens including combinations of known compounds, the recommended interval and dosages and range of total doses for both adults and children. In addition, treatment algorithms for TB and active, culture-negative pulmonary TB and inactive TB are provided as well as management of relapse, treatment failure and drug resistance. For the purposes of this invention, a compound of formula (I) may be added to the specific treatment regimens set forth therein or substituted for one of the components listed in the treatment regimens, either as a first-line or second-line drug.

The recommended treatment regimens are, in large part, based on evidence from clinical trials and are rated on the basis of a system developed by the United States Public Health Service (USPHS) and the Infection Diseases Society of America (IDSA). The rating system includes a letter (A, B, C, D, or E) that indicates the strength of the recommendation and a roman numeral (I, II, or III) that indicates the quality of evidence supporting the recommendation (Table 2).

There are four recommended regimens for treating patients with TB caused by drug-susceptible organisms as set forth in the 2003 guidance document. Each regimen has an initial phase of 2 months followed by a choice of several options for the continuation phase of either 4 or 7 months. The recommended regimens together with the number of doses specified by the regimen are described in Table 3. The initial phases are denoted by a number (1, 2, 3, or 4) and the continuation phases that relate to the initial phase are denoted by the number plus a letter designation (a, b, or c). Drug doses are shown in Tables 4, 5, and 6.

TABLE 2a

Infectious Diseases Society of America/United States Public Health Service rating system for the strength of treatment recommendations based on quality of evidence Strength of the recommendation
   A. Preferred; should generally be offered
   B. Alternative; acceptable to offer
   C. Offer when preferred or alternative regimens cannot be given
   D. Should generally not be offered
   E. Should never be offered
Quality of evidence supporting the recommendation
   I. At least one properly randomized trial with clinical end points
   II. Clinical trials that either are not randomized or were conducted in other populations
   III. Expert opinion TABLE 2b Drug regimens for culture-positive pulmonary tuberculosis caused by drug-susceptible organisms

| | | Initial phrase | | | Continuation phase | Range of total | Rating* | |
|---|---|---|---|---|---|---|---|---|
| | | Interval and doses‡ | | | Interval and doses‡§ | doses (minimal | (evidence)† | |
| Regimen | Drugs | (minimal duration) | Regimen | Drugs | (minimal duration) | duration) | HIV⁻ | HIV⁺ |
| 1 | INH | Seven days per week for 56 doses | 1a | INH/RIF | Seven days per week for 126 doses (18 wk) or 5 d/wk for 90 doses (18 wk)¶ | 182-130 (26 wk) | A (I) | A (II) |
| | RIF | (8 wk) or 5 d/wk for 40 doses | | | | | | |
| | PZA | (8 wk)¶ | | | | | | |
| | EMB | | 1b | INH/RIF | Twice weekly for 36 doses (18 wk) | 92-76 (26 wk) | A (I) | A (II)# |
| | | | 1c** | INH/RPT | Once weekly for 18 doses (18 wk) | 74-58 (26 wk) | B (I) | E (I) |
| 2 | INH | Seven days per week for 14 doses | 2a | INH/RIF | Twice weekly for 36 doses (18 wk) | 62-58 (26 wk) | A (II) | B (II)# |
| | RIF | (2 wk), then twice weekly for 12 doses (6 wk) or 5 d/wk for 10 doses (2 wk),¶ then twice weekly for 12 doses (6 wk) | 2b** | INH/RPT | Once weekly for 18 doses (18 wk) | 44-40 (26 wk) | B (I) | E (I) |
| | PZA | | | | | | | |
| | EMB | | | | | | | |
| 3 | INH | Three times weekly for 24 doses (8 wk) | 3a | INH/RIF | Three times weekly for 54 doses (18 wk) | 78 (26 wk) | B (I) | B (II) |
| | RIF | | | | | | | |
| | PZA | | | | | | | |
| | EMB | | | | | | | |

TABLE 2b-continued

Drug regimens for culture-positive pulmonary tuberculosis caused by drug-susceptible organisms

| | Initial phrase | | | Continuation phase | | Range of total | Rating* | |
|---|---|---|---|---|---|---|---|---|
| | | Interval and doses‡ | | | Interval and doses‡§ | doses (minimal | (evidence)† | |
| Regimen | Drugs | (minimal duration) | Regimen | Drugs | (minimal duration) | duration) | HIV⁻ | HIV⁺ |
| 4 | INH | Seven days per week for 56 doses | 4a | INH/RIF | Seven days per week for 217 doses (31 wk) or 5 d/wk for 155 doses (31 wk)¶ | 273-195 (39 wk) | C (I) | C (II) |
| | RIF | (8 wk) or 5 d/wk for 40 doses | | | | | | |
| | EMB | (8 wk)¶ | 4b | INH/RIF | Twice weekly for 62 doses (31 wk) | 118-102 (39 wk) | C (I) | C (II) |

Definition of abbreviations: EMB = Ethambutol; iNH = isoniazid; PZA = pyrazinamide; RIF = rifampin; RPT = rifapentine
*Definitions of evidence ratings: A = preferred; B = acceptable alternative; C = offer when A and B cannot be given; E = should never be given.
†Definition of evidence ratings: I = randomized clinical trial; II = data from clinical trials that were not randomized or were conducted in other populations; III = expert opinion.
‡When DOT is used, drugs may be given 5 days/week and the necessary number of doses adjusted accordingly. Although there are no studies that compare five with seven daily doses, extensive experience indicates this would be an effective practice.
§Patients with cavitation on initial chest radiograph and positive cultures at completion of 2 months of therapy should receive a 7-month (31 week; either 217 doses [daily] or 62 doses [twice weekly]) continuation phase.
¶Five-day-a-week administration is always given by DOT. Rating for 5 day/week regimens is AIII
Not recommended for HIV-infected patients with CD4⁺ cell counts <100 cells/μl.
**Options 1c and 2b should be used only in HIV-negative patients who have negative sputum smears at the time of completion of 2 months of therapy and who do not have cavitation on initial chest radiograph (see text). For patients started on this regimen and found to have a positive culture from the 2-month specimen, treatment should be extended an extra 3 months.

TABLE 3

Doses of antituberculosis drugs for adults and children

| | | | Doses | | | |
|---|---|---|---|---|---|---|
| Drug | Preparation | Adults/children | Daily | 1×/wk | 2×/wk | 3×/wk |
| First-line drugs | | | | | | |
| Isoniazid | Tablets (50 mg, 100 mg, 300 mg); elixir (50 mg/ 5 ml); aqueous solution (100 mg/ml) for intravenous or intramuscular injection | Adults (max.) Children (max.) | 5 mg/kg (300 mg) 10-15 mg/kg (300 mg) | 15 mg/kg (900 mg) — | 15 mg/kg (900 mg) 20-30 mg/kg (900 mg) | 15 mg/kg (900 mg) — |
| Rifampin | Capsule (150 mg, 300 mg); powder may be suspended for oral administration, aqueous solution for intravenous injection | Adults‡ (max.) Children (max.) | 10 mg/kg (600 mg) 10-20 mg/kg (600 mg) | — — | 10 mg/kg (600 mg) 10-20 mg/kg (600 mg) | 10 mg/kg (600 mg) — |
| Rifabutin | Capsule (150 mg) | Adults‡ (max.) Children | 5 mg/kg (300 mg) Appropriate dosing for children is unknown | — Appropriate dosing for children is unknown | 6 mg/kg (300 mg) Appropriate dosing for children is unknown | 5 mg/kg (300 mg) Appropriate dosing for children is unknown |
| Rifapentine | Tablet (150 mg, film coated) | Adults | — | 10 mg/kg (continuation phase (600 mg) | — | — |
| | | Children | The drug is not approved for use in children | The drug is not approved for use in children | The drug is not approved for use in children | The drug is not approved for use in children |
| Pyrazinamide | Tablet (500 mg, scored) | Adults Children (max.) | See Table 4 15-30 mg/kg (2.0 g) | — — | See Table 4 50 mg/kg (2 g) | See Table 4 — |
| Ethambutol | Tablet (100 mg, 400 mg) | Adults Children§ (max.) | See Table 5 15-20 mg/kg daily (1.0 g) | — — | See Table 5 50 mg/kg (2.5 g) | See Table 5 — |
| Second-line drugs | | | | | | |
| Cyclosenine | Capsule (250 mg) | Adults (max.) | 10-15 mg/kg/d (1.0 g in two doses), usually 500-750 mg/d in two doses¶ | There are no data to support intermittant admisistration | There are no data to support intermittant administration | There are no data to support intermittant administration |
| | | Children (max.) | 10-15 mg/kg (1.0 g/d) | — | — | — |
| Ethionamide | Tablet (250 mg) | Adults* (max.) | 15-20 mg/kg/d (1.0 g/d), usually 500-750 mg/d in a single daily dose or two divided doses# | There are no data to support intermittent administration | There are no data to support intermittent administration | There are no data to support intermittent administration |
| | | Children (max.) | 15-20 mg/kg/d (1.0 g/d) | There are no data to support intermittent administration | There are no data to support intermittent administration | There are no data to support intermittent administration |

TABLE 3-continued

Doses of antituberculosis drugs for adults and children

| Drug | Preparation | Adults/children | Doses Daily | 11×/wk | 2×/wk | 3×/wk |
|---|---|---|---|---|---|---|
| Streptomycin | Aqueous solution (1-g vials) for intravenous or intramuscular administration | Adults (max.) Children (max.) | — 20-40 mg/kg/d (1 g) | ** — | ** 20 mg/kg | ** — |
| Amikacin/ kanamycin | Aqueous solution (500-mg and 1-g vials) for intravenous or intramuscular administration | Adults (max.) Children (max.) | — 15-30 mg/kg/d (1 g) intravenous or intramuscular as a single daily dose | ** — | ** 15-30 mg/kg | ** — |
| Capreomycin | Aqueous sulution (1-g vials) for intravenous or intramuscular administration | Adults (max.) Children (max.) | — 15-30 mg/kg/d (1 g) as a single daily dose | ** — | ** 15-30 mg/kg | ** — |
| p-Aminosalicylic acid (PAS) | Granules (4-g packets) can be mixed with food; tablets (500 mg) are still available in some countries, but not in the United States; a solution for intravenous administration is available in Europe | Adults Children | 8-12 g/d in two or three doses 200-300 mg/kg/d in two to four divided doses (10 g) | There are no data to support intermittent administration There are no data to suppport intermittent administration | There are no data to support intermittent administration There are no data to support intermittent administration | There are no data to support intermittent administration There are no data to support intermittent administration |
| Levofloxacin | Tablets (250 mg, 500 mg, 750 mg); aqueous solution (500-mg vials) for intravenous injection | Adults Children | 500-1,000 mg daily †† | There are no data to support intermittent administration †† | There are no data to support intermittent administration †† | There are no data to support intermittent administration †† |
| Moxifloxacin | Tablets (400 mg); aqueous solution (400 mg/250 ml) for intravenous injection | Adults Children | 400 mg daily ‡‡ | There are no data to support intermittent administration ‡‡ | There are no data to support intermittent administration ‡‡ | There are no data to support intermittent administration ‡‡ |
| Gatifloxacin | Tablets (400 mg); aqueous solution (200 mg/20 ml; 400 mg/40 ml) for intravenous injection | Adults Children | 400 mg daily §§ | There are no data to support intermittent administration §§ | There are no data to support intermittent administration §§ | There are no data to support intermittent administration §§ |

*Dose per weight is based on ideal body weight. Children weighing more than 40 kg should be dosed as adults.
†For purpose of this document adult dosing begins at age 15 years.
‡Dose may need to be adjusted when there is concomitant use of protease inhibitors or nonnucleoside reverse transcriptase inhibitors.
§The drug can likely be used safely in older children but should be used with caution in children less than 5 years of age, in whom visual acuity cannot be monitored. In younger children EMB at the dose of 15 mg/kg per day can be used if there is suspected or proven resistance to INH or RIF.
¶It should be noted that, although this is the dose recommended generally, most clinicians with experience with cycloserine indicate that it is unusual for patients to be able to tolerate this amount. Serum concentration measurements are often useful in determining the optimal dose for a given patient. The single dose can be given at bedtime or with the main meal.
**Dose: 15 mg/kg per day (1 g), and 10 mg/kg in persons more than 59 years of age (750 mg). Usual dose 750-1,000 mg administered intramuscularly or intravenously, given as a single dose 5-7 days/week and reduced to two or three times per week after the first 2-4 months or after culture conversion, depending on the efficacy of the other drugs in the regimen.
††The long-term (more than several weeks) use of levofloxacin in children and adolescents has not been approved because of concerns about effects on bone and cartilage growth. However, most experts agree that the drug should be considered for children with tuberculosis caused by organisms resistant to both INH and RIF. The optimal dose is not known.
‡‡The long-term (more than several weeks) use of moxifloxacin in children and adolescents has not been approved because of concerns about effects on bone and cartilage growth. The optimal dose is not known.
§§The long-term (more than several weeks) use of gatifloxacin in children and adolescents has not been approved because of concerns about effects on bone and cartilage grwoth. The optimal dose is not known.

TABLE 4

Suggested pyrazinamide doses, using whole tablets, for adults weighing 40-90 kg

| | Weight (kg)* | | |
|---|---|---|---|
| | 40-55 | 56-75 | 76-90 |
| Daily, mg (mg/kg) | 1,000 (18.2-25.0) | 1,500 (20.0-26.8) | 2,000† (22.2-26.3) |
| Thrice weekly, mg (mg/kg) | 1,500 (27.3-37.5) | 2,500 (33.3-44.6) | 3,000† (33.3-39.5) |
| Twice weekly, mg (mg/kg) | 2,000 (36.4-50.0) | 3,000 (40.0-53.6) | 4,000† (44.4-52.8) |

*Based on estimated lean body weight.
†Maximum dose regardless of weight.

TABLE 5

Suggested ethambutol doses, using whole tablets, for adults weighing 40-90 kg

| | Weight (kg)* | | |
|---|---|---|---|
| | 40-55 | 56-75 | 76-90 |
| Daily, mg (mg/kg) | 800 (14.5-20.0) | 1,200 (16.0-21.4) | 1,600† (17.8-21.1) |
| Thrice weekly, mg (mg/kg) | 1,200 (21.8-30.0) | 2,000 (26.7-35.7) | 2,400† (26.7-31.6) |
| Twice weekly, mg (mg/kg) | 2,000 (36.4-50.0) | 2,800 (37.3-50.0) | 4,000† (44.4-52.6) |

*Based on estimated lean body weight.
†Maximum dose regardless of weight.

The term "prodrug" refers to compounds which are drug precursors which, following administration and absorption, release the drug in vivo via some metabolic process. In general, a prodrug possesses less biological activity than its parent drug. A prodrug may also improve the physical properties of the parent drug and/or it may also improve overall drug efficacy, for example through the reduction of toxicity and unwanted effects of a drug by controlling its absorption, blood levels, metabolic distribution and cellular uptake.

The term "parent compound" or "parent drug" refers to the biologically active entity that is released via enzymatic action of a metabolic or a catabolic process, or via a chemical process following administration of the prodrug. The parent compound may also be the starting material for the preparation of its corresponding prodrug.

The monovalent cations defined by $M^+$ include ammonium, alkali metal ions such as sodium, lithium and potassium ions, dicyclohexylamine ion, and N-methyl-D-glucamine ion. The divalent cations defined by $D^{2+}$ include, alkaline earth metal ions such as aluminum, calcium and magnesium ions. Also included are amino acid cations such as ions of arginine, lysine, ornithine, and so forth. If $M^+$ is a monovalent cation, it is recognized that if the definition $2M^+$ is present, each of $M^+$ may be the same or different. In addition, it is similarly recognized that if the definition $2M^+$ is present, a divalent cation $D^{2+}$ may instead be present. Also, the basic nitrogen-containing groups may be quaternized with such agents as: lower alkyl halides, such as methyl, ethyl, propyl, and butyl chloride, bromides and iodides; dialkyl sulfates like dimethyl, diethyl, dibutyl; diamyl sulfates; long chain halides such as decyl, lauryl, myristyl and stearyl chlorides, bromides and iodides; aralkyl halides like benzyl bromide and others.

Various embodiments of the invention, include compounds or salts of formula (IB) as set forth below:

(1) compounds wherein X is
  (a) —PO(OH)O$^-$M$^+$;
  (b) —PO(O$^-$)$_2$.2M$^+$; or
  (c) —PO(O$^-$)$_2$.D$^{2+}$;
(2) compounds wherein M$^+$ is
  (a) Li$^+$, Na$^+$, K$^+$, N-methyl-D-glucamine, or N(R$^9$)$_4$$^+$; or
  (b) Na$^+$;
  (c) each R$^9$ is independently hydrogen or a C$_1$-C$_4$ alkyl group;
(3) compounds wherein D$^{2+}$ is
  (a) Mg$^{2+}$, Ca$^{2+}$, and Ba$^{2+}$; or
  (b) Ca$^{2+}$;
(4) the compound (R)-2-(5-(2-(3-ethylureido)-6-fluoro-7-(tetrahydrofuran-2-yl)-1H-benzo[d]imidazol-5-yl)pyrimidin-2-yl)propan-2-yl phosphate; and
(5) the compound disodium (R)-2-(5-(2-(3-ethylureido)-6-fluoro-7-(tetrahydrofuran-2-yl)-1H-benzo[d]imidazol-5-yl)pyrimidin-2-yl)propan-2-yl phosphate.

It is understood that various alternative embodiments of the compounds or salts of formula (IB) can be selected by requiring one or more of the alternate embodiments listed in (1) through (3) above. For example, further embodiments of the invention can be obtained by combining (1)(a) and (2)(a); (1)(a) and (2)(b); (1)(c) and (3)(a); (1)(c) and (3)(b); (1)(b) and (2)(a); (1)(b) and (2)(b); and the like.

The prodrugs of the present invention are characterized by unexpectedly high aqueous solubility. This solubility facilitates administration of higher doses of the prodrug, resulting in a greater drug load per unit dosage.

A "pharmaceutically acceptable derivative or prodrug" means any pharmaceutically acceptable salt, ester, salt of an ester or other derivative of a compound of this invention which, upon administration to a recipient, is capable of providing, either directly or indirectly, a compound of this invention or an inhibitorily active metabolite or residue thereof. Particularly favored derivatives or prodrugs are those that increase the bioavailability of the compounds of this invention when such compounds are administered to a mammal (e.g., by allowing an orally administered compound to be more readily absorbed into the blood) or which enhance delivery of the parent compound to a biological compartment (e.g., the brain or lymphatic system) relative to the parent species.

Pharmaceutically acceptable prodrugs of the compounds of this invention include, without limitation, esters, amino acid esters, phosphate esters, metal salts and sulfonate esters.

Pharmaceutically acceptable salts of the compounds of this invention include those derived from pharmaceutically acceptable inorganic and organic acids and bases. Examples of suitable acid salts include acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, formate, fumarate, glucoheptanoate, glycerophosphate, glycolate, hemisulfate, heptanoate, hexanoate, hydrochloride, hydrobromide, hydroiodide, 2-hydroxyethanesulfonate, lactate, maleate, malonate, methanesulfonate, 2-naphthalenesulfonate, nicotinate, nitrate, palmoate, pectinate, persulfate, 3-phenylpropionate, phosphate, picrate, pivalate, propionate, salicylate, succinate, sulfate, tartrate, thiocyanate, tosylate and undecanoate. Other acids, such as oxalic, while not in themselves pharmaceutically acceptable, may be employed in the preparation of salts useful as intermediates in obtaining the compounds of the invention and their pharmaceutically acceptable acid addition salts.

Salts derived from appropriate bases include alkali metal (e.g., sodium and potassium), alkaline earth metal (e.g., magnesium), ammonium and N$^+$(C$_{1-4}$ alkyl)$_4$ salts. This invention also envisions the quaternization of any basic nitrogen-containing groups of the compounds disclosed herein. Water or oil-soluble or dispersible products may be obtained by such quaternization.

Pharmaceutical compositions of this invention comprise a compound of formula (I) or a pharmaceutically acceptable salt thereof and a pharmaceutically acceptable carrier. Such compositions may optionally comprise an additional therapeutic agent. Such agents include, but are not limited to, an antibiotic, an anti-inflammatory agent, a matrix metalloprotease inhibitor, a lipoxygenase inhibitor, a cytokine antagonist, an immunosuppressant, an anti-cancer agent, an antiviral agent, a cytokine, a growth factor, an immunomodulator, a prostaglandin or an anti-vascular hyperproliferation compound.

The term "pharmaceutically acceptable carrier" refers to a non-toxic carrier that may be administered to a patient, together with a compound of this invention, and which does not destroy the pharmacological activity thereof.

Pharmaceutically acceptable carriers that may be used in the pharmaceutical compositions of this invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, wool fat and self-emulsifying drug delivery systems (SEDDS) such as alpha-tocopherol, polyethyleneglycol 1000 succinate, or other similar polymeric delivery matrices.

The term "pharmaceutically effective amount" or "therapeutically effective amount" refers to an amount effective in treating or ameliorating a bacterial infection in a patient. The term "prophylactically effective amount" refers to an amount effective in preventing or substantially lessening a bacterial infection in a patient.

The following definitions describe terms and abbreviations used herein:
Ac acetyl
Bu butyl
Et ethyl
Ph phenyl
Me methyl
THF tetrahydrofuran
DCM dichloromethane
$CH_2Cl_2$ dichloromethane
EtOAc ethyl acetate
$CH_3CN$ acetonitrile
EtOH ethanol
$Et_2O$ diethyl ether
MeOH methanol
MTBE methyl tert-butyl ether
DMF N,N-dimethylformamide
DMA N,N-dimethylacetamide
DMSO dimethyl sulfoxide
HOAc acetic acid
TEA triethylamine
TFA trifluoroacetic acid
TFAA trifluoroacetic anhydride
$Et_3N$ triethylamine
DIPEA diisopropylethylamine
DIEA diisopropylethylamine
$K_2CO_3$ potassium carbonate
$Na_2CO_3$ sodium carbonate
$Na_2S_2O_3$ sodium thiosulfate
$Cs_2CO_3$ cesium carbonate
$NaHCO_3$ sodium bicarbonate
NaOH sodium hydroxide
$Na_2SO_4$ sodium sulfate
$MgSO_4$ magnesium sulfate
$K_3PO_4$ potassium phosphate
$NH_4Cl$ ammonium chloride
LC/MS liquid chromatography/mass spectra
GCMS gas chromatography mass spectra
HPLC high performance liquid chromatography
GC gas chromatography
LC liquid chromatography
IC ion chromatography
IM intramuscular
CFU/cfu colony forming units
MIC minimum inhibitory concentration
Hr or h hours
atm atmospheres
rt or RT room temperature
TLC thin layer chromatography
HCl hydrochloric acid
$H_2O$ water
EtNCO ethyl isocyanate
Pd/C palladium on carbon
NaOAc sodium acetate
$H_2SO_4$ sulfuric acid
$N_2$ nitrogen gas
$H_2$ hydrogen gas
n-BuLi n-butyl lithium
DI de-ionized
$Pd(OAc)_2$ palladium(II)acetate
$PPh_3$ triphenylphosphine
i-PrOH isopropyl alcohol
NBS N-bromosuccinimide
$Pd[(Ph_3)P]_4$ tetrakis(triphenylphosphine)palladium(0)
PTFE polytetrafluoroethylene
rpm revolutions per minute
SM starting material
Equiv. equivalents
$^1$H-NMR proton nuclear magnetic resonance
HPMCAS hydroxypropylmethylcellulose acetate
PVP polyvinylpyrrolidone
EDTA ethylenediaminetetraacetic acid
K2EDTA dibasic potassium ethylenediaminetetraacetate
mCPBA meta-chloroperoxybenzoic acid
aq aqueous
$Boc_2O$ di-tert-butyl dicarbonate
DMAP N,N-dimethylaminopyridine
mL milliliters
L liters
mol moles
g grams
LCMS liquid chromatography-mass spectrometry
MHz megahertz
$CDCl_3$ deuterochloroform
$NEt_3$ triethylamine
mmol millimoles
psi pounds per square inch
iPrOH isopropylalcohol
ppm parts per million
$NH_4NO_3$ ammonium nitrate
Hz hertz
$Pd(dppf)Cl_2$ [1,1'-Bis(diphenylphosphino)ferrocene]dichloropalladium(II)
L liters
MeOD deutero-methanol
$CD_3OD$ deutero-methanol
ee enantiomeric excess
min minutes
Bn benzyl
RBF round-bottom flask
MeCN acetonitrile
PES polyethersulfone
mm millimeters
μm micrometers
M molar
N normal
Boc tert-butoxycarbonyl
ESMS electrospray mass spectrometry
CV column volume
$D_2O$ deuterium oxide
$NH_3$ ammonia
OBD optimum bed density
mg milligrams
CLSI Clinical and Laboratory Standards Institute
ATCC American Type Culture Collection
MHII Mueller Hinton II
μm microliters
WT wild type
CGSC Coli Genetic Stock Center
MS mass spectrometry
IS internal standard
APCI atmospheric pressure chemical ionization
MRM multiple reaction monitoring
m/z mass-to-charge ratio
LLOQ lower limit of quantitation ng nanograms
UV ultraviolet
SD standard deviation
% CV coefficient of variation
PO perioral
MC microcrystalline cellulose
EDTA ethylenediaminetetraacetic acid or ethylenediaminetetraacetate
PK pharmacokinetic
PBS phosphate buffer saline
IV intravenous
D5W 5% dextrose in water solution
HPMC-AS hydroxypropyl methylcellulose acetyl succinate
PVP polyvinylprrolidone
CAPT captisol
ATP adenosine triphosphate
ADP adenosine diphosphate
NADH nicotinamide adenine dinucleotide (reduced form)
NAD+ nicotinamide adenine dinucleotide (oxidized form)
TRIS tris(hydroxymethyl)aminomethane
mM millimolar
$MgCl_2$ magnesium chloride
KCl potassium chloride
μM micromolar
DTT dithiothreitol
nM nanomolar
dissociation constant
$IC_{50}$ half maximal inhibitory concentration
μg micrograms
BSA bovine serum albumin
LDH lactate dehydrogenase
PVDF polyvinylidene fluoride
PBS phosphate buffered saline
BSL3 Biosafety Level 3
AcN acetonitrile
$V_{MAX}$ the maximum initial velocity or rate of a reaction

EXAMPLE 1

Preparation of 2-(2-nitrophenyl)-2,5-dihydrofuran and 2-(2-nitrophenyl)-2,3-dihydrofuran (3a&3b)

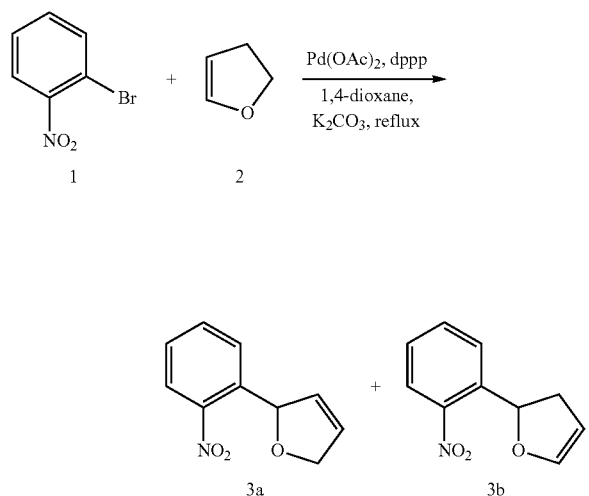

Mixed 1-bromo-2-nitro-benzene (1) (600 g, 99%, 2.941 mol, Alfa Aesar A11686), 1,3-bis(diphenylphosphino)propane (62.50 g, 97%, 147.0 mmol, Alfa Aesar A12931), 1,4-dioxane (2.970 L, Sigma-Aldrich 360481), potassium carbonate (812.9 g, 5.882 mol, JT-Baker 301201), and 2,3-dihydrofuran (2) (1.041 kg, 99%, 1.124 L, 14.70 mol, Aldrich 200018). A stream of nitrogen was bubbled through the stirring mixture for 4 hrs, followed by addition of palladium (II) acetate (16.51 g, 73.52 mmol, Strem 461780) and continuation of deoxygenation for another 10 minutes. The reaction mixture was stirred at reflux under nitrogen overnight (NMR of a worked-up aliquot showed complete consumption of arylbromide). It was allowed to cool, diluted with hexane (1 L), filtered through a short plug of Florisil® (500 g, ~200 mesh), and eluted with EtOAc. The filtrate was concentrated under reduced pressure (2-(2-nitrophenyl)-2,3-dihydrofuran is volatile under high vacuum and may be somewhat unstable at room temperature) giving a mixture of (3a) and (3b) as a dark brown oil (654.0 g). The crude material was stored in the refrigerator and carried forward without further purification.

EXAMPLE 2

Preparation of 2-tetrahydrofuran-2-yl-aniline (4)

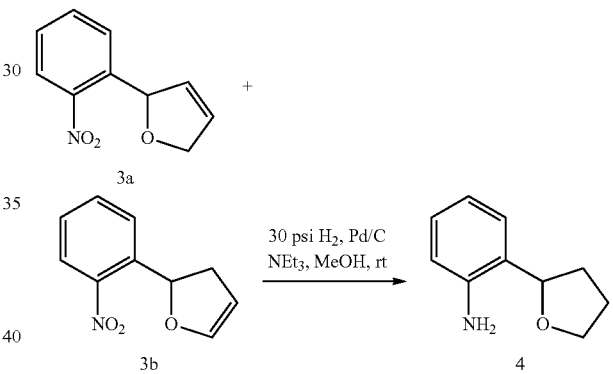

Placed 5% palladium on carbon (16.3 g, 50% wet, 3.83 mmol, Aldrich 330116) in a Parr bottle under nitrogen, followed by MeOH (100 mL, JT-Baker 909333). Added the crude mixture of 2-(2-nitrophenyl)-2,5-dihydrofuran and 2-(2-nitrophenyl)-2,3-dihydrofuran (3a&3b)) (163 g) dissolved in MeOH (389 mL), followed by $NEt_3$ (237.6 mL, 1.705 mol, Sigma-Aldrich 471283). Placed the vessel on a Parr shaker and saturated with $H_2$. Added 30 psi $H_2$ and shook until consumption complete (LCMS and NMR showed complete reaction). The reaction mixture was purged with nitrogen, filtered through Celite™ and rinsed with EtOAc. The filtrate was concentrated on a rotary evaporator giving a brown oil. Repeated the reaction three more times on the same scale and the batches were combined for purification. The crude product was vacuum distilled (ca. 15 ton) collecting the distillate at 108-129° C. to give (4) as a clear faint yellow oil (427.9 g, average yield was 84%; 98% GCMS purity). LCMS (C18 column eluting with 10-90% $CH_3CN$/water gradient over 5 minutes with formic acid modifier) M+1: 163.95 (1.46 min). $^1$H NMR (300 MHz, $CDCl_3$). δ 7.15-7.04 (m, 2H), 6.77-6.62 (m, 2H), 4.85-4.77 (m, 1H), 4.18 (s, 2H), 4.12-4.02 (m, 1H), 3.94-3.85 (m, 1H), 2.25-1.95 (m, 4H) ppm.

EXAMPLE 2a

Preparation of (R)-2-(tetrahydrofuran-2-yl)aniline (4a)

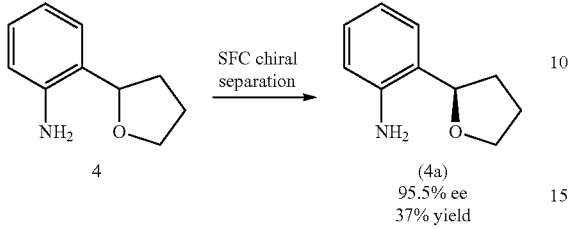

(4a)
95.5% ee
37% yield

Dissolved 33 g of compound (4) into MeOH (265 ml) which resulted in a concentration of approximately 125 mg/ml. The mixture was filtered through a 0.2 micron membrane filter then chromatographed on a ChiralPak® IC column (30 mm×150 mm, column temp 35° C., Chiral Technologies) at 100 bar using a Berger multigram supercritical fluid chromatographic system. Mobile phase was (90:10) $CO_2$:$CH_3OH$ eluting at 350 ml/min with UV monitoring at 220 nanometers. Obtained 15.64 g of desired product (4a) as a green oil. Analytical SFC ([90:10] $CO_2$:$CH_3OH$, at 5 ml/min on a ChiralPak IC column (4.6×100 mm) held at 35° C. and run at 100 bar pressure with UV monitoring at 220 nm) showed 95.5% ee with 95% overall purity.

EXAMPLE 3

Preparation of 4-bromo-2-tetrahydrofuran-2-yl-aniline (5)

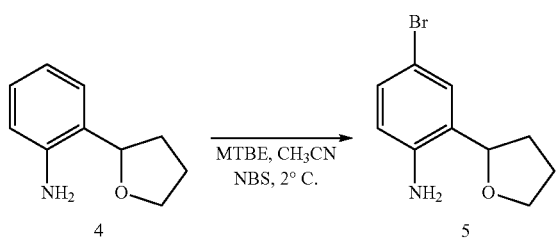 [SMILES: Nc1ccccc1C1CCCO1 ; Nc1ccc(Br)cc1C1CCCO1]

To a stirring solution of 2-tetrahydrofuran-2-yl-aniline (4) (53.45 g, 327.5 mmol) in methyl tert-butyl ether (MTBE, 641.4 mL) and acetonitrile (213.8 mL) cooled to 2° C. was added N-bromosuccinimide (58.88 g, 99%, 327.5 mmol, Aldrich B81255) in 4 portions maintaining internal temperature below about 8° C. The reaction mixture was stirred while cooling with an ice-water bath for 30 minutes (NMR of a worked-up aliquot showed complete consumption of starting material). Added aqueous 1 N $Na_2S_2O_3$ (330 mL), removed the cold bath and stirred for 20 minutes. The mixture was diluted with EtOAc and the layers were separated. The organic phase was washed with saturated aqueous $NaHCO_3$ (2×), water, brine, dried over $MgSO_4$, filtered through a short plug of silica, eluted with EtOAc, and concentrated under reduced pressure to give (5) as a very dark amber oil (82.25 g, 77-94% HPLC purity). Carried forward without further purification. LCMS (C18 column eluting with 10-90% $CH_3CN$/water gradient over 5 minutes with formic acid modifier) M+1: 242.10 (2.89 min). $^1$H NMR (300 MHz, $CDCl_3$) δ 7.22 (d, J=2.3 Hz, 1H), 7.16 (dd, J =8.4, 2.3 Hz, 1H), 6.54 (d, J=8.4 Hz, 1H), 4.79-4.73 (m, 1H), 4.15 (s, 2H), 4.10-4.01 (m, 1H), 3.93-3.85 (m, 1H), 2.26-2.13 (m, 1H), 2.12-1.97 (m, 3H) ppm.

EXAMPLE 4

Preparation of N-(4-bromo-2-nitro-6-tetrahydrofuran-2-yl-phenyl)-2,2,2-trifluoro-acetamide (6)

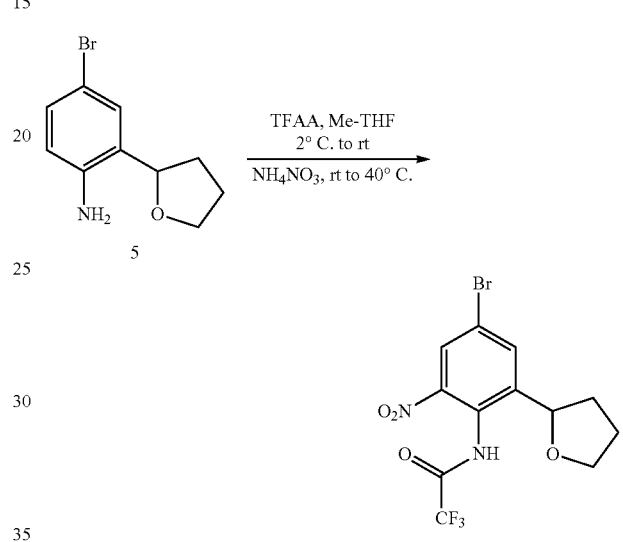

To trifluoroacetic anhydride (455.3 mL, 3.275 mol, Sigma-Aldrich 106232) stirring at 2° C. was slowly added 4-bromo-2-tetrahydrofuran-2-yl-aniline (5) (79.29 g, 327.5 mmol) as a thick oil via addition funnel over 15 minutes (reaction temperature rose to 14° C.). The remaining oil was rinsed into the reaction mixture with anhydrous 2-methyl-tetrahydrofuran (39.6 mL, Sigma-Aldrich 414247). The cold bath was removed and ammonium nitrate (34.08 g, 425.8 mmol, Aldrich 467758) was added. The reaction temperature rose to 40° C. over about 30 minutes at which time a cold water bath was used to control the exotherm and bring the reaction to room temperature. The cold bath was then removed and stirring continued for another 40 minutes (HPLC showed very little remaining un-nitrated material). The reaction mixture was slowly poured into a stirring mixture of crushed ice (800 g). The solid precipitate was collected by filtration, washed with water, saturated aqueous $NaHCO_3$ (to pH 8), water again, and hexane. The wet solid was dried first in a convection oven at 50° C. for several hours and then under reduced pressure in an oven at 40° C. overnight giving (6) as a light brown solid (77.86 g, 62% yield; 98% HPLC purity). LCMS (C18 column eluting with 10-90% $CH_3CN$/water gradient over 5 minutes with formic acid modifier) M+1: 383.19 (3.27 min). $^1$H NMR (300 MHz, $CDCl_3$) δ 9.81 (s, 1H), 8.08 (d, J=2.2 Hz, 1H), 7.73 (d, J=2.2 Hz, 1H), 4.88 (dd, J=9.0, 6.5 Hz, 1H), 4.17-4.08 (m, 1H), 4.03-3.95 (m, 1H), 2.45-2.34 (m, 1H), 2.17-2.06 (m, 2H), 1.96-1.83 (m, 1H) ppm.

EXAMPLE 5

Preparation of 4-bromo-2-nitro-6-tetrahydrofuran-2-yl-aniline (6a)

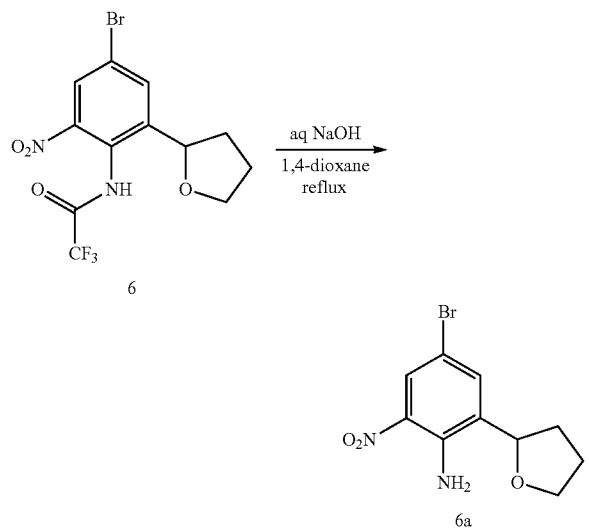

Dissolved N-(4-bromo-2-nitro-6-tetrahydrofuran-2-yl-phenyl)-2,2,2-trifluoro-acetamide (6) (54.00 g, 140.9 mmol) in 1,4-dioxane (162 mL) and added aqueous 6 M NaOH (70.45 mL, 422.7 mmol, JT-Baker 567202). The reaction mixture was stirred at reflux for 2 days (HPLC showed complete conversion), allowed to cool, diluted with MTBE (800 mL), washed with water (2×200 mL), saturated aqueous NH$_4$Cl, water and brine. The mixture was dried over MgSO$_4$, filtered, and concentrated under reduced pressure to give (6a) as a dark amber oil (40.96 g, 93% yield; overall 92% HPLC plus NMR purity). LCMS (C18 column eluting with 10-90% MeOH/water gradient from 3-5 minutes with formic acid modifier) M+1: 287.28 (3.44 min). $^1$H NMR (300 MHz, CDCl$_3$) δ 8.24 (d, J=2.4 Hz, 1H), 7.41 (d, J=2.3 Hz, 1H), 6.91 (s, 2H), 4.80 (t, J=7.2 Hz, 1H), 4.14-4.05 (m, 1H), 3.98-3.90 (m, 1H), 2.36-2.19 (m, 1H), 2.15-2.01 (m, 3H) ppm.

EXAMPLE 6

Preparation of 2-[5-(4-amino-3-nitro-5-tetrahydrofuran-2-yl-phenyl)pyrimidin-2-yl]propan-2-ol (8)

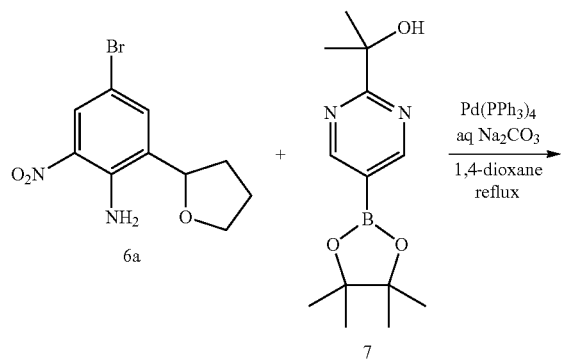

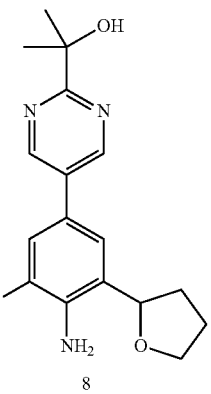

Mixed 4-bromo-2-nitro-6-tetrahydrofuran-2-yl-aniline (6a) (40.40 g, 92%, 129.5 mmol), 1,4-dioxane (260 mL, Sigma-Aldrich 360481), 2-[5-(4,4,5,5-tetramethyl-1,3,2-dioxaborolan-2-yl)pyrimidin-2-yl]propan-2-ol (7) (41.05 g, 155.4 mmol), and aqueous 2.7 M Na$_2$CO$_3$ (143.9 mL, 388.5 mmol). A stream of nitrogen was bubbled through the stirring mixture for 1 hr, followed by addition of tetrakis(triphenylphosphine)palladium (0) (7.48 g, 6.47 mmol, Strem 462150). The reaction mixture was stirred at reflux for 2 hrs (HPLC showed complete reaction), allowed to cool, diluted with EtOAc, washed with water, saturated aqueous NH$_4$Cl, brine, dried over MgSO$_4$, and filtered through a short plug of Florisil® eluting with EtOAc. The filtrate was concentrated under reduced pressure giving a dark brown oil. Dissolved in CH$_2$Cl$_2$ and eluted through a short plug of silica gel with CH$_2$Cl$_2$ and then EtOAc. The desired fraction was concentrated on a rotary evaporator until a precipitate formed giving a thick brown slurry, which was triturated with MTBE. The solid was collected by filtration, washed with MTBE, and dried under high vacuum giving (8) as a yellow solid (35.14 g, 99+% HPLC purity). LCMS (C18 column eluting with 10-90% CH$_3$CN/water gradient over 5 minutes with formic acid modifier) M+1: 345.00 (2.69 min). $^1$H NMR (300 MHz, CDCl$_3$) δ 8.88 (s, 2H), 8.36 (d, J=2.2 Hz, 1H), 7.56 (d, J=2.1 Hz, 1H), 7.09 (s, 2H), 4.92 (t, J=7.2 Hz, 1H), 4.62 (s, 1H), 4.20-4.11 (m, 1H), 4.03-3.94 (m, 1H), 2.39-2.26 (m, 1H), 2.23-2.08 (m, 3H), 1.64 (s, 6H) ppm. The filtrate was further concentrated and purified by ISCO silica gel chromatography eluting with 0 to 80% EtOAc/hexane giving a second crop of product (8) as an amber solid (4.46 g, 88% overall yield; 88% HPLC purity.

EXAMPLE 7

Alternate preparation of 2-[5-(4-amino-3-nitro-5-tetrahydrofuran-2-yl-phenyl)pyrimidin-2-yl]propan-2-ol (8)

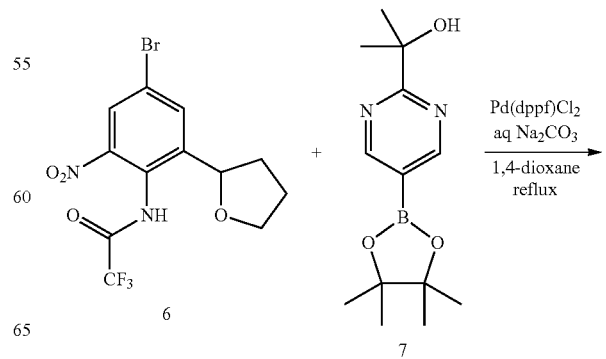

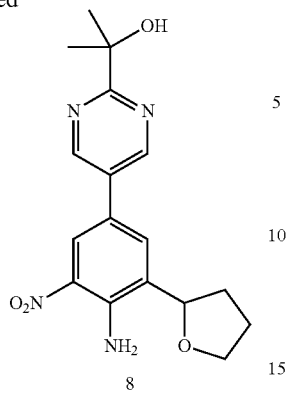

8

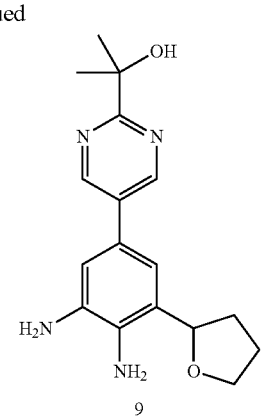

9

Mixed N-(4-bromo-2-nitro-6-tetrahydrofuran-2-yl-phenyl)-2,2,2-trifluoro-acetamide (6) (19.00 g, 49.59 mmol), 2-[5-(4,4,5,5-tetramethyl-1,3,2-dioxaborolan-2-yl)pyrimidin-2-yl]propan-2-ol (7) (14.41 g, 54.55 mmol), aqueous 2.7 M sodium carbonate (73.48 mL, 198.4 mmol), and 1,4-dioxane (190 mL, Sigma-Aldrich 360481). A stream of nitrogen was bubbled through the stirring mixture for 40 minutes, followed by addition of 1,1'-bis(diphenylphosphino)ferrocene dichloropalladium dichloromethane adduct (2.025 g, 2.480 mmol, Strem 460450). The reaction mixture was stirred at reflux under $N_2$ for 7 hrs, added another 50 mL of saturated aqueous sodium carbonate, and refluxed for another 16 hrs. The mixture was allowed to cool, then diluted with EtOAc (500 mL) and water (200 mL). The layers were separated and the aqueous phase extracted with EtOAc (200 mL). The combined organic phase was washed with water (500 mL), brine (500 mL), dried over $Na_2SO_4$, filtered through a Florisil® plug, and concentrated on a rotary evaporator to give crude (8) as an orange oil. Crude product was purified by ISCO silica gel chromatography eluting with 20-90% EtOAc/hexane to give (8) as an orange solid (15.00 g, 87% yield; 81-88% purity). LCMS (C18 column eluting with 10-90% $CH_3CN$/water gradient over 5 minutes with formic acid modifier) M+1: 345.35 (2.68 min). $^1$H NMR (300 MHz, CDCl$_3$) δ 8.88 (s, 2H), 8.36 (d, J=2.2 Hz, 1H), 7.56 (d, J=2.1 Hz, 1H), 7.09 (s, 2H), 4.92 (t, J=7.2 Hz, 1H), 4.62 (s, 1H), 4.20-4.11 (m, 1H), 4.03-3.94 (m, 1H), 2.39-2.26 (m, 1H), 2.23-2.08 (m, 3H), 1.64 (s, 6H) ppm.

EXAMPLE 8

Preparation of 2-[5-(3,4-diamino-5-tetrahydrofuran-2-yl-phenyl)pyrimidin-2-yl]propan-2-ol (9)

To a suspension of 2-[5-(4-amino-3-nitro-5-tetrahydrofuran-2-yl-phenyl)pyrimidin-2-yl]propan-2-ol (8) (30.10 g, 87.41 mmol) and THF (90 mL) in a Parr bottle under nitrogen was added a slurry of 5% palladium on carbon (3.01 g, 50% wet, 0.707 mmol, Aldrich 330116) in MeOH (90 mL, JT-Baker 909333), followed by NEt$_3$ (24.37 mL, 174.8 mmol, Sigma-Aldrich 471283). Placed the vessel on a Parr shaker and saturated with $H_2$. Added 45 psi $H_2$ and shook until consumption was complete (HPLC showed complete conversion). The reaction mixture was purged with nitrogen, filtered through Celite™ and rinsed with EtOAc. The filtrate was re-filtered through a 0.5 micron glass fiber filter paper sandwiched between two P5 papers, and concentrated under reduced pressure giving (9) as a light brown foam (28.96 g, 98% yield; 93% NMR purity). LCMS (C18 column eluting with 10-90% $CH_3CN$/water gradient over 5 minutes with formic acid modifier) M+1: 315.32 (1.54 min). $^1$H NMR (300 MHz, CDCl$_3$) δ 8.83 (s, 2H), 6.92 (d, J=1.8 Hz, 1H), 6.88 (d, J=1.8 Hz, 1H), 4.90 (dd, J=7.9, 6.2 Hz, 1H), 4.72 (s, 1H), 4.18 (s, 2H), 4.17-4.08 (m, 1H), 3.99-3.89 (m, 1H), 3.46 (s, 2H), 2.34-2.19 (m, 1H), 2.17-2.05 (m, 3H), 1.63 (s, 6H) ppm.

EXAMPLE 9

Preparation of 1-ethyl-3-[5-[2-(1-hydroxy-1-methylethyl)pyrimidin-5-yl]-7-tetrahydrofuran-2-yl-1H-benzimidazol-2-yl]urea (11)

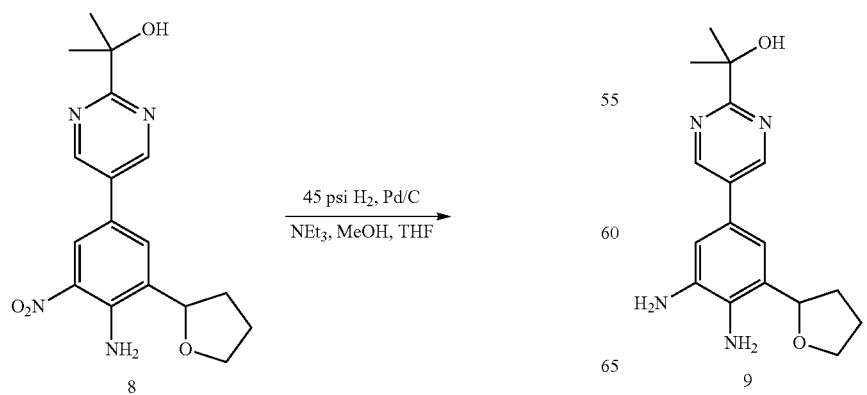

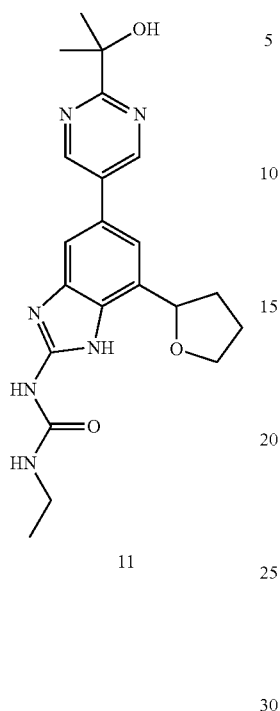

11

EXAMPLE 10

Chiral chromatographic isolation of 1-ethyl-3-[5-[2-(1-hydroxy-1-methyl-ethyl)pyrimidin-5-yl]-7-[(2R)-tetrahydrofuran-2-yl]-1H-benzimidazol-2-yl]urea (12)

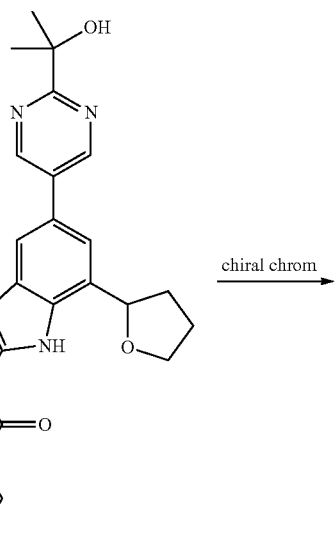

11

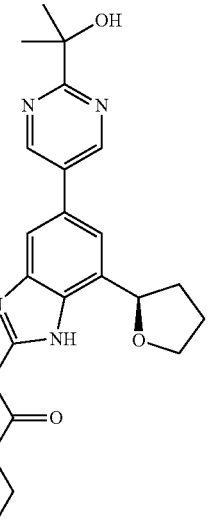

12

To a stirring solution of 2-[5-(3,4-diamino-5-tetrahydrofuran-2-yl-phenyl)pyrimidin-2-yl]propan-2-ol (9) (32.10 g, 102.1 mmol) in 1,4-dioxane (160.5 mL, Sigma-Aldrich 360481) was added pH 3.5 buffer (240.8 mL), prepared by dissolving NaOAc trihydrate (34.5 g) in 1N aqueous $H_2SO_4$ (240 mL). Added 1-ethyl-3-(N-(ethylcarbamoyl)-C-methyl-sulfanyl-carbonimidoyl)urea (10) (28.46 g, 122.5 mmol, CB Research and Development) and stirred at reflux overnight (HPLC showed 99% consumption of starting diamine). The reaction mixture was cooled to room temperature and poured portion-wise (frothing) into a stirring solution of aqueous saturated $NaHCO_3$ (480 mL) and water (120 mL) giving pH 8-9. This was stirred for 30 minutes, the solid was collected by filtration, washed copiously with water to neutral pH, and then more sparingly with EtOH. The solid was dried under reduced pressure giving (11) as an off-white solid (34.48 g, 82% yield; 99.4% HPLC purity). LCMS (C18 column eluting with 10-90% $CH_3CN$/water gradient over 5 minutes with formic acid modifier) M+1: 411.41 (1.73 min). $^1$H NMR (300 MHz, MeOD) δ 9.02 (s, 2H), 7.62 (s, 1H), 7.37 (s, 1H), 5.31 (s, 1H), 4.23 (dd, J=14.5, 7.3 Hz, 1H), 4.01 (dd, J=15.0, 7.1 Hz, 1H), 3.38-3.28 (m, 2H), 2.58-2.46 (m, 1H), 2.16-2.05 (m, 2H), 2.02-1.88 (m, 1H), 1.63 (s, 6H), 1.22 (t, J=7.2 Hz, 3H) ppm.

A racemic sample of 1-ethyl-3-[5-[2-(1-hydroxy-1-methyl-ethyl)pyrimidin-5-yl]-7-tetrahydrofuran-2-yl-1H-benzimidazol-2-yl]urea (11) (24.60 g) was resolved on a CHIRALPAK® IC® column (by Chiral Technologies) eluting with DCM/MeOH/TEA (60/40/0.1) at 35° C. giving the desired enantiomer (12) as a white solid (11.35 g, 45% yield; 99+% HPLC purity, 99+% ee). Analytical chiral HPLC retention time was 6.2 min (CHIRALPAK® IC® 4.6×250 mm column, 1 mL/min flow rate, 30° C.).

The structure and absolute stereochemistry of 12 were confirmed by single-crystal x-ray diffraction analysis. Single crystal diffraction data were acquired on a Bruker Apex II diffractometer equipped with sealed tube Cu K-alpha source (Cu Kα radiation, γ=1.54178 Å) and an Apex II CCD detector. A crystal with dimensions of ½×0.05×0.05 mm was selected, cleaned using mineral oil, mounted on a MicroMount and centered on a Bruker APEXII system. Three batches of 40 frames separated in reciprocal space were obtained to provide an orientation matrix and initial cell parameters. Final cell parameters were obtained and refined after data collection was completed based on the full data set. Based on systematic absences and intensities statistics the structure was solved and refined in acentric $P2_1$ space group.

A diffraction data set of reciprocal space was obtained to a resolution of 0.9 Å using 0.5° steps using 60 s exposure for each frame. Data were collected at 100 (2) K. Integration of intensities and refinement of cell parameters were accomplished using APEXII software. Observation of the crystal after data collection showed no signs of decomposition. As shown in FIG. 1, there are two symmetry independent molecules in the structure and both symmetry independent molecules are R isomers.

The data were collected, refined and reduced using the Apex II software. The structure was solved using the SHELXS97 (Sheldrick, 1990); program(s) and the structure refined using the SHELXL97 (Sheldrick, 1997) program. The crystal shows monoclinic cell with $P2_1$ space group. The lattice parameters are a=9.8423(4) Å, b=10.8426(3) Å, c=19.4441 (7) Å, β=102.966(3)°. Volume=2022.09(12) Å$^3$.

EXAMPLE 11

Preparation of the methanesulfonic acid salt of 1-ethyl-3-[5-[2-(1-hydroxy-1-methyl-ethyl)pyrimidin-5-yl]-7-[(2R)-tetrahydrofuran-2-yl]-1H-benzimidazol-2-yl]urea (13)

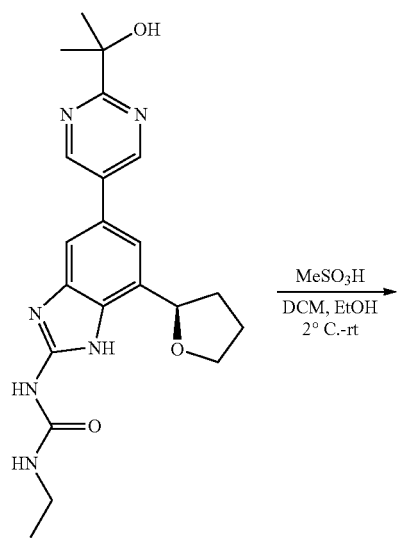

12

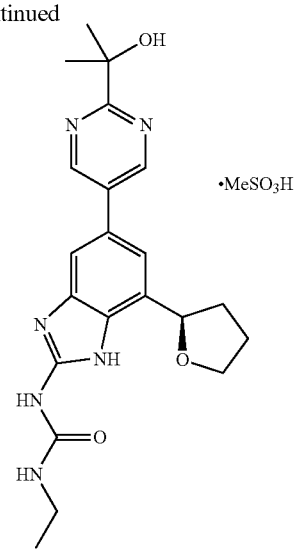

13

A stirring suspension of 1-ethyl-3-[5-[2-(1-hydroxy-1-methyl-ethyl)pyrimidin-5-yl]-7-[(2R)-tetrahydrofuran-2-yl]-1H-benzimidazol-2-yl]urea (12) (9.32 g, 22.71 mmol) in absolute ethanol (93.2 mL) was cooled with an ice-water bath. Added methanesulfonic acid (1.548 mL, 23.85 mmol, Sigma-Aldrich 471356), removed cold bath and stirred at room temperature for 20 minutes. It was concentrated on a rotary evaporator at 35° C. to a thick slurry, diluted with EtOAc, collected the solid by filtration, washed with EtOAc, and dried under reduced pressure giving an initial crop of (13) as a white solid (8.10 g). The filtrate was concentrated on a rotavap giving a yellowish glassy foam, which was dissolved in EtOH, concentrated to a solid slurry, triturated with EtOAc/Et$_2$O, and collected by filtration. The solid was washed with EtOAc/Et$_2$O, combined with the first crop, and dried under reduced pressure giving (13) as a white solid (9.89 g, 86% yield; 99+% HPLC purity, 99+% ee).

Analytical chiral HPLC shows one enantiomer with retention time of 6.3 min eluting with DCM/MeOH/TEA (60/40/0.1) on a CHIRALPAK® IC® 4.6×250 mm column with 1 mL/min flow rate at 30° C. LCMS (C18 column eluting with 10-90% CH$_3$CN/water gradient over 5 minutes with formic acid modifier) M+1: 411.53 (174 min). $^1$H NMR (300 MHz, MeOD) δ 9.07 (s, 2H), 7.79 (s, 1H), 7.62 (s, 1H), 5.30 (t, J=7.3 Hz, 1H), 4.24 (dd, J=14.6, 7.3 Hz, 1H), 4.04 (dd, J=15.0, 7.6 Hz, 1H), 3.40-3.30 (m, 2H), 2.72 (s, 3H), 2.65-2.54 (m, 1H), 2.20-2.07 (m, 2H), 2.04-1.90 (m, 1H), 1.64 (s, 6H), 1.23 (t, J=7.2 Hz, 3H) ppm.

EXAMPLE 12

Preparation of 2-(2-fluoro-6-nitro-phenyl)-2,3-dihydrofuran (15A) and 2-(2-fluoro-6-nitro-phenyl)-2,5-dihydrofuran (15B)

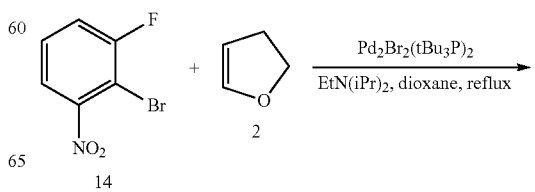

14

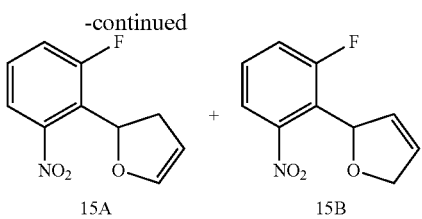

15A 15B

2-Bromo-1-fluoro-3-nitro-benzene (14) (200.3 g, 98%, 892.3 mmol, Bosche F6657), 1,4-dioxane (981.5 mL, Sigma-Aldrich 360481), and 2,3-dihydrofuran (2) (341.1 mL, 99%, 4.462 mol, Aldrich 200018) were charged in a reaction flask, followed by N,N-diisopropylethylamine (155.4 mL, 892.3 mmol, Sigma-Aldrich 550043) and bromo (tri-tert-butylphosphine)palladium(I) dimer (6.936 g, 8.923 mmol, Johnson Matthey C4099). The mixture was stirred at reflux for 2 hrs (HPLC showed 98% consumption of starting arylbromide). It was allowed to cool, the precipitate was removed by filtration, rinsed with EtOAc, and the filtrate concentrated in vacuo to a dark reddish brown semi-solid oil. This was dissolved in $CH_2Cl_2$, eluted through a plug of silica with $CH_2Cl_2$, and concentrated in vacuo giving a mixture of 15A and 15B as a dark amber oil (291.3 g). The crude product was carried forward without further purification. The major product was 2-(2-fluoro-6-nitrophenyl)-2, 3-dihydrofuran (15A) (96%): LCMS (C18 column eluting with 10-90% $CH_3CN$/ water gradient over 5 minutes with formic acid modifier) M+1: 210.23 (3.13 min); $^1H$ NMR (300 MHz, $CDCl_3$) δ 7.54 (dt, J=8.0, 1.2 Hz, 1H), 7.43 (td, J=8.2, 5.2 Hz, 1H), 7.32 (ddd, J =9.7, 8.3, 1.3 Hz, 1H), 6.33 (dd, J=4.9, 2.4 Hz, 1H), 5.80 (t, J=10.9 Hz, 1H), 5.06 (q, J=2.4 Hz, 1H), 3.18-3.07 (m, 1H), 2.94-2.82 (m, 1H) ppm. The minor product was 2-(2-fluoro-6-nitro-phenyl)-2,5-dihydrofuran (15B) (4%): GCMS (Agilent HP-5MS 30 m×250×µm×0.25 µm column heating at 60° C. for 2 min to 300° C. over 15 min with a 1 mL/min flow rate) M+1: 210 (11.95 min). $^1H$ NMR (300 MHz, $CDCl_3$) δ 7.47 (d, J=8.0 Hz, 1H), 7.43-7.34 (m, 1H), 7.30-7.23 (m, 1H), 6.21-6.15 (m, 1H), 6.11-6.06 (m, 1H), 5.97-5.91 (m, 1H), 4.89-4.73 (m, 2H) ppm.

EXAMPLE 13

Preparation of 3-fluoro-2-tetrahydrofuran-2-yl-aniline (16)

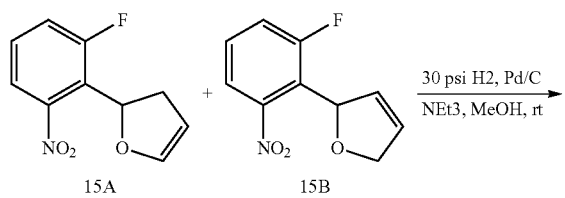

Placed 5% palladium on carbon (37.3 g, 50% wet, 8.76 mmol, Aldrich 330116) in a Parr bottle under nitrogen, followed by MeOH (70 mL, JT-Baker 909333). Added the crude mixture of 2-(2-fluoro-6-nitro-phenyl)-2,3-dihydrofuran and 2-(2-fluoro-6-nitrophenyl)-2,5-dihydrofuran (15A&15B) (186.6 g, 892.1 mmol) dissolved in MeOH (117 mL), followed by $NEt_3$ (124.3 mL, 892.1 mmol, Sigma-Aldrich 471283). Placed the vessel on a Parr shaker and saturated with $H_2$. After adding 45 psi $H_2$, the reaction mixture was shaken until consumption of the starting material was complete (HPLC and LCMS showed complete reaction). The reaction mixture was purged with nitrogen, filtered through Celite™ and rinsed with EtOAc. The filtrate was concentrated on a rotary evaporator giving a brown oil, which was dissolved in $Et_2O$ and washed with water (2×). The ether phase was extracted with aqueous 1 N HCl (5×250 mL), which was washed with $Et_2O$ (3×) and then basified with aqueous 6 N NaOH to pH 12-14. The basic aqueous phase was extracted with $CH_2Cl_2$(4×), and the combined organic extract washed with saturated aqueous $NH_4Cl$, dried over $MgSO_4$, and filtered through a pad of silica eluting with $CH_2Cl_2$ to 25% EtOAc/hexane. The desired filtrate was concentrated under reduced pressure giving 16 as a light brown oil (121.8 g, 84% GCMS plus NMR purity). GCMS (Agilent HP-5MS 30 m×250 µm×0.25 µm column heating at 60° C. for 2 min to 300° C. over 15 min with a 1 mL/min flow rate) M+1: 182.0 (11.44 min). LCMS (C18 column eluting with 10-90% $CH_3CN$/water gradient over 5 minutes with formic acid modifier) M+1: 182.10 (2.61 min). $^1H$-NMR (300 MHz, $CDCl_3$) δ 6.97 (td, J=8.1, 6.3 Hz, 1H), 6.43-6.35 (m, 2H), 5.21-5.13 (m, 1H), 4.54 (s, 2H), 4.16-4.07 (m, 1H), 3.90-3.81 (m, 1H), 2.23-2.00 (m, 4H) ppm. Additional crops were obtained as follows: the combined ether phase was washed with saturated aqueous $NaHCO_3$, brine, dried over $Na_2SO_4$, decanted, and concentrated under reduced pressure. The oil was vacuum distilled (ca. 15 torr) collecting the distillate at 101-108° C. To a stirring solution of the distilled oil in EtOH (1 volume) at 2° C. was slowly added 5 M HCl (1 eq) in iPrOH. The resulting suspension was brought to room temperature, diluted with EtOAc (3 volumes, vol/vol), and stirred for 2 hrs. The white solid was collected by filtration, washed with EtOAc, and dried under reduced pressure giving a second crop of product as the HCl salt. The mother liquor was concentrated to a slurry, diluted with EtOAc and the solid collected by filtration, washed with EtOAc, and dried in vacuo giving the HCl salt as a third crop of the product. LCMS (C18 column eluting with 10-90% $CH_3CN$/water gradient over 5 minutes with formic acid modifier) M+1: 182.10 (2.58 min). $^1H$ NMR (300 MHz, $CDCl_3$) δ 10.73 (br.s, 3H), 7.66 (d, J=8.1 Hz, 1H), 7.33 (td, J=8.2, 5.9 Hz, 1H), 7.13-7.05 (m, 1H), 5.26 (dd, J=9.0, 6.5 Hz, 1H), 4.38-4.28 (m, 1H), 4.00-3.91 (m, 1H), 2.59-2.46 (m, 1H), 2.30-1.95 (m, 3H) ppm. The overall yield from the three crops was 76%.

EXAMPLE 14

Preparation of 4-bromo-3-fluoro-2-tetrahydrofuran-2-yl-aniline (17)

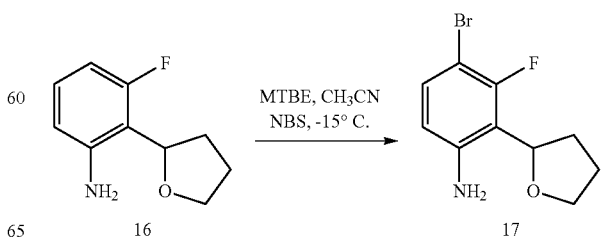

To a stirring solution of 3-fluoro-2-tetrahydrofuran-2-yl-aniline (16) (131.9 g, 92%, 669.7 mmol) in methyl tert-butyl ether (1.456 L) and acetonitrile (485 mL) cooled to −20° C. was added N-bromosuccinimide (120.4 g, 99%, 669.7 mmol, Aldrich B81255) in 3 portions maintaining a reaction temperature below about −15° C. After complete addition stirring was continued at −15 to −10° C. for 30 minutes. $^1$H NMR of a worked-up aliquot showed 96% consumption of starting aniline so added another 4.82 g NBS and stirred at −10° C. for another 30 minutes. Aqueous 1 N $Na_2S_2O_3$ (670 mL) was added to the reaction mixture. The cold bath was removed, the mixture stirred for 20 minutes, then diluted with EtOAc. The layers were separated and the organic phase was washed with saturated aqueous $NaHCO_3$ (2×), water, brine, dried over $Na_2SO_4$, decanted, and concentrated under reduced pressure giving a dark amber oil. The residue was diluted with hexane and eluted through a short plug of silica eluting with 25% EtOAc/hexane to 50% EtOAc/hexane. The desired filtrate was concentrated in vacuo giving 17 as a dark amber oil (182.9 g, 90% yield; 86% NMR purity). LCMS (C18 column eluting with 10-90% $CH_3CN$/water gradient over 5 minutes with formic acid modifier) M+1: 260.12 (3.20 min). $^1$H NMR (300 MHz, $CDCl_3$) δ 7.15 (dd, J=8.6, 7.6 Hz, 1H), 6.30 (dd, J=8.7, 1.3 Hz, 1H), 5.19-5.12 (m, 1H), 4.58 (s, 2H), 4.16-4.07 (m, 1H), 3.90-3.81 (m, 1H), 2.23-1.99 (m, 4H) ppm.

EXAMPLE 15

Preparation of N-(4-bromo-3-fluoro-6-nitro-2-tetrahydrofuran-2-yl-phenyl)-2,2,2-trifluoro-acetamide (18)

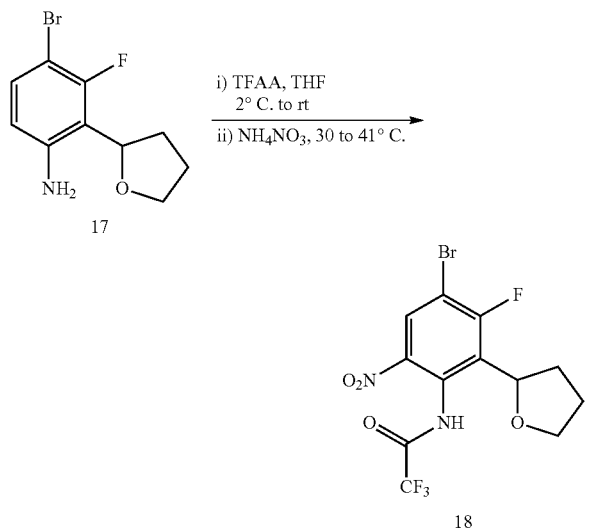

To trifluoroacetic anhydride (565.3 mL, 4.067 mol, Sigma-Aldrich 106232) stirring at 2° C. was slowly added neat 4-bromo-3-fluoro-2-tetrahydrofuran-2-yl-aniline (17) (123.0 g, 86%, 406.7 mmol) as a thick oil via addition funnel over about 20 minutes (reaction temperature rose to 13° C.). The remaining oil was rinsed into the reaction mixture with anhydrous THF (35 mL). The cold bath was removed and the reaction was heated to 35° C., followed by portion-wise addition of $NH_4NO_3$ (4.88 g×20 portions, 1.22 mol, Sigma-Aldrich A7455) over 2.5 hrs maintaining the reaction temperature between 30 and 41° C. using an ice-water bath only as needed to control the exotherm. After complete addition the reaction mixture was stirred for another 10 minutes (HPLC showed reaction 99% complete). It was slowly poured into crushed ice (1.23 kg) and stirred for 1 hr to allow formation of a filterable solid precipitate, which was collected and washed with water, sparingly with saturated aqueous $NaHCO_3$, and water again (to pH 7). The product was dried in a convection oven overnight at 40° C. and then under reduced pressure in an oven at 50° C. overnight giving 18 as a beige solid (152.5 g, 90% yield; 96% HPLC purity). LCMS (C18 column eluting with 10-90% $CH_3CN$/water gradient over 5 minutes with formic acid modifier) M+1: 401.30 (3.41 min). $^1$H NMR (300 MHz, $CDCl_3$) δ 10.56 (s, 1H), 8.19 (d, J=6.6 Hz, 1H), 5.22 (dd, J=10.3, 6.4 Hz, 1H), 4.22 (dd, J=15.8, 7.2 Hz, 1H), 3.99 (dd, J=16A, 7.5 Hz, 1H), 2.50-2.38 (m, 1H), 2.22-2.11 (m, 2H), 1.86-1.71 (m, 1H) ppm.

EXAMPLE 16

Preparation of 4-bromo-3-fluoro-6-nitro-2-tetrahydrofuran-2-yl-aniline (19)

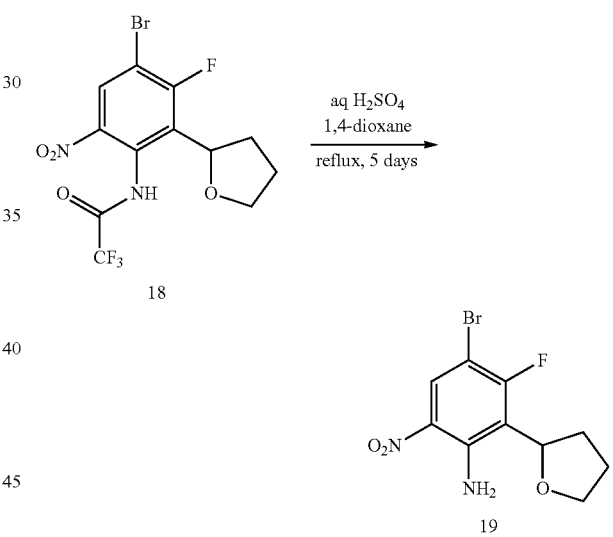

A reaction flask was charged with N-(4-bromo-3-fluoro-6-nitro-2-tetrahydrofuran-2-yl-phenyl)-2,2,2-trifluoro-acetamide (18) (242.3 g, 604.1 mmol), 1,4-dioxane (1.212 L), aqueous 2 M sulfuric acid (362.4 mL, 724.9 mmol), and stirred at reflux for 5 days (HPLC showed 98% conversion). Allowed to cool, diluted with EtOAc, neutralized with saturated aqueous $NaHCO_3$, separated the layers, and re-extracted the aqueous phase with EtOAc (2×). The combined organic phase was washed with brine (2×), dried over $MgSO_4$, filtered and concentrated in vacuo giving 19 as a greenish brown solid (181.7 g, 94% yield; 95% HPLC purity). The product was carried to the next step without further purification. LCMS (C18 column eluting with 10-90% $CH_3CN$/water gradient over 5 minutes with formic acid modifier) M+1: 305.20 (3.63 min). $^1$H NMR (300 MHz, $CDCl_3$) δ 8.35 (d, J=7.3 Hz, 1H), 7.45 (s, 2H), 5.23-5.16 (m, 1H), 4.23-4.14 (m, 1H), 3.93-3.84 (m, 1H), 2.31-1.96 (m, 4H) ppm.

EXAMPLE 17

Preparation of 2-[5-(4-amino-2-fluoro-5-nitro-3-tetrahydrofuran-2-yl-phenyl)pyrimidin-2-yl]propan-2-ol (20)

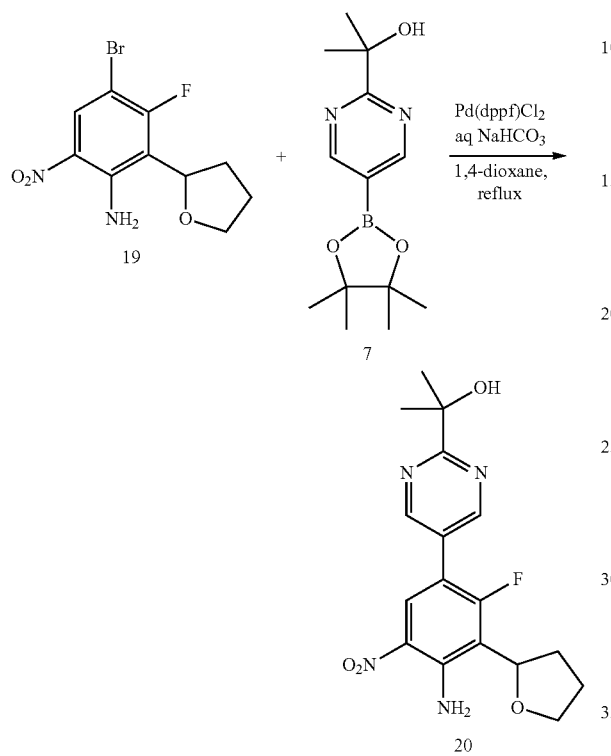

To a stirring solution of 4-bromo-3-fluoro-6-nitro-2-tetrahydrofuran-2-yl-aniline (19) (525.0 g, 1.721 mol, Bridge Organics Co.) in 1,4-dioxane (4.20 L, Sigma-Aldrich 360481) was added a 1.2 M aqueous solution of NaHCO₃ (4.302 L, 5.163 mol). A stream of nitrogen was bubbled through the stirring mixture for 2 hrs, followed by addition of 2-[5-(4,4,5,5-tetramethyl-1,3,2-dioxaborolan-2-yl)pyrimidin-2-yl]propan-2-ol (7) (545.4 g, 2.065 mol, Bridge Organics Co.) and 1,1'-bis(diphenylphosphino)ferrocene dichloropalladium dichloromethane adduct (42.16 g, 51.63 mmol, Strem 460450). The reaction mixture was stirred at reflux overnight, allowed to cool, diluted with EtOAc (8.4 L), and the layers were separated. The organic phase was washed with saturated aqueous NH₄Cl and then brine. The aqueous phase was re-extracted with EtOAc (4 L) and washed this organic extract with brine. The combined organic phase was dried over MgSO₄, filtered through a short plug of Florisil®, eluted with EtOAc, and the filtrate concentrated on a rotary evaporator giving a dark brown wet solid. This was dissolved in CH₂Cl₂, loaded on a pad of silica gel, eluted with hexane, then 25% EtOAc/hexane, and then 50% EtOAc/hexane. The desired filtrate was concentrated on a rotary evaporator to a thick suspension, and the solid was collected by filtration, triturated with MTBE, and dried in vacuo giving 20 as a bright yellow solid (55.8% yield, 90-97% HPLC purity). The filtrate was concentrated and the above purification was repeated giving a second crop of 20 as a bright yellow solid (19.7% yield). The filtrate was again concentrated giving a dark brown oil and this was loaded on a silica column with toluene and minimal CH₂Cl₂. It was eluted with EtOAc/hexane (0% to 50%). The desired fractions were concentrated to a slurry and diluted with MTBE/hexane. The solid was collected by filtration and washed with minimal MTBE giving a third crop of 20 as a bright yellow solid (4.9% yield) with an overall yield of 80% from the three crops. LCMS (C18 column eluting with 10-90% CH₃CN/water gradient over 5 minutes with formic acid modifier) M+1: 363.48 (2.95 min). ¹H NMR (300 MHz, CDCl₃) δ 8.84 (d, J=1.6 Hz, 2H), 8.27 (d, J=8.0 Hz, 1H), 7.62 (s, 2H), 5.31-5.24 (m, 1H), 4.63 (s, 1H), 4.27-4.18 (m, 1H), 3.97-3.87 (m, 1H), 2.33-2.05 (m, 4H), 1.64 (s, 6H) ppm.

EXAMPLE 18

Preparation of 2-[5-(4,5-diamino-2-fluoro-3-tetrahydrofuran-2-yl-phenyl)pyrimidin-2-yl]propan-2-ol (21)

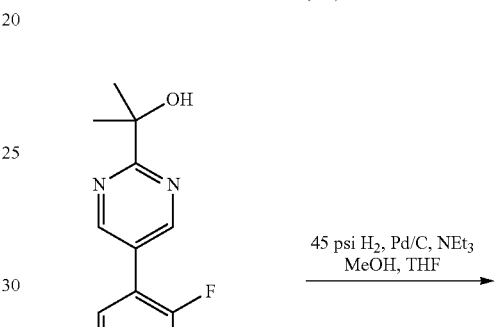

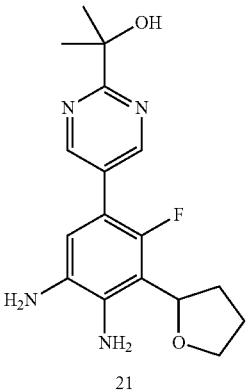

Placed 5% palladium on carbon (14.21 g, 50% wet, 3.339 mmol, Aldrich 330116) in a Parr bottle under nitrogen, followed by MeOH (242 mL, JT-Baker 909333) and NEt₃ (46.54 mL, 333.9 mmol, Sigma-Aldrich 471283). Dissolved 2-[5-(4-amino-2-fluoro-5-nitro-3-tetrahydrofuran-2-yl-phenyl)pyrimidin-2-yl]propan-2-ol (20) (121.0 g, 333.9 mmol) in hot THF (360 mL), allowed to cool, added to the reaction mixture, and rinsed with another portion of THF (124 mL). Placed the vessel on a Parr shaker and saturated with H₂. Added 45 psi H₂ and shook until consumption was complete (HPLC and LCMS showed complete reaction). The reaction mixture was purged with nitrogen, filtered through Celite™ and rinsed with EtOAc. It was re-filtered through paper (glass microfibre) and the filtrate concentrated in vacuo.

Repeated the reaction three more times on the same scale and the batches were combined giving 21 as a brown solid (447 g, 99% yield; 93% HPLC purity). LCMS (C18 column eluting with 10-90% $CH_3CN$/water gradient over 5 minutes with formic acid modifier) M+1: 333.46 (1.79 min). $^1$H NMR (300 MHz, $CDCl_3$) δ 8.81 (d, J=1.4 Hz, 2H), 6.69 (d, J=7.3 Hz, 1H), 5.27-5.20 (m, 1H), 4.73 (s, 1H), 4.70 (s, 2H), 4.23-4.14 (m, 1H), 3.94-3.86 (m, 1H), 3.22 (s, 2H), 2.32-2.22 (m, 1H), 2.18-199 (m, 3H), 1.63 (s, 6H) ppm.

EXAMPLE 19

Preparation of 1-ethyl-3-[6-fluoro-5-[2-(1-hydroxy-1-methyl-ethyl)pyrimidin-5-yl]-7-tetrahydrofuran-2-yl-1H-benzimidazol-2-yl]urea (22)

was stirred for 30 minutes, the solid was collected by filtration, washed copiously with water to neutral pH, and then more sparingly with EtOH. The solid was dried under reduced pressure giving 22 as an off-white yellowish solid (135.2 g, 94% yield; 99% HPLC purity). LCMS (C18 column eluting with 10-90% $CH_3CN$/water gradient over 5 minutes with formic acid modifier) M+1: 429.58 (2.03 min). $^1$H NMR (300 MHz, MeOD) δ 8.95 (d, J=1.6 Hz, 2H), 7.45 (d, J=6.5 Hz, 1H), 5.38 (br.s, 1H), 4.27 (dd, J=14.9, 7.1 Hz, 1H), 4.01 (dd, J=15.1, 7.0 Hz, 1H), 3.37-3.29 (m, 2H), 2.55 (br.s, 1H), 2.19-2.07 (m, 2H), 2.02-1.82 (br.s, 1H), 1.63 (s, 6H), 1.21 (t, J=7.2 Hz, 3H) ppm.

EXAMPLE 20

Chiral chromatographic isolation of 1-ethyl-3-[6-fluoro-5-[2-(1-hydroxy-1-methyl-ethyl)pyrimidin-5-yl]-7-[(2R)-tetrahydrofuran-2-yl]-1H-benzimidazol-2-yl]urea (23)

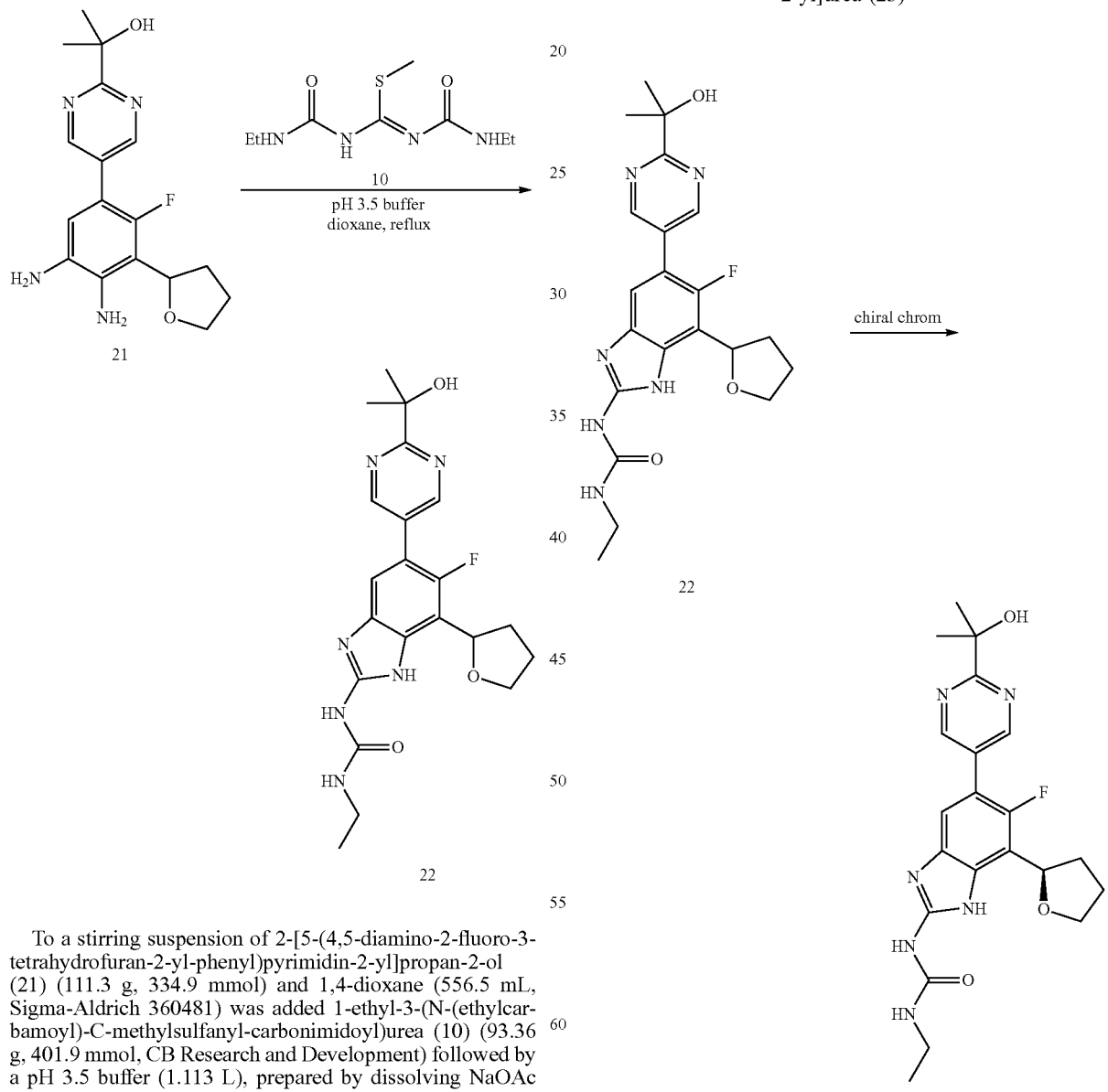

To a stirring suspension of 2-[5-(4,5-diamino-2-fluoro-3-tetrahydrofuran-2-yl-phenyl)pyrimidin-2-yl]propan-2-ol (21) (111.3 g, 334.9 mmol) and 1,4-dioxane (556.5 mL, Sigma-Aldrich 360481) was added 1-ethyl-3-(N-(ethylcarbamoyl)-C-methylsulfanyl-carbonimidoyl)urea (10) (93.36 g, 401.9 mmol, CB Research and Development) followed by a pH 3.5 buffer (1.113 L), prepared by dissolving NaOAc trihydrate (158.1 g) in 1N aqueous $H_2SO_4$ (1.100 L). The reaction mixture was stirred at reflux overnight (HPLC showed complete conversion), cooled to room temperature, and poured portion-wise (frothing) into a stirring solution of aqueous saturated $NaHCO_3$ (2.23 L) giving pH 8-9. This A racemic sample of 1-ethyl-3-[6-fluoro-5-[2-(1-hydroxy-1-methyl-ethyl)pyrimidin-5-yl]-7-tetrahydrofuran-2- yl-1H-benzimidazol-2-yl]urea (22) (133.60 g) was resolved on a CHIRALPAK® IC® column (by Chiral Technologies) eluting with DCM/MeOH/TEA (60/40/0.1) at 25° C. giving the desired enantiomer 23 as an off-white solid (66.8 g, 45% yield; 99.8% HPLC purity, 99+% ee). Analytical chiral HPLC retention time was 7.7 min (CHIRALPAK® IC® 4.6×250 mm column, 1 mL/min flow rate, 30° C.). The solid was suspended in 2:1 EtOH/Et$_2$O (5 volumes), stirred for 10 minutes, collected by filtration, washed with 2:1 EtOH/Et$_2$O, and dried under reduced pressure giving a white solid (60.6 g).

The structure and absolute stereochemistry of 23 were confirmed by single-crystal x-ray diffraction analysis. Single crystal diffraction data were acquired on a Bruker Apex II diffractometer equipped with sealed tube Cu K-alpha source (Cu Kα radiation, γ=1.54178 Å) and an Apex II CCD detector. A crystal with dimensions of 0.15×0.15×0.10 mm was selected, cleaned using mineral oil, mounted on a MicroMount and centered on a Bruker APEXII system. Three batches of 40 frames separated in reciprocal space were obtained to provide an orientation matrix and initial cell parameters. Final cell parameters were obtained and refined after data collection was completed based on the full data set. Based on systematic absences and intensities statistics the structure was solved and refined in acentric P2$_1$ space group.

Figure 2:
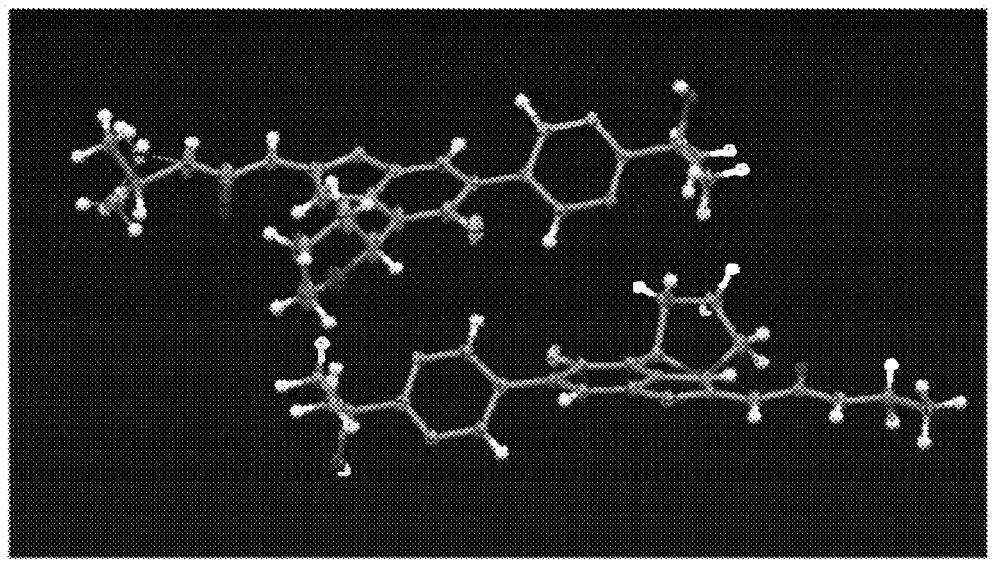
FIG. 2 is a thermal ellipsoid plot of two symmetry independent molecules of compound 23.

A diffraction data set of reciprocal space was obtained to a resolution of 0.85 Å using 0.5° steps using 30 s exposures for each frame. Data were collected at 100 (2) K. Integration of intensities and refinement of cell parameters were accomplished using APEXII software. Observation of the crystal after data collection showed no signs of decomposition. As shown in FIG. 2, there are two symmetry independent molecules in the structure and both symmetry independent molecules are R isomers.

The data were collected, refined and reduced using the Apex II software. The structure was solved using the SHELXS97 (Sheldrick, 1990); program(s) and the structure refined using the SHELXL97 (Sheldrick, 1997) program. The crystal shows monoclinic cell with P2$_1$ space group. The lattice parameters are a=9.9016(2) Å, b=10.9184(2) Å, c=19.2975(4) Å, β=102.826(1)°. Volume=2034.19(7) Å$^3$.

EXAMPLE 21

Preparation of the methanesulfonic acid salt of 1-ethyl-3-[6-fluoro-5-[2-(1-hydroxy-1-methyl-ethyl)pyrimidin-5-yl]-7-[(2R)-tetrahydrofuran-2-yl]-1H-benzimidazol-2-yl]urea (23A)

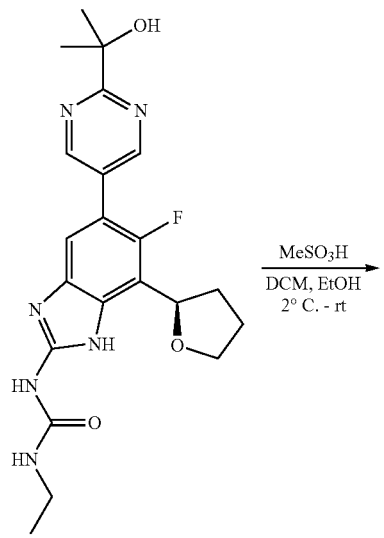

23

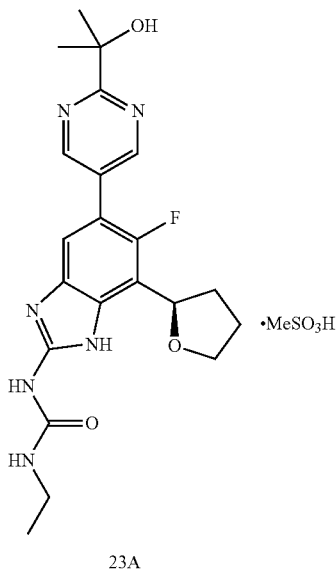

23A

To a stirring suspension of 1-ethyl-3-[6-fluoro-5-[2-(1-hydroxy-1-methyl-ethyl)pyrimidin-5-yl]-7-[(2R)-tetrahydrofuran-2-yl]-1H-benzimidazol-2-yl]urea (23) (15.05 g, 35.13 mmol) in dichloromethane (60 mL, J. T. Baker 931533) and absolute ethanol (15 mL, Pharmco-AAPER 111000200) was added methanesulfonic acid (2.392 mL, 36.89 mmol, Sigma-Aldrich 471356). Stirred at room temperature until a clear solution was observed. Added heptane (300 mL) slowly over about 1 hr and collected the solid precipitate by filtration (using a Whatman qualitative #3 paper on top of a Whatman GF/F glass microfibre paper). Dried under reduced pressure in a vacuum oven (desiccated with calcium sulfate and potassium hydroxide) overnight at 40° C. giving 23A as a white solid (13.46 g, 99+% HPLC purity, 99+% ee). Analytical chiral HPLC shows one enantiomer with retention time of 8.6 min eluting with CH$_2$Cl$_2$/MeOH/TEA (60/40/0.1) on a CHIRAL PAK® IC® 4.6×250 mm column with 1 mL/min flow rate at 30° C. A second crop of white solid product 23A (4.36 g, 98% HPLC purity, 99+% ee) was obtained from the filtrate. LCMS (C18 column eluting with 10-90% CH$_3$CN/water gradient over 5 minutes with formic acid modifier) M+1: 429.58 (2.03 min). $^1$H NMR (300 MHz, MeOD) δ 9.00 (d, J=1.6 Hz, 2H), 7.67 (d, J=6.1 Hz, 1H), 5.39 (t, J=7.7 Hz, 1H), 4.30 (dd, J=14.9, 6.9 Hz, 1H), 4.03 (dd, J=14.8, 7.7 Hz, 1H), 3.40-3.31 (m, 2H), 2.72 (s, 3H), 2.70-2.60 (m, 1H), 2.21-2.08 (m, 2H), 1.98-1.84 (m, 1H), 165 (s, 6H), 122 (t, J=7.2 Hz, 3H) ppm.

The (R)-1-ethyl-3-(6-fluoro-5-(2-(2-hydroxypropan-2-yl)pyrimidin-5-yl)-7-(tetrahydrofuran-2-yl)-1H-benzo[d]imidazol-2-yl)urea 23 may then be converted to the phosphate or phosphate salt prodrugs according to the schemes set forth below.

Scheme 1

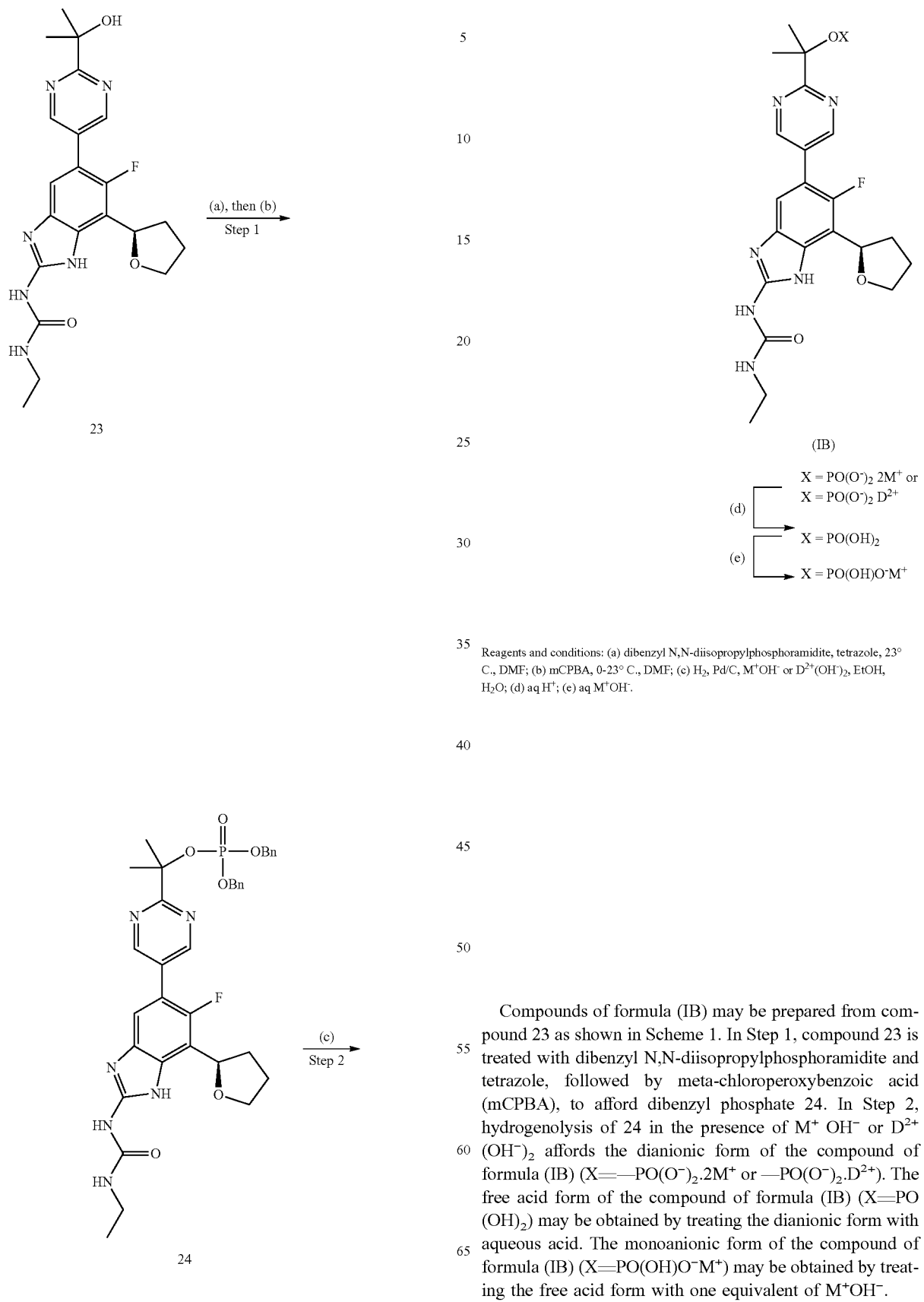

Reagents and conditions: (a) dibenzyl N,N-diisopropylphosphoramidite, tetrazole, 23° C., DMF; (b) mCPBA, 0-23° C., DMF; (c) H₂, Pd/C, M⁺OH⁻ or D²⁺(OH⁻)₂, EtOH, H₂O; (d) aq H⁺; (e) aq M⁺OH⁻.

Compounds of formula (IB) may be prepared from compound 23 as shown in Scheme 1. In Step 1, compound 23 is treated with dibenzyl N,N-diisopropylphosphoramidite and tetrazole, followed by meta-chloroperoxybenzoic acid (mCPBA), to afford dibenzyl phosphate 24. In Step 2, hydrogenolysis of 24 in the presence of M⁺ OH⁻ or D²⁺ (OH⁻)₂ affords the dianionic form of the compound of formula (IB) (X=—PO(O⁻)₂.2M⁺ or —PO(O⁻)₂.D²⁺). The free acid form of the compound of formula (IB) (X=PO (OH)₂) may be obtained by treating the dianionic form with aqueous acid. The monoanionic form of the compound of formula (IB) (X=PO(OH)O⁻M⁺) may be obtained by treating the free acid form with one equivalent of M⁺OH⁻.

Scheme 2
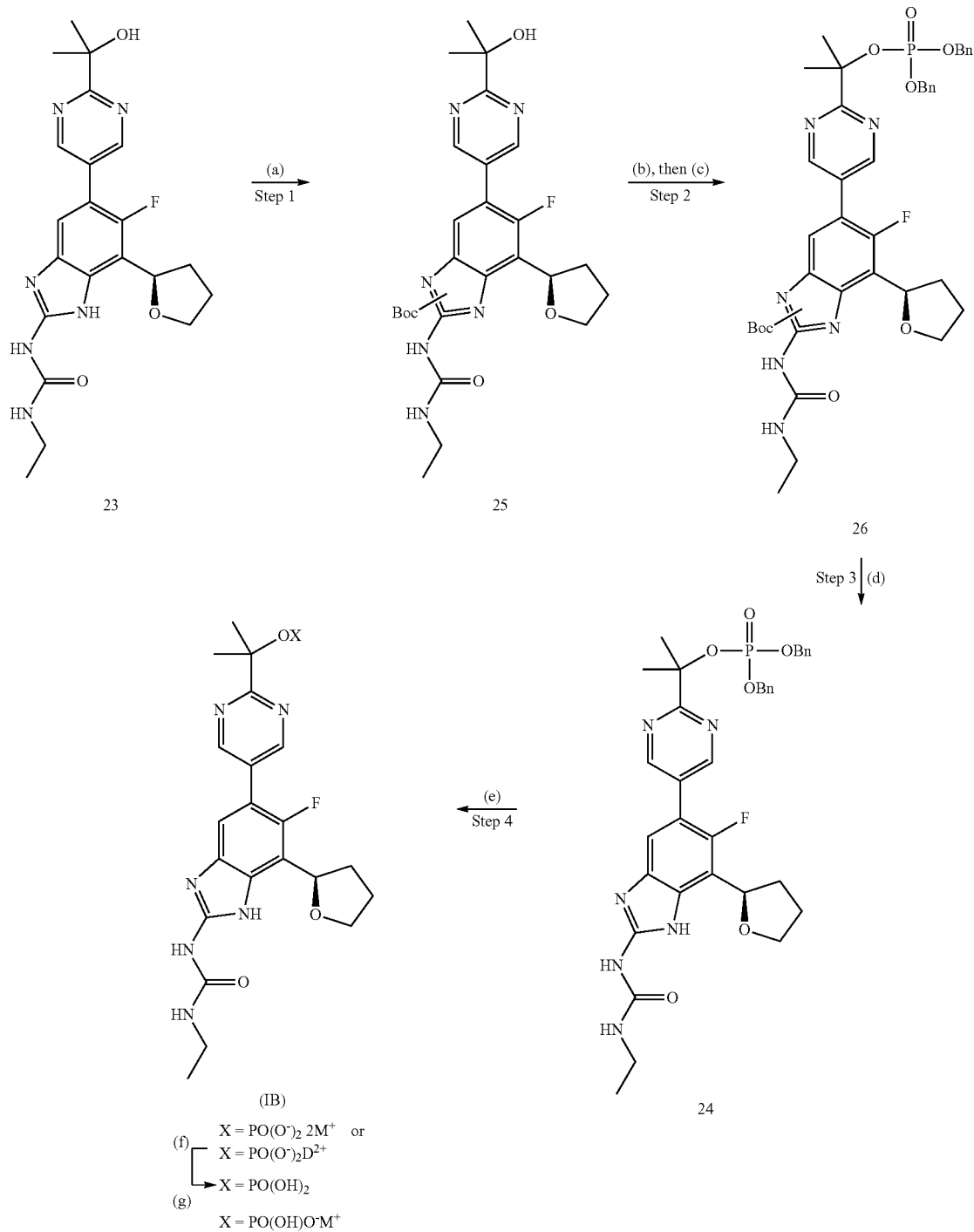
Reagents and conditions:
(a) Boc₂O, DMF, 23 °C.;
(b) dibenzyl N,N-diisopropylphosphoramidite, tetrazole 23 °C., DMF;
(c) mCPBA, 0-23 °C., DMF;
(d) TFA, H₂O, MeOH, DCM, 23 °C.;
(e) H₂, Pd/C, M⁺ OH⁻ or D²⁺ (OH⁻)₂, EtOH, H₂O;
(f) aq H⁺;
(g) aq M⁺ OH⁻.

Alternatively, the compounds of formula (IB) may be prepared from compound 23 as shown in Scheme 2. In Step 1, compound 23 is treated with di-tert-butyl dicarbonate (Boc₂O) to afford protected benzimidazole compound 25. In Step 2, compound 25 is treated with dibenzyl N,N-diisopropylphosphoramidite and tetrazole, followed by mCPBA, to afford protected dibenzyl phosphate 26. In Step 3, compound 26 is treated with trifluoroacetic acid (TFA) to remove the protecting group and afford dibenzyl phosphate 24. In Step 4, hydrogenolysis of 24 in the presence of $M^+OH^-$ or $D^{2+}(OH^-)_2$ affords the dianionic form of the compound of formula (IB) ($X=-PO(O^-)_2.2M^+$ or $-PO(O^-)_2.D^{2+}$). The free acid form of the compound of formula (IB) ($X=PO(OH)_2$) may be obtained by treating the dianionic form with aqueous acid. The monoanionic form of the compound of formula (I) ($X=PO(OH)O^-M^+$) may be obtained by treating the free acid form with one equivalent of $M^+OH^-$.

Scheme 3

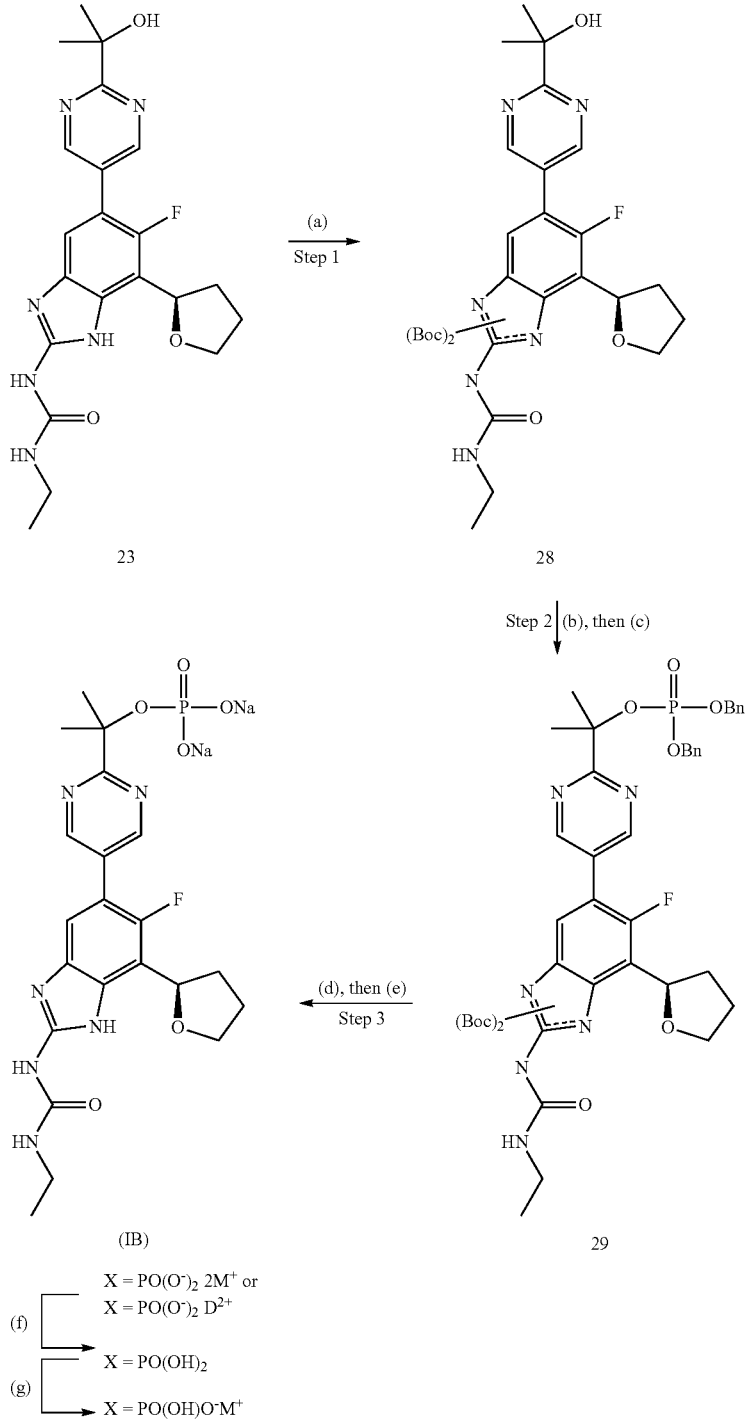

Reagents and conditions: (a) Boc₂O, DMAP, DMF, 23° C.; (b) dibenzyl N,N-diisopropylphosphoramidite, tetrazole, 23° C., DMF; (c) mCPBA, 0-23° C., DMF; (d) TFA, DCM; (e) aq $M^+OH^-$ or $D^{2+}(OH^-)_2$; (f) aq $H^+$; (g) aq $M^+OH^-$.

The compounds of formula (IB) may also be prepared from compound 23 as shown in Scheme 3. In Step 1, compound 23 is treated with two equivalents of Boc$_2$O in the presence of N,N-dimethylaminopyridine (DMAP) to afford bis-protected benzimidazole compound 28. In Step 2, compound 28 is treated with dibenzyl N,N-diisopropylphosphoramidite and tetrazole, followed by mCPBA, to afford bis-protected dibenzyl phosphate 29. In Step 3, compound 29 is treated with TFA to remove the protecting groups. Treatment of the resulting intermediate with aqueous M$^+$OH$^-$ or D$^{2+}$(OH$^-$)$_2$ affords the dianionic form of the compound of formula (IB) (X=—PO(O$^-$)$_2$.2M$^+$ or —PO(O$^-$)$_2$.D$^{2+}$). The free acid form of the compound of formula (IB) (X=PO(OH)$_2$) may be obtained by treating the dianionic form with aqueous acid. The monoanionic form of the compound of formula (I) (X=PO(OH)O$^-$M$^+$) may be obtained by treating the free acid form with one equivalent of M$^+$OH$^-$.

EXAMPLE 22

Preparation of (R)-dibenzyl 2-(5-(2-(3-ethylureido)-6-fluoro-7-(tetrahydrofuran-2-yl)-1H-benzo[d]imidazol-5-yl)pyrimidin-2-yl)propan-2-yl phosphate (24)

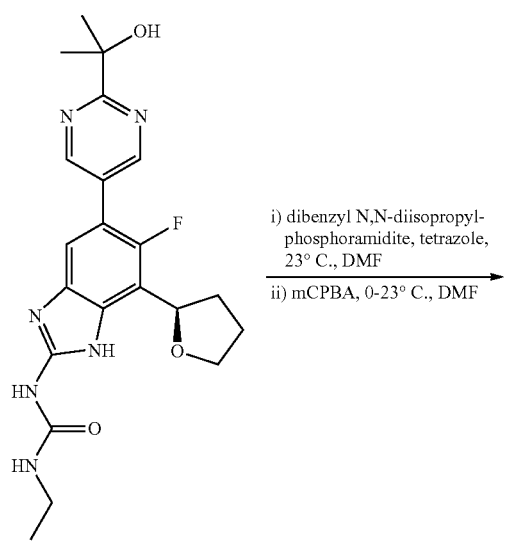

23 i) dibenzyl N,N-diisopropyl-phosphoramidite, tetrazole, 23° C., DMF ii) mCPBA, 0-23° C., DMF

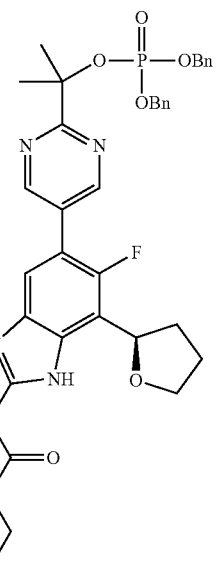

24

To 1-ethyl-3-[6-fluoro-5-[2-(1-hydroxy-1-methyl-ethyl)pyrimidin-5-yl]-7-[(2R)-tetrahydrofuran-2-yl]-1H-benzimidazol-2-yl]urea (23) (10.24 g, 23.66 mmol) in a 1 L round bottom flask under N$_2$ at 23° C. was added DMF (200 mL) followed by a solution of tetrazole (105.2 mL of 0.45 M in MeCN, 47.32 mmol) followed by N-dibenzyloxyphosphanyl-N-isopropyl-propan-2-amine (12.26 g, 11.93 mL, 35.49 mmol). After 4.5 h more N-dibenzyloxyphosphanyl-N-isopropyl-propan-2-amine (4 mL) was added. After stirring a further 16 h the reaction was cooled to 0° C. (ice-water bath) then treated with mCPBA (15.17 g, 61.52 mmol). The mixture was stirred at 0° C. for 30 min then at 23° C. for 30 min after which the reaction mixture was partitioned between water (400 mL) and EtOAc (700 mL). The organic layer was separated, washed with saturated aqueous sodium bicarbonate (500 mL), 10% aqueous sodium bisulfite (500 mL), saturated aqueous sodium bicarbonate (500 mL), and brine (500 mL) then dried (magnesium sulfate), filtered and concentrated. The residue was purified by MPLC using an ISCO COMBIFLASH brand flash chromatography purification system (330 g column) eluting with a 0-10% EtOH in DCM linear gradient over 16.5 column volumes at a 200 mL/min flow rate. After concentration in vacuo, (R)-dibenzyl 2-(5-(2-(3-ethylureido)-6-fluoro-7-(tetrahydrofuran-2-yl)-1H-benzo[d]imidazol-5-yl)pyrimidin-2-yl)propan-2-yl phosphate(24) (13.89 g, 20.17 mmol, 85.27%) was obtained as a white solid. ESMS (M+1)=689.5; $^1$H NMR (300 MHz, CD$_3$OD) δ 8.88 (d, J=1.6 Hz, 2H), 7.37 (d, J=6 Hz, 1H), 7.30 (m, 10H), 5.38-5.33 (m, 1H), 5.12-5.01 (m, 4H), 4.24 (dd, J=6.8, 14.9 Hz, 1H), 3.98 (dd, J=6.9, 15.1 Hz, 1H), 3.35-3.27 (m, 3H), 2.52 (q, J=5.9 Hz, 1H), 2.14-2.05 (m, 2H), 191 (s, 6H) and 1.22-1.14 (m, 3H) ppm.

EXAMPLE 23

Preparation of disodium (R)-2-(5-(2-(3-ethylureido)-6-fluoro-7-(tetrahydrofuran-2-yl)-1H-benzo[d]imidazol-5-yl)pyrimidin-2-yl)propan-2-yl phosphate (W)

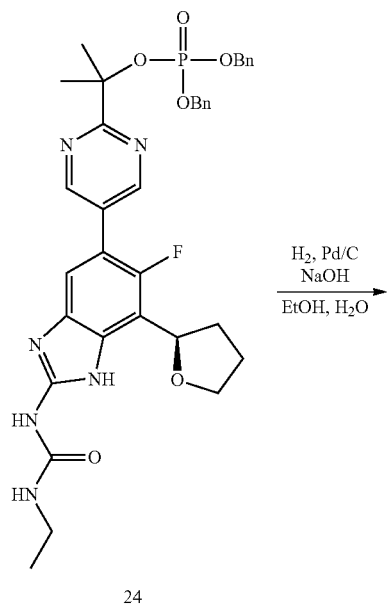

A 1 L Parr vessel was charged with water (200 mL), Pd/C (4 g, 10 wt % dry basis, wet, Degussa type), (R)-dibenzyl 2-(5-(2-(3-ethylureido)-6-fluoro-7-(tetrahydrofuran-2-yl)-1H-benzo[d]imidazol-5-yl)pyrimidin-2-yl)propan-2-yl phosphate(24) (13.89 g, 20.17 mmol), EtOH (400 mL) and aqueous 1 M NaOH (40.34 mL, 40.34 mmol). The resulting mixture was hydrogenated under 50 psi $H_2$ on a Parr shaker apparatus for 40 min. The reaction mixture was filtered through a 0.22 μm polyethersulfone (PES) membrane giving a dark colored filtrate. A water rinse resulted in more dark material crossing the filter membrane. The resulting filtrate was passed through a pad of Celite and the dark material did not elute until the pad was rinsed with water. The resulting dark solution (approx. 700 mL) was diluted with three volumes of EtOH (2100 mL), filtered through a 0.22 μm PES membrane (using 4 disposable Corning polystyrene filter systems, #431098) and the filtrate concentrated in vacuo. The resulting residue was dissolved in water (100 mL) and EtOH (300 mL), filtered through a 0.22 μm PES membrane to give a clear yellow solution, then passed through a Celite plug (26 mm diameter×60 mm height, pre-wet with EtOH) rinsing with EtOH (50 mL) and the filtrate then concentrated. The resulting residue was dissolved in water (250 mL) in a 1 L round bottom flask, then 1 M aqueous HCl (40 mL) was slowly added over 15 min with stirring to give a slurry of white solid. Twenty minutes following completion of the HCl addition, the solid was collected via filtration through a 0.22 μm PES membrane. The collected solid was washed with water (100 mL), then transferred (still wet) to a 1 L round bottom flask and slurried in MeOH (150 mL) for 30 min. The resulting fine white precipitate was collected via filtration then dried in vacuo overnight. The resulting free acid (9.17 g, 18.0 mmol) was treated with water (80 mL) then 1.0 N aq NaOH (36.0 mL, 2 equiv). The resulting solution was frozen and lyophilized to give disodium[1-[5-[2-(ethylcarbamoylamino)-6-fluoro-7-[(2R)-tetrahydrofuran-2-yl]-1H-benzimidazol-5-yl]pyrimidin-2-yl]-1-methyl-ethyl]phosphate (W) (10.206 g, 18.08 mmol, 89.66%) as a pale, cream-colored solid with consistent analytical data. ESMS (M+1)=509.4; $^1$H NMR (300 MHz, $D_2O$) δ 8.58 (s, 2H), 6.92 (d, J=6.3 Hz, 1H), 5.13 (t, J=7.5 Hz, 1H), 3.98-3.81 (m, 2H), 3.04 (q, J=7.2 Hz, 2H), 2.26 (t, J=5.7 Hz, 1H), 1.97-1.92 (m, 2H), 1.67 (s, 6H) and 1.01 (t, J=7.2 Hz, 3H) ppm.

EXAMPLE 24

Preparation of Boc-1-ethyl-3-[6-fluoro-5-[2-(1-hydroxy-1-methyl-ethyl)pyrimidin-5-yl]-7-[(2R)-tetrahydrofuran-2-yl]-1H-benzimidazol-2-yl]urea (25)

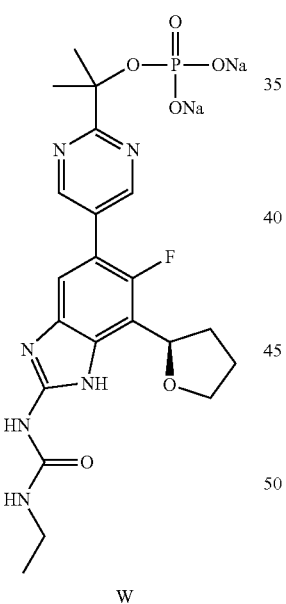

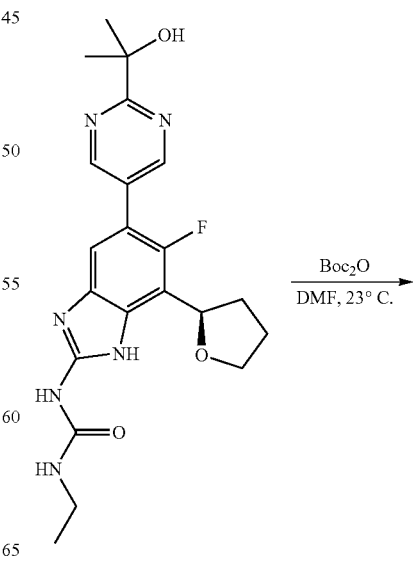

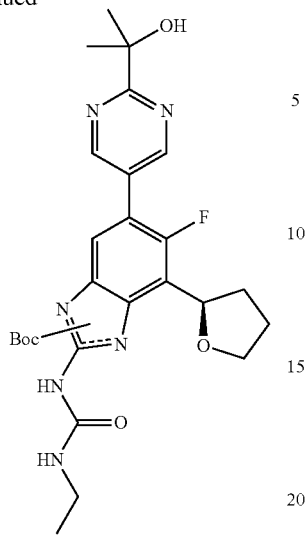

25

To a solution/suspension of 1-ethyl-3-[6-fluoro-5-[2-(1-hydroxy-1-methyl-ethyl)pyrimidin-5-yl]-7-[(2R)-tetrahydrofuran-2-yl]-1H-benzimidazol-2-yl]urea (23) (10.72 g, 25.02 mmol) in DMF (250 mL) at 23° C. was added Boc$_2$O (6.11 g, 28.00 mmol). After 2 hours, 2 M ammonia in MeOH (2 mL) was added to quench any excess Boc$_2$O. The quenched reaction mixture was partitioned between EtOAc and water (400 mL each), the organic layer separated, washed with water (2×400 mL) and brine (400 mL), then dried over MgSO$_4$, filtered and concentrated to give Boc-1-ethyl-3-[6-fluoro-5-[2-(1-hydroxy-1-methyl-ethyl)pyrimidin-5-yl]-7-[(2R)-tetrahydrofuran-2-yl]-1H-benzimidazol-2-yl]urea (25) (12.69 g, 23.58 mmol, 94.26%) which was used without further purification. ESMS (M+1)=529.3; $^1$H NMR (300.0 MHz, CDCl$_3$) δ 9.50 (s, 1H), 9.02 (t, J=5.3 Hz, 1H), 8.91 (d, J=1.6 Hz, 2H), 7.74 (d, J=6.5 Hz, 1H), 5.58 (t, J=7.8 Hz, 1H), 4.64 (s, 1H), 4.22 (q, J=7.4 Hz, 1H), 4.05 (td, J=7.8, 4.3 Hz, 1H), 3.47 (td, J=7.2, 4.3 Hz, 2H), 2.42-2.35 (m, 2H), 2.28-2.16 (m, 2H), 1.75 (s, 9H), 1.68 (s, 6H) and 1.31 (t, J=7.3 Hz, 3H) ppm.

EXAMPLE 25

Preparation of Boc-1-ethyl-3-[6-fluoro-5-[2-(1-hydroxy-1-methyl-ethyl)pyrimidin-5-yl]-7-[(2R)-tetrahydrofuran-2-yl]-1H-benzimidazol-2-yl]urea dibenzyl phosphate (26)

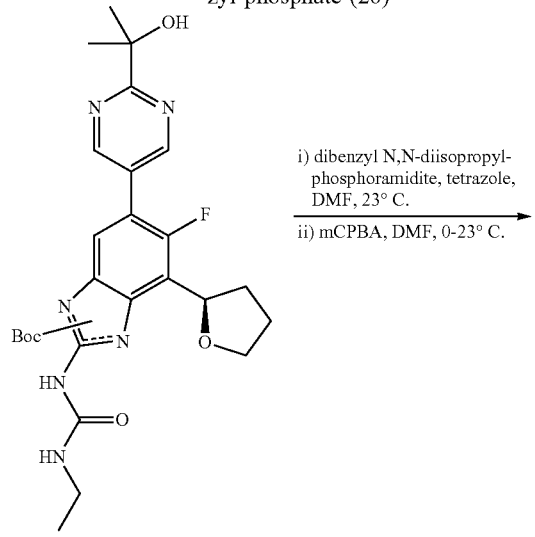

i) dibenzyl N,N-diisopropyl-phosphoramidite, tetrazole, DMF, 23° C.

ii) mCPBA, DMF, 0-23° C.

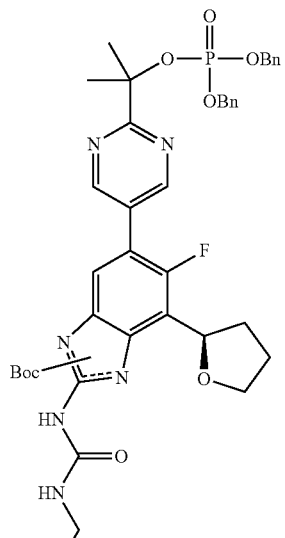

26

To Boc-1-ethyl-3-[6-fluoro-5-[2-(1-hydroxy-1-methyl-ethyl)pyrimidin-5-yl]-7-[(2R)-tetrahydrofuran-2-yl]-1H-benzimidazol-2-yl]urea (25) (12.69 g, 23.58 mmol) and tetrazole (3.304 g, 47.16 mmol) under N$_2$ at 23° C. was added DCM (240 mL) followed by N-dibenzyloxyphosphanyl-N-isopropyl-propan-2-amine (9.775 g, 9.509 mL, 28.30 mmol). After 3 hours at 23° C., the reaction was cooled to 0° C. then mCPBA (6.977 g, 28.30 mmol) was added. The resulting solution was stirred for 45 min at 0° C. then for 20 min at 23° C. The reaction mixture was then partitioned between DCM (50 mL) and saturated aqueous sodium bicarbonate (400 mL). The organic layer was separated, then washed successively with aqueous sodium bisulfite (63 g in 350 mL water) and saturated aqueous sodium bicarbonate (400 mL), then dried over magnesium sulfate, filtered and concentrated in vacuo. The residue was purified by MPLC using an ISCO COMBIFLASH brand flash chromatography purification system (330 g silica column) eluting with a 0-100% EtOAc in hexanes linear gradient over 16 column volumes at 200 mL/min. Product containing fractions were evaporated in vacuo to give Boc-1-ethyl-3-[6-fluoro-5-[2-(1-hydroxy-1-methyl-ethyl)pyrimidin-5-yl]-7-[(2R)-tetrahydrofuran-2-yl]-1H-benzimidazol-2-yl]urea dibenzyl phosphate (26) (11.92 g, 15.11 mmol, 64.09%). ESMS (M+1)=789.2; $^1$H NMR (300.0 MHz, CDCl$_3$) δ 9.51 (s, 1H), 9.03 (t, J=5.4 Hz, 1H), 8.91 (d, J=1.6 Hz, 2H), 7.73 (d, J=6.5 Hz, 1H), 7.37-7.28 (m, 10H), 5.58 (t, J=7.8 Hz, 1H), 5.17-5.05 (m, 4H), 4.23 (t, J=7.5 Hz, 1H), 4.05 (td, J=7.8, 4.3 Hz, 1H), 3.53-3.44 (m, 2H), 2.39 (dd, J=7.9, 14.5 Hz, 2H), 2.28-2.15 (m, 2H), 1.98 (s, 6H), 1.72 (m, 9H) and 1.31 (t, J=7.2 Hz, 3H) ppm.

EXAMPLE 26

Preparation of (R)-dibenzyl 2-(5-(2-(3-ethylureido)-6-fluoro-7-(tetrahydrofuran-2-yl)-1H-benzo[d]imidazol-5-yl)pyrimidin-2-yl)propan-2-yl phosphate (24)

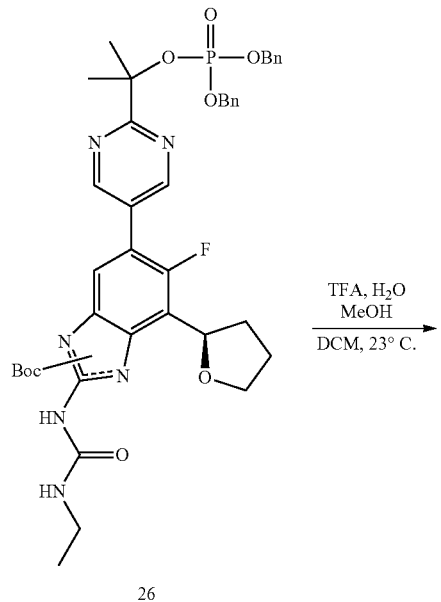

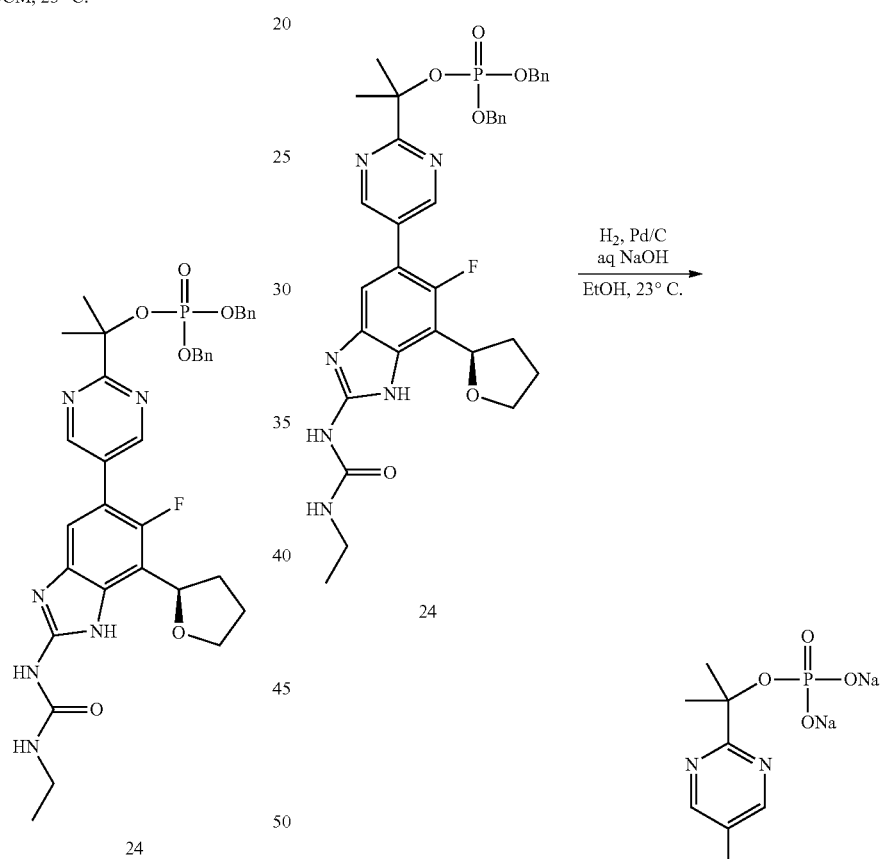

To a solution of Boc-1-ethyl-3-[6-fluoro-5-[2-(1-hydroxy-1-methyl-ethyl)pyrimidin-5-yl]-7-[(2R)-tetrahydrofuran-2-yl]-1H-benzimidazol-2-yl]urea dibenzyl phosphate (26) (11.9 g, 15.09 mmol) in DCM (300 mL) at 23° C. was added water (2.325 mL, 129.1 mmol) then TFA (3.441 g, 2.325 mL, 30.18 mmol). After 1 h, only partial conversion was observed by tlc, so more TFA (3.441 g, 2.325 mL, 30.18 mmol) was added. After a further 2.5 h, MeOH (2 mL) was added and the mixture stirred a further 18 hours. The reaction mixture was washed with 1:1 brine:saturated aqueous sodium bicarbonate (200 mL). The aqueous layer was re-extracted with DCM (150 mL), the organic layers combined, then dried (over magnesium sulfate), filtered and concentrated in vacuo. The resulting residue was re-dissolved in EtOAc (200 mL) washed with water (150 mL) and brine (100 mL), then dried (magnesium sulfate) filtered and concentrated to give (R)-dibenzyl 2-(5-(2-(3-ethylureido)-6-fluoro-7-(tetrahydrofuran-2-yl)-1H-benzo[d]imidazol-5-yl)pyrimidin-2-yl)propan-2-yl phosphate (24) (10.21 g, 14.83 mmol, 98.27%) as a white solid. ESMS (M+1)=689.4; $^1$H NMR (300 MHz, CD$_3$OD) δ 8.88 (d, J=1.6 Hz, 2H), 7.37 (d, J=6 Hz, 1H), 7.30 (m, 10H), 5.38-5.33 (m, 1H), 5.12-5.01 (m, 4H), 4.24 (dd, J=6.8, 14.9 Hz, 1H), 3.98 (dd, J=6.9, 15.1 Hz, 1H), 3.35-3.27 (m, 3H), 2.52 (q, J=5.9 Hz, 1H), 2.14-2.05 (m, 2H), 1.91 (s, 6H) and 1.22-1.14 (m, 3H) ppm.

EXAMPLE 27

Preparation of disodium (R)-2-(5-(2-(3-ethylureido)-6-fluoro-7-(tetrahydrofuran-2-yl)-1H-benzo[d]imidazol-5-yl)pyrimidin-2-yl)propan-2-yl phosphate (W)

A 1 L round bottom flask was charged with (R)-dibenzyl 2-(5-(2-(3-ethylureido)-6-fluoro-7-(tetrahydrofuran-2-yl)-1H-benzo[d]imidazol-5-yl)pyrimidin-2-yl)propan-2-yl phosphate (24) (9.37 g, 13.61 mmol), EtOH (300 mL), water (150 mL), Pd/C (10 wt % dry basis, wet, Degussa type, 3 g) and 1 M aqueous NaOH (27.22 mL, 27.22 mmol). The suspension was evacuated for 3 min (needle to pump) then placed under an atmosphere of hydrogen gas (balloon). After stirring 2.5 h at 23° C., the reaction was filtered through a 0.22 μm PES membrane (disposable Corning filter system, 1 L, polystyrene, #431098) to remove catalyst and washed with EtOH (50 mL). The resulting solution was concentrated, the residue dissolved in water (80 mL), treated with MeCN (80 mL), then frozen and lyophilized to give disodium (R)-2-(5-(2-(3-ethylureido)-6-fluoro-7-(tetrahydrofuran-2-yl)-1H-benzo[d]imidazol-5-yl)pyrimidin-2-yl)propan-2-yl phosphate (W) (7.10 g, 12.81 mmol, 94.12%) as a white solid. ESMS (M+1)=509.3; $^1$H NMR (300 MHz, D$_2$O) δ 8.58 (s, 2H), 6.92 (d, J=6.3 Hz, 1H), 5.13 (t, J=7.5 Hz, 1H), 3.98-3.81 (m, 2H), 3.04 (q, J=7.2 Hz, 2H), 2.26 (t, J=5.7 Hz, 1H), 1.97-1.92 (m, 2H), 1.67 (s, 6H) and 1.01 (t, J=7.2 Hz, 3H) ppm.

EXAMPLE 28

Preparation of diBoc-1-ethyl-3-[6-fluoro-5-[2-(1-hydroxy-1-methyl-ethyl)pyrimidin-5-yl]-7-[(2R)-tetrahydrofuran-2-yl]-1H-benzimidazol-2-yl]urea (28)

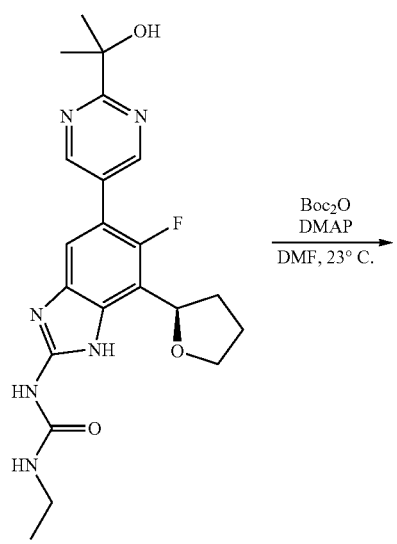

23

Boc$_2$O
DMAP
―――――→
DMF, 23° C.

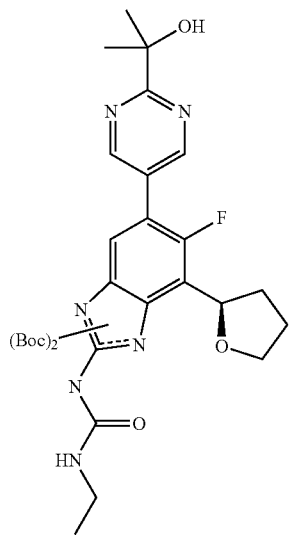

28

To a solution/suspension of 1-ethyl-3-[6-fluoro-5-[2-(1-hydroxy-1-methyl-ethyl)pyrimidin-5-yl]-7-[(2R)-tetrahydrofuran-2-yl]-1H-benzimidazol-2-yl]urea (23) (1.333 g, 1111 mmol) in DMF (30 mL) was added DMAP (38.01 mg, 0.3111 mmol) followed by Boc$_2$O (1.426 g, 1.501 mL, 6.533 mmol). After 30 min, the reaction mixture was diluted with water and EtOAc (300 mL each), the organic layer separated, washed with water and brine (300 mL each), then dried over magnesium sulfate, filtered and concentrated. The residue was purified by MPLC using an ISCO COMBIFLASH brand flash chromatography purification system (80 g silica column) eluting with a 0-60% EtOAc in hexanes linear gradient over 20 column volumes at 60 mL/min flow rate. Desired product fractions were combined and evaporated to give diBoc-1-ethyl-3-[6-fluoro-5-[2-(1-hydroxy-1-methyl-ethyl)pyrimidin-5-yl]-7-[(2R)-tetrahydrofuran-2-yl]-1H-benzimidazol-2-yl]urea (28) (1.43 g, 2.275 mmol, 73.11%) as a clear foam. ESMS (M+1)=629.3; $^1$H NMR (300.0 MHz, CDCl$_3$) δ 8.95 (d, J=1.6 Hz, 2H), 8.31-8.27 (m, 1H), 8.05 (d, J=6.5 Hz, 1H), 5.80-5.68 (m, 1H), 4.70 (s, 1H), 4.21-4.09 (m, 1H), 3.98 (d, J=6.4 Hz, 1H), 3.42-3.37 (m, 2H), 2.45-2.00 (m, 4H), 1.65 (s, 6H), 1.62 (s, 9H), 1.37 (s, 9H) and 1.28-1.21 (m, 3H) ppm.

EXAMPLE 29

Preparation of diBoc-1-ethyl-3-[6-fluoro-5-[2-(1-hydroxy-1-methyl-ethyl)pyrimidin-5-yl]-7-[(2R)-tetrahydrofuran-2-yl]-1H-benzimidazol-2-yl]urea dibenzyl phosphate (29)

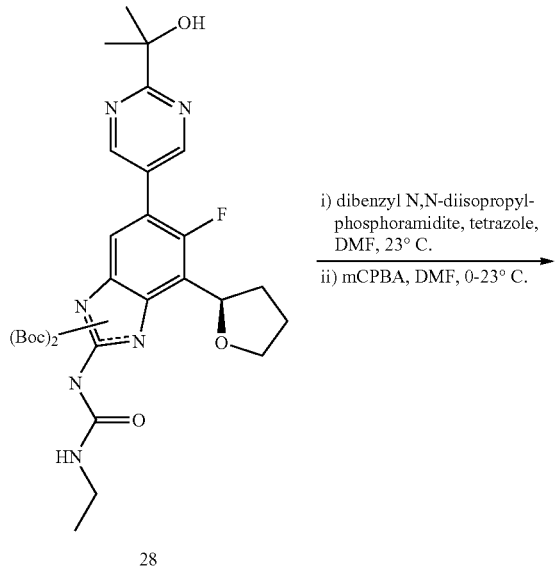

To diBoc-1-ethyl-3-[6-fluoro-5-[2-(1-hydroxy-1-methyl-ethyl)pyrimidin-5-yl]-7-[(2R)-tetrahydrofuran-2-yl]-1H-benzimidazol-2-yl]urea (28) (1.13 g, 1.797 mmol) and tetrazole (251.8 mg, 3.594 mmol) at 23° C. under $N_2$ was added DCM (30 mL) followed by N-dibenzyloxyphosphanyl-N-isopropyl-propan-2-amine (744.7 mg, 724.4 µL, 2.156 mmol). After stirring for 18 h, the reaction was cooled to 0° C. then treated with mCPBA (531.5 mg, 2.156 mmol). The reaction was stirred for 15 min at 0° C., then for 30 min at 23° C. The resulting solution was then partitioned between EtOAc and saturated aqueous sodium bicarbonate (300 mL each), the organic layer separated, then washed with 10% aqueous sodium bisulfite, saturated aqueous sodium bicarbonate and brine (300 mL each), then dried over magnesium sulfate filtered and concentrated. The residue was purified by MPLC using an ISCO COMBIFLASH brand flash chromatography purification system (80 g silica column) eluting with a 0-80% EtOAc in hexanes linear gradient over 20 column volumes at 60 mL/min flow rate. Desired product fractions were combined and evaporated to give diBoc-1-ethyl-3-[6-fluoro-5-[2-(1-hydroxy-1-methyl-ethyl)pyrimidin-5-yl]-7-[(2R)-tetrahydrofuran-2-yl]-1H-benzimidazol-2-yl]urea dibenzyl phosphate (29) (1.03 g, 1.159 mmol, 64.50%) as a clear, glassy oil. ESMS (M+1)=889.5; $^1$H NMR (300.0 MHz, CDCl$_3$) δ 8.93 (d, J=1.5 Hz, 2H), 8.31 (s, 1H), 8.04 (d, J=6.4 Hz, 1H), 7.36-7.26 (m, 10H), 5.83-5.70 (m, 1H), 5.16-5.05 (m, 4H), 4.24-4.18 (m, 1H), 4.03-3.97 (m, 1H), 3.42-3.36 (m, 2H), 2.43-2.05 (m, 4H), 1.98 (s, 6H), 1.64 (s, 9H), 1.40 (s, 9H) and 1.26 (t, J=7.2 Hz, 3H) ppm

EXAMPLE 30

Preparation of sodium (R)-2-(5-(2-(3-ethylureido)-6-fluoro-7-(tetrahydrofuran-2-yl)-1H-benzo[d]imidazol-5-yl)pyrimidin-2-yl)propan-2-yl phosphate (W)

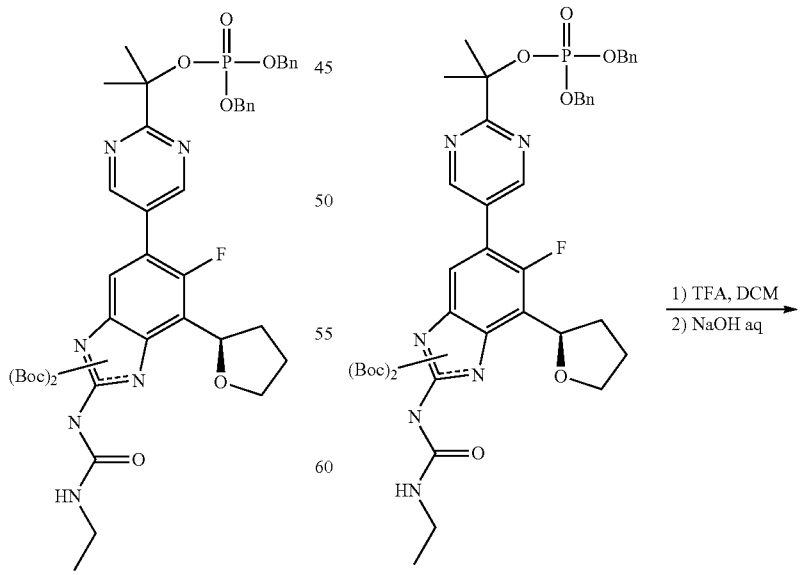

-continued

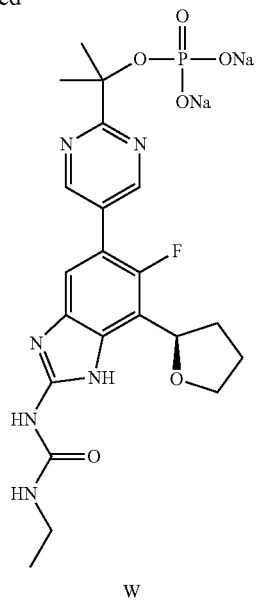

W

To a solution of diBoc-1-ethyl-3-[6-fluoro-5-[2-(1-hydroxy-1-methyl-ethyl)pyrimidin-5-yl]-7-[(2R)-tetrahydrofuran-2-yl]-1H-benzimidazol-2-yl]urea dibenzyl phosphate (29) (121 mg, 0.1361 mmol) in DCM (10 mL) at 23° C. was added TFA (5 mL). After 2 h, the reaction mixture was concentrated in vacuo. The residue was dissolved in MeOH (6 mL) and treated with approx 0.5 mL 2 M $NH_3$ in MeOH (to fully dissolve the material). The resulting solution was purified in 6 injections on preparative HPLC, reverse phase, Sunfire prep C18 OBD 5 μM column 19×100 mm; eluting with a 10-90% aq MeCN w/0.1% TFA buffer, linear gradient over 15 min at 20 mL/min flow rate. Fractions containing product were pooled and lyophilized. The resulting material was suspended in MeOH (3 mL), stirred at 23° C. for 30 min, then the precipitate was collected via filtration through a plastic frit. The resulting white solid was re-subjected to a MeOH slurry (3 mL), then collected via filtration to give 68 mg of white solid after drying. The white solid was treated with 0.10 M aq NaOH (2.68 mL, 2 equiv NaOH) to give a solution that was then passed through an Acrodisc CR 13 mm syringe filter with 0.45 μm PTFE membrane, flushing with water (2 mL). The resulting solution was treated with MeCN (3 mL), frozen and lyophilized to give sodium (R)-2-(5-(2-(3-ethylureido)-6-fluoro-7-(tetrahydrofuran-2-yl)-1H-benzo[d]imidazol-5-yl)pyrimidin-2-yl)propan-2-yl phosphate (W) as a white powder. ESMS (M+1)=509.2; $^1$H NMR (300 MHz, $D_2O$) δ 8.58 (s, 2H), 6.92 (d, J=6.3 Hz, 1H), 5.13 (t, J=7.5 Hz, 1H), 3.98-3.81 (m, 2H), 3.04 (q, J=7.2 Hz, 2H), 2.26 (t, J=5.7 Hz, 1H), 197-1.92 (m, 2H), 167 (s, 6H) and 1.01 (t, J=7.2 Hz, 3H) ppm.

EXAMPLE 31

Susceptibility Testing in Liquid Media

Compounds of this invention were tested for antimicrobial activity by susceptibility testing in liquid media. Such assays were performed within the guidelines of the latest CLSI document governing such practices: "M07-A8 Methods for Dilution Antimicrobial Susceptibility Tests for Bacteria that Grow Aerobically; Approved Standard—Eighth Edition (2009)". Other publications such as "Antibiotics in Laboratory Medicine" (Edited by V. Lorian, Publishers Williams and Wilkins, 1996) provide essential practical techniques in laboratory antibiotic testing. The specific protocols used were as follows:

Protocol 4. MIC Determination Procedure for *Mycobacterium* Species

Materials

Round bottom 96-well microtiter plates (Costar 3788) or similar

Film plate seals (PerkinElmer, TopSeal-A #6005250 or similar)

Middlebrook 7H10 broth with 0.2% glycerol

Middlebrook 7H10 agar with 0.2% glycerol

Middlebrook OADC Enrichment

Inoculum Preparation for *M. tuberculosis*:
1. Used prepared frozen *M. tuberculosis* stock stored at −70° C. *M. tuberculosis* was grown in 7H10 broth+10% OADC, then frozen at a concentration of 100 Klett or $5 \times 10^7$ cfu/ml,
2. Prepared a 1:20 dilution by removal of 1 ml of the frozen stock and added it to 19 ml of 7H10 broth+10% OADC (final concentration $2.5 \times 10^6$ cfu/ml).
3. From this dilution prepared a second 1:20 dilution, removed 1 ml and added it to 19 ml of fresh broth. This was the final inoculum to add to the 96-well plates.

Inoculum Preparation for *M. kansasii, M. avium, M. abscessus* and *Nocardia* spc.:
1. Used prepared frozen stock of culture or a fresh culture grown in 7H10 broth at a concentration of 10 Klett or $5 \times 10^7$/ml.
2. Prepared a 1:20 dilution by removing 1.0 ml of the culture stock and added it to 19 ml of 7H10 broth (final concentration $2.5 \times 10^6$ cfu/ml).
3. From this dilution prepared a 1:20 dilution, removed 1 ml and added it to 19 ml of fresh broth (final suspension).

Plate Preparation:
1. Labeled plates.
2. Added 50 μl of 7H10 broth+10% OADC to all wells being utilized for MIC determination using a multichannel electronic pipettor.
3. Prepared stock solutions of drugs (e.g. 1 mg/ml concentration) to be tested.
4. Thawed and diluted frozen stock solutions using 7H10 broth+10% OADC to obtain a working solution 4× the maximum concentration tested (e.g. final concentration 32 μg/ml, highest concentration tested was 8 μg/ml). Dilutions were made from the stock solution. To start at a concentration of 1 μg/ml, the drugs were prepared at 4 μg/ml, so the starting concentration was 1 μg/ml. Removed 25 μl of the 1 mg/ml stock and added to 6.2 ml of broth. All dilutions of drugs were done in broth.
5. Added 50 μl of the 4× working solution to the first well of the designated row. Continued for all compounds to be tested. Using a multichannel electronic pipettor, mixed 4× and serial diluted compounds through the 11th well. Discarded remaining 50 μl. Used the 12th well as the positive control.
6. Incubated plates at 37° C. *M. tuberculosis* for ~18 days; *M. avium* and *M. kansasii* for ~7 days; *Nocardia* and *M. abcessus* for ~4 days; with film seals.
7. Read visually and recorded the results. The MIC was recorded as the lowest concentration of drug where no growth was observed (optical clarity in the well).

Protocol 5. Protocol for *Mycobacterium tuberculosis* Serum Shift MIC Assay

Materials and reagents:
Costar #3904 Black-sided, flat-bottom 96-well microtiter plates
Middlebrook 7H9 broth (BD271310) with 0.2% glycerol
Middlebrook OADC Enrichment
Fetal Bovine Serum
Catalase (Sigma C1345)
Dextrose
$NaCl_2$
BBL Prompt Inoculation System (Fisher b26306)
Agar plates (Middlebrook 7H11 with 0.2% glycerol and OADC enrichment) with bacteria streaked to single colonies
Sterile DMSO Media Prep:
1. For serum shifted MICs, three different media were required which all had a base of 7H9+0.2% glycerol. It was important that all media and supplements were sterilized prior to MICs.
2. Prepared all media below and inoculated as described in next section. Tested all compounds against Mtb using each media.
   a. 7H9+0.2% glycerol+10% OADC ("standard" MIC media).
   b. 7H9+0.2% glycerol+2 g/L dextrose+0.85 g/L NaCl+ 0.003 g/L catalase (0% FBS).
   c. 2×7H9+0.2% glycerol+2 g/L dextrose+0.85 g/L NaCl+0.003 g/L catalase combined with equal volume Fetal Bovine Serum (50% FBS).

Inoculum Prep:
1. Using BBL Prompt, picked 5-10 well-separated colonies and inoculated 1 ml sterile saline that came in the kit. Typically plates were two to three weeks of age when used for this assay due to the slow growth of this organism in culture.
2. Vortexed well, then sonicated in water bath for 30 sec providing a suspension of ~$10^8$ cells/ml. Actual density could be confirmed by plating out dilutions of this suspension.
3. Prepared inoculum in each of the three media formulations by diluting the BBL Prompt suspension 1/200 (for example: transferred 0.2 ml of cells to 40 ml of medium) to obtain a starting cell density of ~$10^6$ cells/ml.
4. Used 100 μl cells (~$5 \times 10^4$ cells) to inoculate each microtiter well containing 1 μl of drug in DMSO (see below).

Drug Dilutions, Inoculation, MIC Determination:
1. Control drug stocks Isoniazid and Novobiocin were prepared at 10 mM in 100% DMSO while Ciprofloxacin and Rifampin were prepared at 1 mM in 50% DMSO and 100% DMSO, respectively. Prepared dilutions-dispensed 100 μL of the stock solution into the first column of a 96-well plate. Prepared 11-step, 2-fold serial dilutions across the row for each compound by transferring 50 μl from column 1 into 50 μl of DMSO in column 2. Continued to transfer 50 μL from column 2 through column 11 while mixing and changing tips at each column. Left column 12 with DMSO only as a control.
2. Transferred 1 μl of each dilution into an empty microtiter well prior to the addition of 100 μl of cells. The starting concentration of Isoniazid and Novobiocin was 100 μM after the dilution into medium+cells; the starting concentration of Ciprofloxacin and Rifampin was 10 μM after the dilution into medium+cells. Compound concentrations decreased in 2× steps moving across the rows of the microtiter plate. All MICs were done in duplicate at each of the three medium conditions.
3. Test sets of compounds were typically at 10 mM and 50 μL volume.
4. Used a multichannel pipettor, removed all of the volume from each column of the master plate and transferred into the first column of a new 96-well microtiter plate. Repeated for each column of compounds on master plate, transferring into column 1 of a new 96-well plate.
5. As described above for control compounds, generated 2-fold, 11-point dilutions of each compound using DMSO as diluent. In all cases, left column 12 as DMSO only for a control. Once all dilutions were complete, again transferred 1 μl of each dilution into an empty microtiter well prior to the addition of 100 μl of cells as done for the control compounds.
6. All wells were inoculated with 100 μl of diluted cell suspension (see above).
7. After inoculum addition, mixed plates by gently tapping sides of plate.
8. Plates were incubated in a humidified 37° C. chamber for 9 days.
9. At 9 days added 25 μl 0.01% sterile resazurin to each well. Measured background fluorescence at Excitation 492 nm, Emission 595 nm and returned the plate to the incubator for another 24 hours.

After 24 hours the fluorescence of each well was measured at Excitation 492 nm, Emission 595 nm.

Percent inhibition by a given compound was calculated as follows: Percent inhibition=100−([well fluorescence−average background fluorescence]/[DMSO control−average background fluorescence]×100). MICs were scored for all three medium conditions as the lowest compound concentration that inhibited resazurin reduction ('%−inhibition') signal ≥70% at a given medium condition.

Table 7 shows the results of the MIC assay for selected compounds of this invention.

In Table 7 and in subsequent Tables and Examples, "Compound 12" corresponds to 1-ethyl-3-[5-[2-(1-hydroxy-1-methyl-ethyl)pyrimidin-5-yl]-7-[(2R)-tetrahydrofuran-2-yl]-1H-benzimidazol-2-yl]urea and "Compound 13" relates to the mesylate salt of Compound 12. Similarly, "Compound 23" corresponds to 1-ethyl-3-[6-fluoro-5-[2-(1-hydroxy-1-methyl-ethyl)pyrimidin-5-yl]-7-[(2R)-tetrahydrofuran-2-yl]-1H-benzimidazol-2-yl]urea and "Compound 23A" relates to the mesylate salt of Compound 23. These are the same numbers used to identify said compounds and salts as used in the Examples above.

TABLE 7

MIC Values of Selected Compounds

| | | MIC (μg/ml) | |
|---|---|---|---|
| Strain/Special Condition | Protocol | Compound 13 | Compound 23A |
| *Mycobacterium avium* 103 | 4 | 0.47 | 0.18 |
| *M. avium* Far | 4 | 0.94 | 0.23 |
| *M. avium* 3404.4 | 4 | 0.94 | 0.23 |
| *M. kansasii* 303 | 4 | Not Done | 0.03 |
| *M. kansasii* 316 | 4 | Not Done | 0.06 |
| *M. kansasii* 379 | 4 | Not Done | <0.015 |
| *M. tuberculosis* H37Rv ATCC 25618 | 4 | 0.37 | 0.015 |
| *M. tuberculosis* Erdman ATCC 35801 | 4 | 0.25 | 0.06 |
| *M. tuberculosis* Erdman ATCC 35801 | 5 | 0.045 | 0.03 |
| *M. tuberculosis* Erdman ATCC 35801 with Mouse Serum | 5 | 2 | 0.5 |
| *M. abscessus* BB2 | 4 | Not Done | 1 |

TABLE 7-continued

MIC Values of Selected Compounds

| Strain/Special Condition | Protocol | MIC (µg/ml) | |
| --- | --- | --- | --- |
| | | Compound 13 | Compound 23A |
| M. abscessus MC 6005 | 4 | Not Done | 1 |
| M. abscessus MC 5931 | 4 | Not Done | 0.5 |
| M. abscessus MC 5605 | 4 | Not Done | 1.5 |
| M. abscessus MC 6025 | 4 | Not Done | 0.75 |
| M. abscessus MC 5908 | 4 | Not Done | 1.5 |
| M. abscessus BB3 | 4 | Not Done | 0.5 |
| M. abscessus BB4 | 4 | Not Done | 2 |
| M. abscessus BB5 | 4 | Not Done | 0.5 |
| M. abscessus MC 5922 | 4 | Not Done | 0.25 |
| M. abscessus MC 5960 | 4 | Not Done | 0.5 |
| M. abscessus BB1 | 4 | Not Done | 2 |
| M. abscessus MC 5812 | 4 | Not Done | 1 |
| M. abscessus MC 5901 | 4 | Not Done | 1 |
| M. abscessus BB6 | 4 | Not Done | 0.5 |
| M. abscessus BB8 | 4 | Not Done | 0.5 |
| M. abscessus MC 5908 | 4 | Not Done | 1 |
| M. abscessus LT 949 | 4 | Not Done | 1 |

TABLE 7-continued

MIC Values of Selected Compounds

| Strain/Special Condition | Protocol | MIC (µg/ml) | |
| --- | --- | --- | --- |
| | | Compound 13 | Compound 23A |
| M. abscessus BB10 | 4 | Not Done | 0.015 |
| M. abscessus MC 6142 | 4 | Not Done | 0.5 |
| M. abscessus MC 6136 | 4 | Not Done | 0.5 |
| M. abscessus MC 6111 | 4 | Not Done | 0.5 |
| M. abscessus MC 6153 | 4 | Not Done | 1 |

EXAMPLE 32

Seven-Day Oral (Gavage) Toxicity and Toxicokinetics Study in Rats

The objectives of this study were: 1) to evaluate the potential toxicity of Compound 13 and Compound 23A when administered orally by gavage to male rats for 7 consecutive days and 2) to assess the toxicokinetics of Compound 13, and Compound 23A after the first and seventh doses.

Animals

Species, Source, History, and Justification

Crl:CD(SD) rats were obtained from Charles River Laboratories of Stone Ridge, N.Y. The animals were laboratory bred and experimentally naïve. Rats were chosen because they are a species that is commonly used for nonclinical toxicity evaluations.

Number, Sex, Age, and BodyWeightRange

Forty rats (20 noncannulated males and 20 males with jugular vein cannulas) were ordered. From these animals, 15 noncannulated males and 15 cannulated males were used. Animals were as uniform in age as possible. The rats were prepubertal to young adult, approximately 9 weeks of age at initiation of dosing. Their supplier-calculated birth date was retained in the study records. The weight range for the animals at the time of allocation to groups was 218.5-306.3 g.

Study Design

The rats were assigned as shown in the Table 8 below. Animals received the test article or vehicle by oral gavage for 7 consecutive days and were terminated the day following completion of dosing. The first day of dosing was designated as Day 1 of the study. The animals were evaluated for changes in clinical signs, body weight, and other parameters as described below.

TABLE 8

Group Assignment and Dose Levels

| Dose Group | No. Animals (M) Main Study | No. Animals (M) Toxicokinetics | Test Article | Dose Level (mg/kg/day) | Doses per Day | Dose Concentration (mg/mL) | Dose Volume (mL/kg) | Animals for Necropsy (Day 8) |
| --- | --- | --- | --- | --- | --- | --- | --- | --- |
| A | 3 | 0 | Vehicle | 0 | 1 | 0 | 10 | 3 |
| B | 3 | 3 | Compound 13 | 100 | 1 | 10 | 10 | 6 |
| C | 3 | 3 | Compound 13 | 200 | 1 | 20 | 10 | 6 |
| D | 3 | 3 | Compound 23A | 100 | 1 | 10 | 10 | 6 |
| E | 3 | 3 | Compound 23A | 300 | 2 | 30 | 10 | 6 |
| F | 0 | 3 | Vehicle | 0 | 2 | 0 | 10 | 3 |

Route/Dose

The vehicle and test article were administered by oral gavage once daily for 7 consecutive days at a dose volume of 10 mL/kg body weight for Group A and Groups B-D, respectively. The test article and vehicle were administered by oral gavage twice daily, approximately 8 hours apart, for 7 consecutive days at a dose volume of 10 mL/kg body weight for Group E and Group F, respectively. The actual volume administered to each animal was calculated and adjusted based on the most recent body weight of each animal.

In-Life Observations and Measurements

Observations

Animals were observed for viability at least once in the morning and once in the afternoon, at least 4 hours apart, throughout the study. During the treatment period, daily cageside observations were made and recorded predose and postdose (following the first dose only). The postdosing observations made during treatment occurred at the following times based on $C_{max}/T_{max}$ for the two compounds from previous studies:

1 hour postdose for Groups A-F.

One cageside observation was made on the day of necropsy.

Unscheduled Observations

Any findings observed at times other than scheduled observation times were to be recorded on an unscheduled observation or in Provantis; however, no abnormalities were observed throughout the study. Provantis is an electronic data collection, management and reporting system that is commonly used in the art.

Body Weights

Prior to start of dosing, body weights were measured for randomization on Day 1. During the treatment, body weights were measured on Day 1 and Day 7. In addition, fasted body weights were measured prior to necropsy for calculation of organ/body weight ratios.

Food Consumption

Throughout the study, food consumption was measured daily starting 3 days prior to start of dosing.

Clinical Pathology Evaluation

Blood samples for evaluation of hematology, coagulation, and serum chemistry parameters were collected from all animals from the retro-orbital plexus (under $CO_2/O_2$ anesthesia, for the main study animals) or jugular vein cannula (for the toxicokinetic animals) prior to necropsy. Due to residual heparin used to keep the cannulas patent for the toxicokinetic animals, coagulation samples from these rats, were not able to be analyzed. The animals were fasted overnight prior to blood collection. On the day of blood collection for clinical pathology analyses, the animals were not necropsied until after the blood was collected and the samples judged to be acceptable by the clinical pathology group.

Hematology

An appropriate amount of blood was collected in EDTA-containing tubes. The whole blood samples were analyzed for the parameters indicated below in Table 9.

TABLE 9

| Whole Blood Parameters | |
| --- | --- |
| Red blood cells (RBC) (count and morphology) | Mean corpuscular volume (MCV) |
| White blood cells (WBC) (total and differential) | Mean corpuscular hemoglobin (MCH) |
| Hemoglobin concentration (HGB) | Mean corpuscular hemoglobin concentration (MCHC) |
| Hematocrit (HCT) | Platelet count (PLAT) |
| Reticulocyte count (ABSRET) | Mean platelet volume (MPV) |

Coagulation

An appropriate amount of blood was collected in tubes containing sodium citrate and then centrifuged to obtain plasma for the determination of prothrombin time (PT) and activated partial thromboplastin time (APTT).

Serum Chemistry

An appropriate amount of blood was collected in tubes without anticoagulant. The sample was allowed to clot and then was centrifuged to obtain serum. The serum was analyzed for the parameters indicated below in Table 10.

TABLE 10

| Serum Parameters | |
| --- | --- |
| Sodium (NA) | Calcium (CA) |
| Potassium (K) | Inorganic phosphorus (PHOS) |
| Chloride (CL) | Glucose (GLU) |
| Total bilirubin (TBILI) | Urea nitrogen (BUN) |
| Alkaline phosphatase (ALKP) | Total protein (TPRO) |
| Lactate dehydrogenase (LDH) | Albumin (ALB) |
| Aspartate aminotransferase (AST) | Globulin (GLOB) |
| Alanine aminotransferase (ALT) | Albumin/globulin ratio (A/G) |
| Gamma-glutamyltransferase (GGT) | Cholesterol (CHOL) |

TABLE 10-continued

| Serum Parameters | |
| --- | --- |
| Creatine phosphokinase (CK) | Triglycerides (TRIG) |
| Creatinine (CREA) | |

Toxicokinetics

On the $1^{st}$ and $7^{th}$ day of dosing, blood samples (approximately 0.5 mL/sample) were collected from the jugular vein cannula for all toxicokinetic animals at the timepoints listed below into $K_3$EDTA-containing tubes. Toxicokinetic animals from the control group (Group F) only had a single blood collection sampling from each collection day at the 1-hour timepoint (following the first dose administration of the day). Prior to each collection, a small sample of blood (with heparin blocking solution) was removed from the cannula and discarded. A new syringe was placed on the cannula, and the protocol-required sample was taken. The syringe with the blood sample was removed, and a new syringe with saline attached to the cannula. Blood volume was replaced with an equal volume of saline and then blocking solution placed in the cannula. Each animal was returned to its cage until the next collection timepoint.

All samples collected during this study were placed in labeled containers. Each label contained the following information: 1) Study number, 2) Animal number, 3) collection interval, 4) Group and Sex, and 5) Date of collection.

The blood samples were mixed immediately by inverting, then placed on wet ice and centrifuged cold (~1500 g, ~10 minutes, ~5° C.) to obtain plasma. The plasma was split into 96-well 1.4-mL polypropylene tubes with pierceable TPE capcluster certified RNase, DNase free caps as2 aliquots and stored frozen (≤−70° C.).

TABLE 11

| Sample Collection Timepoints | |
| --- | --- |
| Timepoint | Window[1] |
| Predose | Predose |
| 1 h | ±4 min |
| 2 h[2] | ±5 min |
| 4 h | ±5 min |
| 8 h[3] | ±5 min |
| 12 h | ±10 min |
| 24 h | ±20 min |
| 48 h[4] | ±40 min |

[1]All samples were collected within the collection window.
[2]Following Day 1 dosing only.
[3]Obtained from Groups E and F prior to PM dose administration.
[4]Following Day 7 dosing only.

Termination

No animal was deemed moribund during the study. All study animals were euthanized and subjected to a necropsy following the protocol-prescribed number of days of treatment. All animals were terminated by exsanguination (severing the abdominal aorta while under deep $CO_2/O_2$ anesthesia).

Necropsy

A necropsy with tissue collection was conducted on all animals terminated during the study. The necropsy included examination of: carcass and muscular/skeletal system; all external surfaces and orifices; cranial cavity and external surface of the brain; neck with associated organs and tissues; and thoracic, abdominal, and pelvic cavities with their associated organs and tissues.

All abnormalities were described and recorded.

Organ Weights

For all animals euthanized at scheduled necropsies, the kidneys, liver, and prostate gland were weighed. Following weighing, an approximate 1 gram sample of liver and kidney was weighed, transferred to Precellys 7 mL CK28 Tissue Homogenizing tubes (Cat. No. 0904-01), snap-frozen, and analyzed.

Organ/body ratios were calculated using the terminal fasted body weight obtained prior to necropsy.

Tissue Preservation and Bone Marrow Collection

The tissues and organs indicated below in Table 12 were collected from all animals and were preserved in 10% neutral-buffered formalin with the exception of the testes, epididymides, and eyes. Testes, epididymides, and eyes with optic nerve attached were fixed in Modified Davidson's Solution for ~24-48 hours, rinsed with water, and then transferred to 10% neutral-buffered formalin for storage.

TABLE 12

Tissue Collection

| Tissue | Submitted at Necropsy | Organ Weight | Histopathology |
|---|---|---|---|
| Animal ID | X | | |
| Adrenal gland (2) | X | | |
| Aorta | X | | |
| Artery, mesenteric | X | | |
| Bone (femur) | X | | |
| Bone marrow (sternum) | X | | |
| Brain | X | | |
| Epididymides (2) | X | | |
| Esophagus | X | | |
| Eyes (2) | X | | |
| Gross lesions | X | | |
| Heart | X | | |
| Intestine, cecum | X | | |
| Intestine, colon | X | | |
| Intestine, duodenum | X | | |
| Intestine, jejunum | X | | |
| Intestine, ileum | X | | |
| Intestine, rectum | X | | |
| Kidneys (2) | X | X | X |
| Liver | X | X | X |
| Lungs | X | | |
| Lymph node, mandibular | X | | |
| Lymph node, mesenteric | X | | |
| Mammary gland | X | | |
| Nerve, optic | X | | |
| Nerve, sciatic | X | | |
| Parathyroid gland (2)[a] | X | | |
| Pancreas | X | | |
| Pituitary | X | | |
| Prostate | X | X | X |
| Seminal vesicles | X | | |
| Skeletal muscle (biceps femoris) | X | | |
| Skin (abdominal) | X | | |
| Spinal cord, cervical | X | | |
| Spinal cord, thoracic | X | | |
| Spinal cord, lumbar | X | | |
| Spleen | X | | |
| Stomach | X | | |
| Testes (2) | X | | |
| Thymus | X | | |
| Thyroid gland (2)[a] | X | | |
| Tongue | X | | |
| Trachea | X | | |
| Urinary bladder | X | | |

[a]Thyroid weighed with parathyroids attached.

Histopathology

For all animals scheduled for the terminal necropsy, the kidneys, liver, and prostate were embedded in paraffin, sectioned and stained with hematoxylin and eosin for further examination by light microscopy. For Groups A, D, E, and F only, the remaining tissues listed above were embedded in paraffin, sectioned and stained with hematoxylin and eosin for further examination by light microscopy.

Statistical Analysis

Where appropriate, numeric animal data were evaluated statistically.

For comparative statistics, Group A (control group) was compared to Groups B and C (treated groups, dosed QD) and Group F (control group, dosed BID) was compared to Group E (treated group, dosed BID). Data were evaluated using the Levene Test for homogeneity of variances and the Shapiro-Wilks Test for normality of distributions, with significance at $p \leq 0.05$. Data determined to be homogeneous and of normal distribution were evaluated by analysis of variance (ANOVA). If the ANOVA verified significance at $p \leq 0.05$, pairwise comparisons of each treated group with the respective control group were made using a parametric test (Dunnett Test) to identify statistical differences ($p \leq 0.05$). Data determined to be nonhomogeneous or of nonnormal distribution were evaluated using a Kruskal-Wallis Test for group factor significance. If significance ($p \leq 0.05$) existed between groups, a nonparametric test (Wilcoxonwith Bonferroni-Holm), was used to compare treatment groups to the control group. Food consumption data from animals where spillage occurred was excluded from the applicable time period. Comparative statistics of food consumption data were limited to the Dunnett Test (parametric). Statistics were not performed on pretest food consumption (Day 4 to Day 1).

Results

The exposures for different dosage levels of Compound 23A and Compound 13 were dose related. No adverse observations or effects on mean body weight were observed in animals treated with either Compound 13 or Compound 23A. Mean food consumption was reduced during different intervals of the study for animals treated once daily with Compound 13 (100 or 200 mg/kg) and twice daily with Compound 23A (300 mg/kg). However, as the decreased food consumption was not correlated with body weight changes in the Compound 13 and Compound 23A groups, these effects were not considered to be adverse or biologically significant. The mean calcium ion concentration (CA) was statistically lower, while the mean ALT and the AST for the group of rats administered 300 mg/kg Compound 23A twice a day were statistically higher when compared to the controls treated twice a day. No test article-related histopathological findings were noted for animals receiving either Compound 13 or Compound 23A at any dose regimen.

Within the scope of this study and based on the absence of changes in body weight, clinical pathology, and histopathology, the NOEL (No-Observable-Effect-Level) for Compound 13 administered to male rats once a day for 7 days orally via gavage was 200 mg/kg (844 µg*hr/ml Day 7 AUC), while the NOEL for Compound 23A administered once a day was 100 mg/kg (82 µg*hr/ml AUC). The NOAEL (No-Observable-Adverse-Effect-Level) for Compound 23A administered to male rats twice a day for 7 days orally via gavage was 300 mg/kg (291 µg*hr/ml AUC).

Therefore, Compounds 13 and 23A did not demonstrate adverse toxicity within the scope of the study at dose levels up to 200 mg/kg/day and 600 mg/kg/day, respectively.

EXAMPLE 33

An Oral Range Finding Toxicity and Toxicokinetic Study in Male Cynomolgus Monkeys The objectives of this study were 1) to evaluate the potential toxicity of Compound 23 when administered orally by gavage to male Cynomolgus monkeys for 7 consecutive days; and 2) to assess the toxicokinetics of Compound 23 after the first and seventh doses.

Animals

Species, Source, History, and Justification

Cynomolgus monkeys (Macaca Fascicularis) were obtained from Primus Bio-Resources Inc. of PinCourt, Quebec, Canada. Cynomolgus monkeys were chosen because they are a non-rodent species that is commonly used for nonclinical toxicity evaluations.

Number, Sex, Age, and Body Weight Range

Eight (2 naive and 6 non-naïve) males were used in the study. The animals were young adults and weighed between 2 to 4 kg at the onset of dosing.

Study Design

The animals were assigned as shown in Table 13 below. Animals received Compound 23 or vehicle by oral gavage once per day for 7 consecutive days and were terminated the day following completion of dosing. The first day of dosing was designated as Day 1 of the study. The actual volume administered to each animal was calculated and adjusted based on the most recent body weight of each animal.

TABLE 13

Group Assignment and Dose Levels

| Group | Dose Level (mg/kg) | Dose Concentration (mg/mL) | Dose Volume (mL/kg) | Number of animals |
|---|---|---|---|---|
| 1 | Control* | 0 | 5 | 2 |
| 2 | 50 | 10 | 5 | 2 |
| 3 | 100 | 20 | 5 | 2 |
| 4 | 200 | 40 | 5 | 2 |

*The Control animals received the control/vehicle (20% captisol/1% HPMCAS/1% PVP in 0.01M KCl/HCL buffer) alone In-Life Observations and Measurements Observations Cage-side clinical signs (ill health, behavioral changes etc.) were recorded at least once daily during the study.

Body Weights

Body weights were recorded for all animals prior to group assignment and on Days 1 (prior to dosing), 3 and 7 as well as terminally prior to necropsy (fasted).

Electrocardiography (ECG)

Electrocardiograms (bipolar limb leads I, II and III, and augmented unipolar leads aVR, aVL and aVF) were obtained for all monkeys once during the pre-treatment period and again on Day 7 (post-dosing).

The tracings were assessed for gross changes indicative of cardiac electrical dysfunction. The potential presence of abnormalities involving heart rate (lead II), sinus and atrio-ventricular rhythm or conductivity were determined. Heart rate, PR interval, QRS duration, QT and QTc intervals values were measured.

Toxicokinetics

A series of 7 blood samples (approximately 0.5 mL each) were collected from each monkey on Days 1 and 7 at the following time points: predose, 30 minutes and 2, 3, 6, 12 and 24 hours post-dose. For this purpose, each monkey was bled by venipuncture and the samples were collected into tubes containing the anticoagulant, K2EDTA. Tubes were placed on wet ice until ready for processing.

Clinical Pathology

Laboratory investigations (hematology, coagulation, clinical chemistry and urinalysis) were performed on all animals prior to start of treatment and prior to termination on Day 8.

Blood samples were collected by venipuncture following an overnight period of food deprivation consisting of at least 12 hours but no more than 20 hours. Urine was collected from animals deprived of food and water, overnight (at least 12 hours but no more than 20 hours).

Hematology

The following parameters were measured on blood samples collected into EDTA anticoagulant: red blood cell count, mean corpuscular hemoglobin (calculated), hematocrit (calculated), mean corpuscular volume, hemoglobin, morphology of cells, white blood cell count, platelet count, white blood cell differential (absolute), reticulocyte (absolute and percentage) and mean corpuscular hemoglobin concentration (calculated).

Coagulation

Activated partial thromboplastin time and prothrombin time were measured on blood samples collected into citrate anticoagulant.

Clinical Chemistry

The following parameters were measured on blood samples collected into tubes containing clotting activator: a/g ratio (calculated), creatinine, alanine aminotransferase, globulin (calculated), albumin, glucose, alkaline phosphatase, phosphorus (inorganic), aspartate aminotransferase, potassium, bilirubin (total), sodium, calcium, total protein, chloride, triglycerides, cholesterol (total), urea, gamma glutamyltransferase and sorbitol dehydrogenase.

Urinalysis

The following parameters were measured on urine samples: bilirubin, protein, blood, sediment microscopy, color and appearance, specific gravity, glucose, urobilinogen, ketones, volume and pH.

Termination

All animals were euthanized upon completion of the treatment period on Day 8 following an overnight period without food. The monkeys were pre-anesthetized with Ketamine and then euthanized by an intravenous overdose of sodium pentobarbital followed by exsanguination by transsection of major blood vessels.

Necropsy

A necropsy with tissue collection was conducted on all animals terminated during the study. The necropsy included examination of:

carcass and muscular/skeletal system;

all external surfaces and orifices;

cranial cavity and external surface of the brain;

neck with associated organs and tissues; and thoracic, abdominal, and pelvic cavities with their associated organs and tissues.

All abnormalities were described and recorded.

Tissue Preservation

On completion of the gross examination and selected organ weighing, the tissues and organs were retained as noted below in Table 14. Neutral buffered 10% formalin was used for fixation and preservation unless otherwise indicated.

TABLE 14

Tissue and Organ Retention

| ORGANS/TISSUES | Retain(•) | Weigh (✓) | Examine (ϵ) |
|---|---|---|---|
| Adrenals | • | ✓ | ϵ |
| Animal identification | • | | |
| Aorta (thoracic) | • | | ϵ |
| Blood | | | |
| Bone marrow smears (3) | • | | |
| Brain | • | ✓ | ϵ |
| Cecum | • | | ϵ |
| Colon | • | | ϵ |
| Epididymides | •d | | ϵ |
| Esophagus | • | | ϵ |
| Eyes | •a | | ϵ |
| Femur & marrow | • | | ϵ |
| Gallbladder | • | | ϵ |
| Heart | • | ✓ | ϵ |
| Kidneys | • | ✓ | ϵ |
| Liver (2 lobes) | • | ✓ | ϵ |
| Lungs (2 lobes) | •b | ✓c | ϵ |
| Lymph Node, mandibular | • | | ϵ |
| Lymph Node, mesenteric | • | | ϵ |
| Mammary gland (thoracic) | • | | ϵ |
| Optic nerves | •a | | ϵ |
| Pancreas | • | | ϵ |
| Pituitary | • | ✓ | ϵ |
| Prostate | • | ✓ | ϵ |
| Rectum | • | | ϵ |
| Salivary Gland, mandibular | • | | ϵ |
| Sciatic nerve | • | | ϵ |
| Seminal vesicles | • | | ϵ |
| Skeletal muscle | • | | ϵ |
| Skin & subcutis (thoracic) | • | | ϵ |
| Duodenum | • | | ϵ |
| Jejunum | • | | ϵ |
| Ileum | • | | ϵ |
| Spinal Cord, cervical | • | | ϵ |
| Spleen | • | ✓ | ϵ |
| Sternum & marrow | • | | ϵ |
| Stomach | • | | ϵ |
| Testes | •d | ✓ | ϵ |
| Thymus | • | ✓ | ϵ |
| Thyroid gland/parathyroids | • | ✓ | ϵ |
| Tongue | • | | ϵ |
| Trachae | •c | | ϵ |
| Urinary bladder | • | | ϵ |
| Abnormal findings | • | | | aDavidson's fluid used for fixation and preservation
bLungs were infused with 10% neutral buffered formalin used for fixation and preservation
cLungs were weighed with trachea
dBouin's fluid used for fixation and preservation
ϵ Examined microscopically Histopathology For all animals, all tissues indicated above were embedded in paraffin, sectioned and stained with hematoxylin and eosin and examined by light microscopy.

Results

The exposures for different dosage levels of Compound 23 were dose related.

There were no clinical signs, or changes in body weights, electrocardiography parameters, clinical pathology parameters, or organ weights that could be attributed to the administration of Compound 23 at doses up to 200 mg/kg/day. Similarly, there were no macroscopic or microscopic findings that could clearly be attributed to the administration of Compound 23 at doses up to 200 mg/kg/day. The no observed effect level (NOEL) for Compound 23 in male Cynomolgus monkeys was determined to be 200 mg/kg/day.

EXAMPLE 34

Pharmacokinetic Studies

The pharmacokinetic parameters of selected compounds of this invention were determined in the experiments described below. General analytic procedures and specific experimental protocols were employed as follows:

General Analytic Procedures

The following general analytic procedures were employed in the pharmacokinetic experiments described below:

Sample Analysis. Concentrations of Compound 23 and Compound W in plasma were determined using a high performance liquid chromatography/tandem mass spectrometry (HPLC/MS/MS) method. Before extraction, plasma samples were diluted using blank plasma 2-, 4-, 5-, or 10-fold, as necessary, depending on the dose level or formulation. Compound 23 and Compound W along with the internal standard (1S) were extracted from (diluted) plasma, 100 µL each, by direct protein precipitation with acetonitrile (1:4 ratio of plasma/acetonitrile). After centrifugation, the supernatant extract (10 µL) was injected onto the LC/MS/MS system. The HPLC system included a Waters Xterra MS C18 column, 5 micron, 2.1 mm diameter×50 mm long eluted with a gradient mobile phase consisting of 0.1% formic acid in water or in acetonitrile.

The analytes were detected by MS/MS with Atmospheric Pressure Chemical Ionization (APCI) in the mode of multiple reaction monitoring (MRM). The lower limit of quantitation (LLOQ) was 1, 2, 4, 5, 10, or 20 ng/mL, depending on the sample dilution factor. The linear range of the assay was from 1 to 5000 ng/mL. The intra-day and inter-day assay accuracy was within 2% of the nominal values. The intra- and inter-day assay variability was <10%.

Samples of the dose suspension formulation of Compound W were assayed with an HPLC/UV method after 10-fold to 500- or 1000-fold of dilution with DMSO: acetonitrile:water (33:33:33) depending on the dose level or formulation. Samples of the dose solution formulation of Compound W were assayed with an HPLC/UV method after 10-, 50-, 100 or 500-fold of dilution with DMSO:water (50:50) depending on the dose level or formulation.

Pharmacokinetic Data Analysis. Plasma concentration-time profiles of Compound 23 and Compound W were analyzed by noncompartmental pharmacokinetic methods using WinNonlin® Professional Edition software, Version 5.1.1 (Pharsight Corporation, Mountain View, Calif.).

Key pharmacokinetic parameters including $AUC_{all}$, $AUC_{extrap}$, $C_{max}$, $t_{max}$, Cl_obs, Vss_obs and $t_{1/2}$ were determined.

Statistical Data Analysis. Descriptive statistical data of plasma concentrations and pharmacokinetic parameter estimates were calculated, including the mean, standard deviation (SD), and coefficient of variation (% CV) using WinNonlin software, Version 5.1.1 or Microsoft Excel 2000.

Monkey Oral Study

Malecynomolgus monkeys (n=3 per dose group) were administered single nominal PO doses of 3, 30 and 300 mg/kg of Compound W by gavage. Compound W was formulated in 0.5% MC (microcrystalline cellulose). Animals had free access to food and water before and after dosing.

Blood samples (approximately 0.25 mL each) were collected via a carotid artery catheter prior to dosing and at 0 (predose), 0.25, 0.5, 1, 2, 3, 4, 6, 8, 12, 24, 48 hours post dose. Each blood sample was collected into a tube that was kept on wet ice and contained potassium EDTA as the anticoagulant. Plasma was separated and stored at approximately −70° C. until analysis.

Plasma samples were analyzed using a liquid chromatography/tandem mass spectrometry (LC/MS/MS) method to determine the concentrations of Compound 23 and Compound W with a lower limit of quantitation (LLOQ) of 1 to 20 ng/mL, depending on the sample dilution factor. Plasma concentration vs. time data was subjected to noncompartmental pharmacokinetic (PK) analysis. The results of this analysis are provided in Table 15.

TABLE 15

Pharmacokinetic Data from Monkey Oral Study

| Dose (mg/kg) | Route | Formulation | Analyte | Cmax (ug/ml) | AUX (ug * hr/ml) | AUCextrap (ug * hr/ml) | Tmax (hr) | t1/2 (hr) |
|---|---|---|---|---|---|---|---|---|
| 30 | PO | 0.5% MC | Compound 23 | 14.4 | 24.7 | 24.8 | 1.7 | 13.9 |
| 100 | PO | 0.5% MC | Compound 23 | 20.9 | 76.7 | 76.9 | 2.3 | 8.3 |
| 300 | PO | 0.5% MC | Compound 23 | 23.8 | 155.1 | 155 | 1.2 | 5.6 |
| 30 | PO | 0.5% MC | Compound W | 0.0264 | 0.0453 | 0.206 | 0.83 | — |
| 100 | PO | 0.5% MC | Compound W | 0.322 | 0.432 | 0.437 | 0.67 | 5.31 |
| 300 | PO | 0.5% MC | Compound W | 4 | 3.69 | 3.76 | 0.58 | 13.15 |

Monkey IV Study

Male cynomolgus monkeys (n=3 per dose group) were administered a single nominal IV bolus dose of 1 mg/kg of Compound W via a jugular vein cannula. Compound W was formulated in D5W (5% dextrose in water solution). Animals had free access to food and water before and after dosing.

Blood samples (approximately 0.25 mL each) were collected via a carotid artery catheter prior to dosing and at 0 (predose), 5 min, 10 min, 0.25, 0.5, 1, 2, 3, 4, 6, 8, 12, 24, 48 hours postdose. Each blood sample was collected into a tube that was kept on wet ice and contained potassium EDTA as the anticoagulant. Plasma was separated and stored at approximately –70° C. until analysis.

Plasma samples were analyzed using a liquid chromatography/tandem mass spectrometry (LC/MS/MS) method to determine the concentrations of Compound 23 and Compound W, with a lower limit of quantitation (LLOQ) of 1 to 20 ng/mL, depending on the sample dilution factor. Plasma concentration vs. time data were subjected to noncompartmental pharmacokinetic (PK) analysis. The results of this analysis are provided in Table 16.

300 mg/kg of Compound W by gavage. Compound W was formulated in either 0.5% MC (microcrystalline cellulose) or 20% Captisol, 1% HPMC-AS (hydroxypropyl methylcellulose acetyl succinate), 1% PVP (polyvinylpyrrolidone). Animals had free access to food and water before and after dosing. Blood samples (approximately 0.25 mL each) were collected via a carotid artery catheter prior to dosing and at 0 (predose), 0.25, 0.5, 1, 1.5, 2, 4, 6, 8, 12, 24 hours post dose. Each blood sample was collected into a tube that was kept on wet ice and contained potassium EDTA as the anticoagulant. Plasma was separated and stored at approximately –70° C. until analysis.

Plasma samples were analyzed using a liquid chromatography/tandem mass spectrometry (LC/MS/MS) method to determine the concentrations of Compound 23 and Compound W with a lower limit of quantitation (LLOQ) of 1 to 20 ng/mL, depending on the sample dilution factor. Plasma

TABLE 16

Pharmacokinetic Data from Monkey IV Study

| Dose (mg/kg) | Route | Formulation | Analyte | C0 (ug/ml) | AUC (ug * hr/ml) | AUCextrap (ug * hr/ml) | Cl (ml/min/kg) | t1/2 (hr) | Vss (L/kg) |
|---|---|---|---|---|---|---|---|---|---|
| 5 | IV | D5W | Compound 23 | 10.9 | 3.78 | 3.81 | 23.4 | 6.17 | 2.09 |
| 5 | IV | D5W | Compound W | 62.4 | 5.79 | 5.83 | 18.2 | 5.35 | 1.88 |

Rat Oral Study

Groups of male Sprague Dawley rats (n=3 per dose group) were administered single nominal oral doses of 3, 10, 30, concentration vs. time data was subjected to noncompartmental pharmacokinetic (PK) analysis. The results of this analysis are provided in Table 17.

TABLE 17

Pharmacokinetic Data from Rat Oral Study

| Drug (mg/kg) | Formualtion | Analyte | Cmax/C0 (ug/ml) | AUC (ug * hr/ml) | AUCextrap (ug * hr/ml) | Tmax (hr) | t1/2 (hr) |
|---|---|---|---|---|---|---|---|
| 3 | 0.5% MC | Compound 23 | 0.117 | 0.311 | 0.314 | 0.58 | 4.06 |
| 30 | 0.5% MC | Compound 23 | 2.9 | 22.5 | 22.6 | 1.7 | 2.6 |
| 100 | 0.5% MC | Compound 23 | 6.6 | 77.1 | 77.4 | 2.5 | 2.7 |

TABLE 17-continued

Pharmacokinetic Data from Rat Oral Study

| Drug (mg/kg) | Formualtion | Analyte | Cmax/C0 (ug/ml) | AUC (ug * hr/ml) | AUCextrap (ug * hr/ml) | Tmax (hr) | t1/2 (hr) |
|---|---|---|---|---|---|---|---|
| 300 | 0.5% MC | Compound 23 | 11.7 | 222.8 | 307.6 | — | 17.9 |
| 300 | 20% CAPT, 1% HPMC-AS, 1% PVP | Compound 23 | 16.2 | 294.6 | — | 5 | — |
| 3 | 0.5% MC | Compound W | — | — | — | — | — |
| 30 | 0.5% MC | Compound W | 0.022 | 0.178 | 0.058 | 3.3 | 3.1 |
| 100 | 0.5% MC | Compound W | 0.021 | 0.061 | 0.066 | 0.8 | 7.2 |
| 300 | 0.5% MC | Compound W | 2.33 | 0.324 | 0.464 | 1.2 | 11.3 |
| 300 | 20% CAPT, 1% HPMC-AS, 1% PVP | Compound W | 0.6 | 2.37 | 4.27 | 1.8 | — |

Rat IV Study

Groups of male Sprague Dawley rats (n=3 per dose group) were administered single nominal IV bolus doses of 1 and 5 mg/kg of Compound W via a jugular vein cannula. Compound W was formulated in D5W. Animals had free access to food and water before and after dosing. Blood samples (approximately 0.25 mL each) were collected via a carotid artery catheter prior to dosing and at 0 (predose), 5 min, 10 min, 0.25, 0.5, 1, 1.5, 2, 4, 6, 8, 12, 24 hours post dose. Each blood sample was collected into a tube that was kept on wet ice and contained potassium EDTA as the anticoagulant. Plasma was separated and stored at approximately −70° C. until analysis.

Plasma samples were analyzed using a liquid chromatography/tandem mass spectrometry (LC/MS/MS) method to determine the concentrations of Compound 23 and Compound W with a lower limit of quantitation (LLOQ) of 1 to 20 ng/mL, depending on the sample dilution factor. Plasma concentration vs. time data were subjected to noncompartmental pharmacokinetic (PK) analysis. The results of this analysis are provided in Table 18.

TABLE 18

Pharmacokinetic Data from Rat IV Study

| Dose (mg/kg) | Formualtion | Analyte | Cmax/C0 (ug/ml) | AUC (ug * hr/ml) | AUCextrap (ug * hr/ml) | t1/2 (hr) | Cl_obs (ml/min/kg) | Vss_obs (L/kg) |
|---|---|---|---|---|---|---|---|---|
| 1 | D5W | Compound 23 | 0.247 | 0.306 | 0.31 | 1.8 | 54.9 | 3.8 |
| 5 | D5W | Compound 23 | 1.2 | 3.04 | 3.06 | 3.6 | 27.3 | 4.08 |
| 1 | D5W | Compound W | 4.8 | 0.416 | 0.419 | 0.9 | 46.7 | 0.38 |
| 5 | D5W | Compound W | 9.03 | 1.11 | 1.12 | 7.2 | 84.6 | 5.8 |

Mouse Oral Study

Groups of female CD-1 mice (n=3 per dose group) were administered single nominal oral doses of 10, 30, 100 mg/kg of Compound W by gavage. Compound W was formulated in 0.5% MC. Animals had free access to food and water before and after dosing. Blood samples (approximately 0.025 mL each) were collected from the sub-mandibular vein prior to dosing and at 0 (predose), 0.25, 0.5, 1, 1.5, 2, 4, 6, 8, 12, 24 hours postdose. Each blood sample was collected into a tube that was kept on wet ice and contained potassium EDTA as the anticoagulant. Plasma was separated and stored at approximately −70° C. until analysis.

Plasma samples were analyzed using a liquid chromatography/tandem mass spectrometry (LC/MS/MS) method with a lower limit of quantitation (LLOQ) of 1 to 20 ng/mL, depending on the sample dilution factor. Plasma concentration vs. time data was subjected to noncompartmental pharmacokinetic (PK) analysis. The results of this analysis are provided in Table 19.

TABLE 19

Pharmacokinetic Data from Mouse Oral Study

| Dose (mg/kg) | Formulation | AUC (0-t) (µg*hr/mL) | Cmax (µg*hr/ml) | Tmax (hr) |
|---|---|---|---|---|
| 10 | 0.5% MC | 1.7 | 1.2 | 0.3 |
| 30 | 0.5% MC | 4.1 | 2.1 | 0.3 |
| 100 | 0.5% MC | 26.6 | 9.1 | 0.4 |

The studies described above, demonstrate that Compound W is converted in vivo into Compound 23 in at least rats, dogs and monkeys.

EXAMPLE 35

Enzymology Studies

The enzyme inhibition activities of selected compounds of this invention were determined in the experiments described below:

DNA Gyrase ATPase Assay

The ATP hydrolysis activity of S. aureus DNA gyrase was measured by coupling the production of ADP through pyruvate kinase/lactate dehydrogenase to the oxidation of NADH. This method has been described previously (Tamura and Gellert, 1990, J. Biol. Chem., 265, 21342).

ATPase assays were carried out at 30° C. in buffered solutions containing 100 mM TRIS pH 7.6, 1.5 mM $MgCl_2$, 150 µM KCl. The coupling system contains final concentrations of 2.5 mM phosphoenol pyruvate, 200 µM nicotinamide adenine dinucleotide (NADH), 1 mM DTT, 30 ug/ml pyruvate kinase, and 10 ug/ml lactate dehydrogenase. The enzyme (90 nM final concentration) and a DMSO solution (3% final concentration) of the selected compound were added. The reaction mixture was allowed to incubate for 10 minutes at 30° C. The reaction was initiated by the addition of ATP to a final concentration of 0.9 mM, and the rate of NADH disappearance was monitored at 340 nanometers over the course of 10 minutes. The $K_i$ and $IC_{50}$ values were determined from rate versus concentration profiles.

Selected compounds of the present invention were found to inhibit S. aureus DNA gyrase. Table 20 shows the inhibitory activity of these compounds in the S. aureus DNA gyrase inhibition assay.

TABLE 20

Inhibition of S. aureus DNA Gyrase

| Selected Compound | $K_i$ (nM) | $IC_{50}$ (nM) |
|---|---|---|
| Compound 23 | 9 | |
| Compound W | <9 | 54 |

DNA Topo IV ATPase Assay

The conversion of ATP to ADP by S. aureus TopoIV enzyme was coupled to the conversion of NADH to NAD+, and the progress of the reaction was measured by the change in absorbance at 340 nm. TopoIV (64 nM) was incubated with the selected compound (3% DMSO final) in buffer for 10 minutes at 30° C. The buffer consisted of 100 mM Tris 7.5, 1.5 mM $MgCl_2$, 200 mM K.Glutamate, 2.5 mM phosphoenol pyruvate, 0.2 mM NADH, 1 mM DTT, 5 µg/mL linearized DNA, 50 µg/mL BSA, 30 µg/mL pyruvate kinase, and 10 µg/mL lactate dehyrodgenase (LDH). The reaction was initiated with ATP, and rates were monitored continuously for 20 minutes at 30° C. on a Molecular Devices SpectraMAX plate reader. The inhibition constant, Ki, and the $IC_{50}$ were determined from plots of rate vs. concentration of selected compound fit to the Morrison Equation for tight binding inhibitors.

Selected compounds of the present invention were found to inhibit S. aureus DNA Topo IV. Table 21 shows the inhibitory activity of these compounds in the S. aureus DNA gyrase inhibition assay.

TABLE 21

Inhibition of S. aureus DNA Topo IV

| Selected Compound | $K_i$ (nM) | $IC_{50}$ (nM) |
|---|---|---|
| Compound 23 | 12 | |
| Compound W | 30 | 150 |

EXAMPLE 36

Aqueous Solubility Study

The aqueous solubilities of compound 23 and compound W were determined according to the following procedure.

Preparation of Samples. Aqueous samples of each compound were prepared as follows. Compounds were weighed (20-30 mg compound) in 4 ml clear vials prior to adding water (0.5 mL) and stirring by magnetic stirrer. 1.0N HCl was added to the suspension to adjust the pH to the desired range. After stirring for 96 hours at room temperature, the suspension was filtered through a 0.22 micron filter (Millipore, Ultrafree centrifugal filters, Durapore PVDF 0.22 µm, Cat# UFC30GVNB). The filtrate was collected and the pH measured with a pH meter. The filtrate containing compound W was diluted 10-fold to provide an appropriate concentration for HPLC analysis. The filtrate containing compound 23 did not require dilution.

Preparation of Standard Solutions. Standard solutions of each compound were prepared according to the following procedure. 1 to 2 mg of each compound was accurately weighed into a 10 mL volumetric flask and either water (for compound W) or 1:1 methanol:0.1N HCl (for compound 23) was added to completely dissolve the compounds. Sonication was performed for compound 23 to assist with the dissolution in 1:1 methanol:0.1N HCl. When all solids dissolved, additional solvent was added to adjust the volume of each solution to 10 ml. The resulting solutions were thoroughly mixed to give the standard solutions of each compound. Each standard solution was then diluted with solvent by 2-fold, 10-fold, and 100-fold.

Solubility Analysis. Aliquots of each sample and each standard solution were analyzed by HPLC analysis (Agilent 1100, injection volume 10 µL, wavelength 271 nm, column XTerra® Phenyl 5 µm, 4.6×50 mm, Part No. 186001144, mobile phase: A: 0.1% TFA in water 0.1% TFA in AcN). Each standard solution was injected three times, and each of the samples was injected twice. Standard curves were obtained by plotting the average of the peak area from the HPLC versus the concentrations of the standard solutions (with appropriate corrections of the weights of the standards based on total water content of the solid as determined by elemental analysis). The concentration of each sample was calculated from the peak area of the aqueous sample from the HPLC results and the slope and intercept of the standard curves. The solubility values listed in Table 22 below were derived from the product of the concentration of the sample and the dilution factor of the sample.

TABLE 22

Aqueous Solubility of Compounds 23 and W

| Compound | Solid form | pH | Solubility (mg/mL) |
|---|---|---|---|
| Compound 23 | crystalline | >3.0 | <0.001 |
| Compound W | crystalline | 4.39 | 0.25 |

EXAMPLE 37

In Vivo Metabolism Study 1N Hepatic and Liver S9 Cells

The conversion of Compound W to Compound 23 was studied in liver and intestinal S9 fractions from rats, dogs, monkeys and humans. Compound W was incubated at 0.1, 0.3, 1, 3, 10, 20, 40, 100, 200, 300 µM in liver S9 fractions and at 1, 3, 10, 20, 100, 300, 500, 1000 µM in intestinal S9 fractions. The incubations were done for 0, 5, 10, 15, 30, 45 or 60 minutes. The formation of Compound 23 was quantified by LC/MS-MS and data were fitted to the Michaelis Menten equation. The data in Table 23 below indicates that Compound W rapidly converts to Compound 23 in these hepatic and intestinal S9 fractions.

TABLE 23

Velocity of formation ($V_{MAX}$) of Compound 23 from Compound W in Liver and Intestinal S9

| | $V_{MAX}$ (liver) (pmoles/min/mg) | $V_{MAX}$ (intestine) (pmoles/min/mg) |
|---|---|---|
| Dog | 19.3 | 1162 |
| Monkey | 25.2 | 1974 |
| Rat | 45.5 | 958 |
| Human | 45.8 | ND* |

*ND: Parameters not determined, rate of formation did not saturate

EXAMPLE 38

Mouse *M. tuberculosis* (Erdman) Lung Infection Model

Animals: female Balb/c mice (5-7 weeks of age; 6/group) were obtained from Jackson Laboratories (Bar Harbor, Me.) and were housed and maintained in a biosefatey level 3 (BSL3) facility in accordance with the Guide to the Care and Use of Experimental Animals.

Bacterial Strain and Stocks

*M. tuberculosis* ATCC 35801 (strain Erdman) was obtained from the ATCC (Manassas, Va., USA). The organism was grown in 20 tubes of modified 7H10 broth (pH 6.6; 7H10 agar formulation with agar and malachite green omitted) with 10% OADC (oleic acid, albumin, dextrose, catalase) enrichment (BBL Microbiology Systems, Cockeysville, Md., USA) and 0.05% Tween 80 for 5-10 days on a rotary shaker at 37'C. The cultures were pooled and diluted to 100 Klett units [equivalent to $5 \times 10^7$ colony forming units (cfu)/mL] (Photoelectric Colorimeter; Manostat Corp., New York, N.Y., USA). The culture was aliquotted and frozen at $-70°$ C. On the day of infection, the culture was thawed and the final inoculum was determined. The final inoculum size was determined by diluting to $5 \times 10^{-2}$ and plating 0.1 mL, in triplicate, on 7H10 agar plates (BBL Microbiology Systems) supplemented with 10% OADC enrichment. The plates were incubated at 37'C in ambient air for 4 weeks.

Mouse *M. tuberculosis* (Erdman) Infection Model

For intranasal infection, groups of mice were anaesthetized by intramuscular delivery of a telazol (45 mg/kg)/xylazine (7.5 mg/kg) cocktail (Lederle Parenterals, Carolina, Puerto Rico and Bayer Corp., Shawnee Mission, Kans., USA, respectively) and subsequently infected intranasally with ~$10^2$ viable *M. tuberculosis* in a 20 μL volume. The timetable for the experiment was a follows: on study day 0, intranasal infection and then on study day 24, early controls were sacrificed for lung burden determination and treatment was started. 28 days post initiation of treatment (52 days post infection) all treated mice and late controls were sacrificed for lung burden determination.

For bacterial load determination mice were sacrificed by $CO_2$ asphyxiation. Right lungs were aseptically removed and ground in a sealed tissue homogenizer (IdeaWorks! Laboratory Devices, Syracuse, N.Y., USA). The number of viable organisms was determined by serial dilution and titration on 7H10 agar plates. Plates were incubated at 37° C. in ambient air for 4 weeks prior to counting.

TABLE 23a

Compound 23A Reduces *M. Tuberculosis* Burdens in the Mouse *M. Tuberculosis* 28 Day Lung Infection Model

| Treatment Group | Average Lung Burden (Log cfu/lungs) | Log Reduction vs. Early Control | Log Reduction vs. Late Control |
|---|---|---|---|
| Early Control | 4.98 | | |
| Late Control (10 mL/Kg Vehicle) | 5.20 | −0.22 | |
| 10 mg/kg BID Compound 23A | 5.08 | −0.10 | 0.13 |
| 30 mg/kg BID Compound 23A | 4.11 | 0.86 | 1.09 |
| 100 mg/kg BID Compound 23A | 3.22 | 1.76 | 1.98 |
| 100 mg/kg QD Moxifloxacin | 2.94 | 2.04 | 2.26 |

Balb/c mice (6/group) were challenged IN (intranasally) with *M. tuberculosis* (Erdman; ATCC) at $1 \times 10^2$ cfu/mouse. After 24 days, a single group of mice (Early Control (EC)) was euthanized and the lungs harvested, homogenized and plated to quantitate *M. tuberculosis* burdens. The additional groups of infected mice were treated via oral gavage with Vehicle at 10 ml/kg (10% VitE-TPGS; Late Control, LC) or with Compound 23A administered at 10, 30, or 100 mg/kg BID for 28 days. An additional control group was treated with Moxifloxacin administered at 100 mg/kg QD. After 28 days of treatment, the groups were euthanized and the lungs harvested, homogenized and plated to quantitate *M. tuberculosis* burdens. Burdens from the right lung for each mouse and the median for each group of mice were recorded and summarized above in Table 23a.

Results: In summary and as shown above in Table 23a, twice daily oral dosing of Compound 23A exhibited in vivo efficacy against an experimentally induced lung *M. tuberculosis* infection in Balb/c mice. 28 days of treatment with compound 23A at 30 or 100 mg/kg provided reductions in lung burden vs early controls. In addition, Moxifloxacin provided lung burden reduction compared to vehicle treated controls. Compound 23A demonstrated dose-dependent reductions of 0.13, 1.09 and 1.98 log reductions versus vehicle control (Late) when administered at 10, 30, and 100 mg/kg. In addition, doses of 30 and 100 mg/kg of Compound 23A reduced bacterial burdens versus the early control by 0.7-1.5 logs suggesting Compound 23A has bactericidal activity. The potent anti-tuberculosis drug Moxifloxacin at 100 mg/kg QD provided lung burden reduction versus the early and late controls as previously published. The reductions were similar to those provided by Compound 23A administered at 100 mg/kg indicating that compound 23A has bactericidal activity against *M. tuberculosis*.

TABLE 23b

Compound W Reduces *M. Tuberculosis* Burdens in the Mouse *M. Tuberculosis* 28 Day Lung Infection Model

| Treatment Group | Median Lung Burden (Log cfu/lungs) | Log Reduction vs. Early Control | Log Reduction vs. Late Control |
|---|---|---|---|
| Early Control | 4.98 | | |
| Late Control | 4.36 | 0.62 | |
| 10 mg/kg BID Compound W | 4.34 | 0.64 | 0.02 |

TABLE 23b-continued

Compound W Reduces *M. Tuberculosis* Burdens in the Mouse *M. Tuberculosis* 28 Day Lung Infection Model

| Treatment Group | Median Lung Burden (Log cfu/lungs) | Log Reduction vs. Early Control | Log Reduction vs. Late Control |
| --- | --- | --- | --- |
| 30 mg/kg BID Compound W | 3.00 | 1.98 | 1.36 |
| 100 mg/kg BID Compound W | 2.35 | 2.63 | 2.01 |
| 100 mg/kg QD Moxifloxacin | 2.94 | 2.04 | 1.42 |

Balb/c mice (6/group) were challenged IN (intranasally) with *M. tuberculosis* (Erdman; ATCC) at $1 \times 10^2$ cfu/mouse. After 24 days, a single group of mice (Early Control (EC)) was euthanized and the lungs harvested, homogenized and plated to quantitate *M. tuberculosis* burdens. The additional groups of infected mice were treated via oral gavage with Vehicle at 10 ml/kg (10% VitE-TPGS; Late Control, LC) or with Compound W administered at 10, 30, or 100 mg/kg BID for 28 days. An additional control group was treated with Moxifloxacin administered at 100 mg/kg QD. After 28 days of treatment the groups were euthanized and the lungs harvested, homogenized and plated to quantitate *M. tuberculosis* burdens. Burdens from the right lung for each mouse and the median for each group of mice were recorded and summarized above in Table 23b.

Results: In summary, and as shown above in Table 23b, Compound W exhibited robust in vivo efficacy against an experimentally induced *M. tuberculosis* lung infection in Balb/c mice. After 28 days of treatments at 30 and 100 mg/kg BID there were decreases in bacterial density compared to early and time-matched vehicle controls. Compound W demonstrated dose-dependent reductions of 0.2, 1.36 and 2.02 log reductions versus vehicle control when administered at 10, 30 and 100 mg/kg. In addition, doses of 10, 30, and 100 mg/kg BID of Compound W reduced bacterial burdens versus the early control by 0.64-2.63 logs suggesting Compound W has bactericidal activity against *M. tuberculosis*. The potent anti-tuberculosis drug Moxifloxacin, at 100 mg/kg QD, provided lung burden reduction versus the early and late controls as previously published. The reductions were less than those provided by Compound W administered at 100 mg/kg and similar to those at 30 mg/kg BID Compound W indicating that compound W exhibits anti-tuberculosis activity on par or better than Moxifloxacin in this assay.

EXAMPLE 39

In Vitro Drug Combination Studies

To evaluate additional potential 2-drug combinations, these are compared first in an in vitro checkerboard experiments performed either in complete 7H9 broth or in whole blood inoculated with *M. tuberculosis* H37Rv in log phase growth. Concentrations of 0, 0.25×MIC, MIC, 4×MIC and (if clinically relevant) 16×MIC are tested for each compound. Pyrazinamide combinations may also be examined at pH 6.0, where its MIC is 50 µg/ml. For combinations with promising results, a similar checkerboard may be performed against nutrient-starved *M. tuberculosis* in PBS, to gain insight into the combination's activity against non-replicating organisms. Duplicate wells will be used for each concentration pair. Activity will be assessed by quantitative CFU counts performed after 0 and 7 days of incubation. Samples will be washed with PBS prior to plating.

EXAMPLE 40

In Vitro Drug Combination Studies Using the Whole Blood Assay

The activity of selected 2-drug combinations against intracellular bacilli is also compared in a whole blood culture assay in which blood from healthy volunteers is inoculated with an aliquot of *M. tuberculosis* and increasing concentrations of drug in a checkerboard fashion similar to that described above. Drug concentrations of 0, 0.25×MIC, MIC, 4×MIC and (if clinically relevant) 16×MIC is tested for each drug. Viable CFU counts are estimated after 0 and 3 days of incubation by washing the cells, osmotically lysing them, inoculating the lysate into MGIT liquid culture bottles and incubating on the cultures on the MGIT system, where the time-to-positivity results are applied to a standard curve to estimate the change in log CFU for treatment groups compared to pre-treatment and drug-free controls.

EXAMPLE 41

In Vitro Drug Combination Studies Using the Hollow Fiber Cartridge System

The hollow fiber cartridge system (HFS) is purchased from FiberCell (Frederick, Md.) and is used for the measurement of bactericidal and sterilizing activity for drug combinations. The peripheral compartments of HFS is inoculated with 7.5 log 10 CFU of *M. tuberculosis* in log-phase growth and is incubated at 37° C. under 5% CO2. The peripheral compartment of each HFS is sampled on days 0, 7, 14, 21, and 28 and samples are washed twice with normal saline to remove any drug carryover. The bacterial cultures are inoculated on Middlebrook 7H10 agar supplemented with 10% OADC to enumerate the total bacillary population as well as on agar supplemented with either drug or experimental compound to determine the resistant subpopulations.

Drugs and experimental compounds are administered to the central compartment of each HFS via a computer-controlled syringe pump. For pharmacokinetic matching, drugs and experimental compounds are administered at the same time to achieve a peak concentration of both isoniazid and rifampin at 1 h. The central compartments of the HFSs are sampled 12 times during the first 48 h and drug and experimental compound concentrations are then measured.

The results of the bactericidal-effect experiments are useful in the design of experiments for measuring sterilizing effect. Pharmacokinetic and statistical analysis uses the ADAPT 5 program, which has the maximum-likelihood solution via the expectation maximization algorithm. A one-compartment model with first-order input and elimination is utilized and a two-way analysis of variance (ANOVA) with Bonferroni posttest correction is used to compare bacterial burden from triplicate HFSs at each time point in GraphPad Prism version 5.00 (GraphPad Software, CA).

EXAMPLE 42

In vivo Mouse *M. tuberculosis* (Erdman) Lung Infection Model

Animals: female BALB/c mice (5-7 weeks of age; 6/group), are obtained from Jackson Laboratories, (Bar Harbor, Me.) and are housed and maintained in a BSL3 facility in accordance with the Guide to the Care and Use of Experimental Animals.

Bacterial strain and stocks

*M. tuberculosis* ATCC 35801 (strain Erdman) is obtained from the ATCC (Manassas, Va., USA). The organism is grown in 20 tubes of modified 7H10 broth (pH 6.6; 7H10 agar formulation with agar and malachite green omitted) with 10% OADC (oleic acid, albumin, dextrose, catalase) enrichment (BBL Microbiology Systems, Cockeysville, Md., USA) and 0.05% Tween 80 for 5-10 days on a rotary shaker at 37'C. The cultures are pooled and diluted to 100 Klett units [equivalent to $5\times10^7$ colony forming units (cfu)/mL] (Photoelectric Colorimeter; Manostat Corp., New York, N.Y., USA). The culture is aliquotted and frozen at −70'C. On the day of infection, the culture is thawed and the final inoculum is determined. The final inoculum size is determined by diluting to $5\times10^{-2}$ and plating 0.1 mL, in triplicate, on 7H10 agar plates (BBL Microbiology Systems) supplemented with 10% OADC enrichment. The plates are incubated at 37'C in ambient air for 4 weeks.

Mouse *M. tuberculosis* (Erdman) Infection Model

Intranasal infection groups of mice are anaesthetized by intramuscular delivery of a telazol (45 mg/kg)/xylazine (7.5 mg/kg) cocktail (Lederle Parenterals, Carolina, Puerto Rico and Bayer Corp., Shawnee Mission, Kans., USA, respectively) and subsequently infected intranasally with ~$10^2$ viable *M. tuberculosis* in a 20 μL volume. The timetable for the experiment is as follows: day 0, intranasal infection; on study day 24 early controls are sacrificed for lung burden determination and treatment is started. 28 days post initiation of treatment 52 days post infection, all treated mice and late controls are sacrificed for lung burden determination.

For bacterial load determination mice are sacrificed by $CO_2$ asphyxiation. Right lungs are aseptically removed and ground in a sealed tissue homogenizer (IdeaWorks! Laboratory Devices, Syracuse, N.Y., USA). The number of viable organisms is determined by serial dilution and titration on 7H10 agar plates. Plates are incubated at 37° C. in ambient air for 4 weeks prior to counting.

Groups for three compound combination studies:

Early Controls

Late Controls

TMC-207 25 mg/kg+pyrazinamide 150 mg/kg+Rifapentine 10 mg/kg

TMC-207 25 mg/kg+Compound (IB) where X is $PO(OH)_2$ 100 mg/kg+pyrazinamide 150 mg/kg TMC-207 25 mg/kg+Moxifloxacin 100 mg/kg+pyrazinamide 150 mg/kg Compound (IB) where X is $PO(OH)_2$ 100 mg/kg+Rifapentine 10 mg/kg+pyrazinamide 150 mg/kg Moxifloxacin 100 mg/kg+Rifapentine 10 mg/kg+pyrazinamide 150 mg/kg Compound (IB) where X is $PO(OH)_2$100 mg/kg+linezolid 100 mg/kg+pyrazinamide 150 mg/kg Compound (IB) where X is $PO(OH)_2$100 mg/kg+clofazimine 20 mg/kg+pyrazinamide 150 mg/kg Compound (IB) where X is $PO(OH)_2$ 100 mg/kg+Moxifloxacin 100 mg/kg+pyrazinamide 150 mg/kg Formulation Preparation:

Group #3: TMC-207 is formulated in 20% Hydroxypropyl-B-Cyclodextrin and treatment occurs in the morning. In the afternoon, (minimum of 2 hrs between dosing) all other compounds are combined for the groups of mice in one tube and dissolve by first adding 50% polyethylene glycol until dissolved and then adding 50% $ddH_2O$.

BALB/c mice (6/group) are challenged IN with *M. tuberculosis* (Erdman; ATCC) at a dose of $1\times10^2$ cfu/mouse. After 24 days a single group of mice (Early Control (EC)) is euthanized and the lungs harvested, homogenized and plated to quantify *M. tuberculosis* burdens. Compounds are administered at 10, 30, or 100 mg/kg BID for 28 days. After 28 days of treatment the groups are euthanized and the lungs harvested, homogenized and plated to quantify *M. tuberculosis* burdens.

REFERENCES

Combinations of antibiotics and nonantibiotic drugs enhance antimicrobial efficacy. Ejim L, Farha M A, Falconer S B, Wildenhain J, Coombes B K, Tyers M, Brown E D, Wright G D. Nat Chem. Biol. 2011 June; 7(6):348-50.

Selection of a moxifloxacin dose that suppresses drug resistance in *Mycobacterium tuberculosis*, by use of an in vitro pharmacodynamic infection model and mathematical modeling. Gumbo T, Louie A, Deziel M R, Parsons L M, Salfinger M, Drusano G L. J Infect Dis. 2004 Nov. 1; 190(9):1642-51.

Pharmacokinetics and whole-blood bactericidal activity against *Mycobacterium tuberculosis* of single doses of PNU-100480 in healthy volunteers. Wallis R S, Jakubiec W M, Kumar V, Silvia A M, Paige D, Dimitrova D, Li X, Ladutko L, Campbell S, Friedland G, Mitton-Fry M, Miller P F. J Infect Dis. 2010 Sep. 1; 202(5): 745-51.

EXAMPLE 43

Evaluation of the Anti-Tuberculosis Activity of Compounds in Mice

PHASE 1—Evaluation of Compounds as Monotherapy Against Established TB in Mice

Methods

The experimental scheme is presented in Table 24. BALB/c mice will be infected with ~100 CFU of virulent *M. tuberculosis* H37Rv in order to produce a stable infection with *M. tuberculosis* of ~$10^6$ organisms in the lung at the initiation of treatment 5 weeks later (D0). Drugs will be prepared in an appropriate vehicle. Treatment will be administered daily, 5 days per week, by esophageal gavage unless subcutaneous injection is required. Outcomes will be lung CFU counts after 4 weeks of treatment. Quantitative cultures of lung samples will be performed in duplicate on OADC-enriched 7H11 agar medium. Group mean differences in lung CFU counts will be compared using one-way ANOVA with Dunnett's post-test (GraphPad Prism 4) to adjust for multiple comparisons.

Explanation of Treatment Groups

Untreated: This is the negative control group. Five mice will be sacrificed the day after *M. tuberculosis* infection (D-34) and on the day of treatment initiation (D0) to determine the number of bacilli implanted and the extent of multiplication from D-35 to D0, respectively. Additional mice will be sacrificed 4 weeks for microbiological characterization of the natural history of infection.

Isoniazid (INH): mice in this control group will receive this first-line drug known for its strong bactericidal activity against actively multiplying organisms but reduced activity against non-actively multiplying organisms.

Rifampin (RIF): mice in this control group will receive this first-line drug known for its strong bactericidal activity against non-actively multiplying organisms.

Test compound A (A): mice in this group will receive a first compound of formula (I) ("A") at one of 3 doses.

Test compound B (B): mice in this group will receive a second compound of formula (I) ("B") at one of 3 doses.

TABLE 24

Experimental scheme for dose-ranging activity study

| Regimen [dose(mg/kg)] | No of mice killed by time point | | | |
|---|---|---|---|---|
| | D-35 | D0 | Wk 4 | Total |
| Untreated | 5 | 5 | 5 | 15 |
| INH (10) | | | 5 | 5 |
| RIF (10) | | | 5 | 5 |
| A (10) | | | 5 | 5 |
| A (30) | | | 5 | 5 |
| A (100) | | | 5 | 5 |
| B (10) | | | 5 | 5 |
| B (30) | | | 5 | 5 |
| B (100) | | | 5 | 5 |
| Total | 5 | 5 | 45 | 55 |

The experiment will also include a PK study to determine the 24-hour serum and lung PK profile for each test compound and dose in infected mice during the 2nd week of treatment. Mice will be sacrificed according to the scheme in Table 25, around the dose administered on Wednesday or Thursday during the 2nd week of treatment. Three mice will be sacrificed for each drug and dose at the indicated time points before and after drug administration. At the time of sacrifice, mice will be anesthetized with isoflurane, using the drop method, and exsanguinated by cardiac puncture. Serum will be harvested and frozen at −80° C. The right lung will be harvested, homogenized thoroughly and frozen at −80° C.

TABLE 25

Scheme for serum and lung PK sub-study
No of mice killed by time point

| 0 h | 0.5 h | 1 h | 2 h | 4 h | 8 h | Total |
|---|---|---|---|---|---|---|
| 3 | 3 | 3 | 3 | 3 | 3 | 18 |

To perform serum and lung PK for all 3 doses of both drugs, a total of 108 mice will be required.

PHASE 2—Evaluation of Compound Activity in Combination with Existing TB Drugs

1) Experiment to identify the best companion drugs for the test compounds

The interaction of Compounds A and/or B with existing TB drugs will be evaluated first in 2 in vitro models to inform the design of long-term combination therapy studies with 3- and/or 4-drug combinations that utilize relapse rate as the measure for stable cure and thereby promote the most efficient use of limited resources.

Methods

In Vitro Checkerboard Assay

Potential 2-drug combinations will be compared first in in vitro checkerboard experiments performed either in complete 7H9 broth or in whole blood inoculated with *M. tuberculosis* H37Rv in log phase growth. Drug concentrations of 0, 0.25×MIC, MIC, 4×MIC and (if clinically relevant) 16×MIC will be tested for each drug. PZA will be evaluated at normal pH, where its MIC against *M. tuberculosis* H37Rv is 250 μg/ml. It may also be examined at pH 6.0, where its MIC is 50 μg/ml. For combinations with promising results, a similar checkerboard may be performed against nutrient-starved *M. tuberculosis* in PBS, to gain insight into the combination's activity against non-replicating organisms.

A sample experimental scheme for a checkerboard experiment is presented in Table 26. Duplicate wells will be used for each concentration pair. Activity will be assessed by quantitative CFU counts performed after 0 and 7 days of incubation. Samples will be washed with PBS prior to plating.

In Vitro Whole Blood Assay

Activity of selected 2-drug combinations against intracellular bacilli will be compared in a whole blood culture assay in which blood from healthy volunteers is inoculated with an aliquot of *M. tuberculosis* and increasing concentrations of drug in a checkerboard fashion similar to that described above. Drug concentrations of 0, 0.25×MIC, MIC, 4×MIC and (if clinically relevant) 16×MIC will be tested for each drug, as depicted in Table 26. Viable CFU counts are estimated after 0 and 3 days of incubation by washing the cells, osmotically lysing them, inoculating the lysate into MGIT liquid culture bottles and incubating on the cultures on the MGIT system, where the time-to-positivity results are applied to a standard curve to estimate the change in log CFU for treatment groups compared to pre-treatment and drug-free controls.

Rationale for Drugs to be Tested

Isoniazid (INH): first-line drug known for its strong bactericidal activity against actively multiplying organisms but reduced activity against non-actively multiplying organisms.

Rifampin (RIF): first-line drug known for its moderate activity against actively multiplying organisms, but strong bactericidal activity against non-actively multiplying organisms (sterilizing activity).

Pyrazinamide (PZA): first-line drug known for having pH-dependent activity against *M. tuberculosis* in vitro, but significant sterilizing activity in mice, presumably against *M. tuberculosis* inside activated macrophages.

Moxifloxacin (MXF): key second-line drug known for its strong bactericidal activity against actively multiplying organisms but reduced activity against non-actively multiplying organisms. MXF is being studied in clinical trials to evaluate whether it belongs as a first-line TB drug.

Linezolid (LZD): second-line drug commonly used in salvage therapy for recalcitrant drug-resistant TB. LZD may also serve as a surrogate for new oxazolidinones in clinical development.

Cmpd A (A): Test compound A.

Cmpd B (B): Test compound B.

TABLE 26

Sample scheme for checkerboard experiment

| Conc of Drug 2 | Concentration of Drug 1 | | | | |
|---|---|---|---|---|---|
| | 0 | 0.25× MIC | MIC | 4× MIC | 16× MIC |
| 0 | | | | | |
| 0.25× MIC | | | | | |
| MIC | | | | | |
| 4× MIC | | | | | |
| 16× MIC | | | | | |

2) Experiment to evaluate the sterilizing activity of novel combinations including test compounds of formula (I).

At present, the gold standard for measuring a regimen's sterilizing activity in the mouse model is the assessment of relapse after discontinuation of therapy. With available regimens as standard comparators, such experiments require 7-10 months to complete due to the requirement for a treatment-free follow-up period of ≥3 months to determine the proportion of mice with culture-positive relapse. Because of the time- and cost-consuming nature of such experiments, it is imperative to utilize the most efficient study designs possible. By establishing the relative activity of various 2-drug building blocks in the short-term infection model as described above, the most promising regimens can be carried forward into 1 or 2 relapse-based studies to compare the activity of such regimens to that of the standard first-line regimen and/or that of more potent experimental regimens.

A sample experimental scheme is presented in Table 27. In this example, the effect of adding test compound A to the first-line regimen or substituting it for INH is examined, as is the substitution of test compound B for ethambutol or amikacin in an idealized second-line regimen comprised of existing drugs. In each case, the regimens in question are truncated after treatment of reduced duration in order to demonstrate whether the incorporation of test compound could have a treatment-shortening effect. The primary endpoint is the proportion of mice with positive cultures (i.e., relapse) 3 months after the discontinuation of therapy. Mice will be infected by the aerosol route with approximately 4 $\log_{10}$ CFU on Day −14. The infection will incubate for 14 days before mice are randomized into treatment groups as indicated and treatment is begun. The indicated regimens will be administered as described above. Group mean lung CFU counts will be compared by one-way ANOVA with Bonferroni's post-test to adjust for multiple comparisons. Additional cohorts of 15 mice will be held for 3 months after completing various durations of treatment before being sacrificed for relapse determination. The entire lung homogenate will be plated on 7H11 agar. The proportions of mice with culture-positive relapse will be compared using Fisher's Exact test with adjustment for multiple corrections.

TABLE 27

Example of an experimental scheme to assess the sterilizing activity of promising regimens containing test compounds
Time point and No. of mice to sacrifice**

| Regimen* | D-13 | D0 | M2 | M4 (+3) | M5 (+3) | M6 (+3) | Total |
|---|---|---|---|---|---|---|---|
| 2RHZ/3RH | 6 | 6 | 5 | 5(15) | 5(15) | | 57 |
| 2RHZA/3RHA | | | 5 | 5(15) | 5(15) | | 45 |
| 2RAZ/3RA | | | 5 | 5(15) | 5(15) | | 45 |
| 2MEZAmk/4ME | | | 5 | 5 | 5(15) | 5(15) | 50 |
| 2MBZAmk/4MB | | | 5 | 5 | 5(15) | 5(15) | 50 |
| 2MEZB/4MEB | | | 5 | 5 | 5(15) | 5(15) | 50 |
| Total | 6 | 6 | 30 | 30(45) | 30(90) | 15(45) | 297 |

*R, RIF 10 mg/kg; H, INH 10 mg/kg; Z, PZA 150 mg/kg; A, Test compound A; B, Test compound B; M, MXF 100 mg/kg; E, ethambutol 100 mg/kg; Amk, amikacin 30 mg/kg
**Time points are shown in days (D) (day-13 [D-13] pr day 0 [D0]) or monthls (M) (eg., 2 months = M2) of treatment. (+3) indicates that the mice are held for 3 months after the completion of treatment at the indicated time point.
Explanation of treatment groups
2RHZ/3RH: first-line regimen control consisting of 2 months of RIF, INH, and PZA, followed by 3 months of RIF and INH.
2RHZA/3RHA: test regimen in which test compound A is added to the first-line regimen.
2RAZE/3RA: test regimen in which test compound A is substituted for INH in the first-line regimen.
2MEZAmk/4ME: second-line regimen control consisting of 2 months of MXF, ethambutol, PZA and amikacin, followed by 4 months of MXF and ethambutol.
2MBZAmk/4MB: test regimen in which test compound B is substituted for ethambutol in the second-line regimen.
2MEZAmk/4MEB: test regimen in which test compound B is substituted for amikacin in the second-line regimen.

EXAMPLE 44

Minimal Inhibitory Concentration (MIC) of Compound 23A in *M. tuberculosis* ("Mtb") Bacterial Broth Culture Against Diverse Mtb Isolates and Various Species of *Mycobacteria*

To determine the MIC of Compound 23A, 96-well microtiter plates were used (Corning #3904) to culture *M. tuberculosis* in Middlebrook 7H9 broth (BD271310) containing ADC enrichment, while agar plates were used to sub-culture various isolates of Mtb streaked to single colonies. Cell suspensions were made containing ~$10^8$ cells/ml following sonication and then diluted 1/200 by transferring 0.2 ml of cells to 40 ml sterile 7H9 broth with ADC supplement (a final concentration of ~$10^6$ cells/ml). 100 μl of Mtb cells were then (~$5\times10^4$ cells) added each microtiter well containing 1 μl of test compounds in DMSO (see below). Microtiter plates were incubated in a humidified 37° C. chamber for 9 days and bacterial growth was measured by either visual inspection or by adding 30 μl of 0.01% sterile resazurin to each well and measuring the background fluorescence at an Excitation of 492 nm/emission of 595 nm after 24 hours. The minimum inhibitory concentrations (MICs) were defined as the lowest concentration of an antimicrobial that inhibits the growth of bacteria by ≥70%.

TABLE 28

MICs of Compound 23A and Moxifloxacin (as a comparator) in an expanded set of *Mycobacterium tuberculosis* (Mtb) strains

| Organism | 23A | Moxifloxacin |
|---|---|---|
| Mtb H37Rv | 0.015, 0.015 | 0.03, 0.03 |
| Mtb Erdman | 0.06, 0.06 | 0.03, 0.03 |
| Mtb CDC1551 | 0.015, 0.015 | 0.015, 0.015 |
| Mtb HN878 (Beijing-Type) | 0.015, 0.015 | 0.03, 0.015 |
| Mtb GN9 | 0.03, 0.03 | 0.03, 0.015 |
| *M. avium* 103 | 0.12, 0.23 | NT |
| *M. avium* Far | 0.23, 0.23 | NT |
| *M. avium* 3404.4 | 0.23, 0.23 | NT |
| *M. kansasii* 303 | 0.03, 0.03 | 0.03, 0.03 |
| *M. kansasii* 316 | 0.06, 0.06 | 0.03, 0.03 |
| *M. kansasii* 379 | <0.015, <0.015 | 0.03, 0.03 |
| *M. smegmatis* | 6.25 | NT |

Conclusion: Compound 23A is potently active against a diverse range of Mtb species.

TABLE 29

MICs (ug/ml) of Compound 23A in Drug Resistant *Mycobacteria* in Broth Culture (again using Moxifloxacin as comparator)

| Organism | Cmpd 23A | Moxifloxacin |
|---|---|---|
| *M. tuberculosis* Erdman | 0.125, 0.06 | 0.03, 0.015 |
| *M. tuberculosis* $Levo^R$ 2D | 0.015, 0.015 | 2, 2 |
| *M. tuberculosis* $Levo/Gat^R$ 2C | 0.06, 0.06 | 8, 8 |
| *M. tuberculosis* 5 | 0.125, 0.125 | 8, 4 |

*M. tuberculosis* $Levo^R$ 2D and *M. tuberculosis* $Levo/Gat^R$ 2C are laboratory derived resistant strains of *M. tuberculosis* Erdman; they are single-drug resistant strains. *M. tuberculosis* 5 is an XDR strain
Conclusion: Compound 23A is also active against drug resistant Mtb

EXAMPLE 45

MIC Determination in the Low-Oxygen-Recovery Assay (LORA) for Nonreplicating *M. tuberculosis*

Screening for new antimicrobial agents is routinely conducted only against actively replicating bacteria. However, it is now widely accepted that a physiological state of non-replicating persistence (NRP) is responsible for antimicrobial tolerance in many bacterial infections. In tuberculosis, the key to shortening the 6-month regimen lies in targeting this NRP subpopulation. Therefore, Compound 23A was tested in a high-throughput, luminescence-based low oxygen-recovery assay (LORA), developed to screen antimicrobial agents against NRP *Mycobacterium tuberculosis* as described by Cho et al 2007. Cho S H, Warit S, Wan B, Hwang C H, Pauli G F, Franzblau S G; "Low-Oxygen-Recovery Assay for High-Throughput Screening of Compounds against Nonreplicating *Mycobacterium tuberculosis*" Antimicrob Agents Chemother. 2007 April; 51(4): 1380-1385 doi: 10.1128/AAC.00055-06.

Results:

The LORA MIC for Compound 23A was 0.25 ug/mL, indicating that the test compound retained activity against non-replicating, persistent *Mycobacterium tuberculosis*. In contrast Moxiflxacin was inactive (MIC>40 ug/ml) and gatifloxacin was 10-fold less active (MIC=3.6 ug/ml)

EXAMPLE 46

Efficacy Against Intracellular *M. tuberculosis*

Cultures of recombinant *M. tuberculosis* (Mtb) expressing luciferase were maintained in 7H9 broth supplemented with 0.05% Tween 80, 10% ADC, and 20 ug/ml kanamycin, (25 ml in a filter-cap 125 ml plastic Erlenmeyer flask), at 37° C. with static incubation. Immediately prior to infection of macrophages or cell lines, the Mtb cultures were sonicated in suspension for 10 seconds and diluted to a density of $8\times10^5$ cells/ml for a multiplicity of infection (MOI) of 2:1. Prior to *M. tuberculosis* infection, PMA-activated THP-1 or J774 cells were adjusted to a cell density of $2-3\times10^5$ cells/ml in 25 mM HEPES-buffered RPMI-1640 media (without phenol red; medium #2) supplemented with 10% FBS, L-glutamine, and 0.05 mM b-mercaptoethanol.

Test compounds were dispensed into sterile round bottom 96 well tissue culture plates at the desired concentration in 1 μl volumes of DMSO (0.5% DMSO final). Just prior to treatment of Mtb-infected cells with the compound, supernatant containing un-ingested Mtb from each well was removed and replaced with 100 μl fresh media. Cell cultures were incubated remaining plates at 37° C., 5% $CO_2$, in humidified chamber and the endpoint luciferase of all test and control plates was determined 5 days (120 hours) after infection by adding 100 ul of Bright Glow reagent to each well, incubating for 10 minutes at room temperature, covering with adhesive top seal and reading the luminescence in Tecan Spectrafluor+, at a gain of 150 at maximum integration time. $IC_{50}$ was defined the concentration of an antimicrobial that inhibited the growth of intracellular bacteria by 50%

Results: The effects of Compound 23A on intracellular replication on Mtb were examined in two different cell types (THP-1 and J774) and three different Mtb strains (Erdman, H37Ra and CDC1551). Three other gyrase-target antibiotics were used as controls. Compound 23A was efficacious against all three intracellular Mtb strains in both cell types.

TABLE 30

| Mtb Strain/Cell type | 23A | Moxifloxacin | Gatifloxacin | Novobiocin |
|---|---|---|---|---|
| Erdman (MIC) | 0.06 | 0.03 | 0.25 | 61.00 |
| Mtb H37Ra in THP1 Cells ($IC_{50}$) | 0.03 | 0.33 | 0.20 | 2.10 |

TABLE 30-continued

| Mtb Strain/Cell type | 23A | Moxifloxacin | Gatifloxacin | Novobiocin |
|---|---|---|---|---|
| Mtb CDC1551 in J774 Cells ($IC_{50}$) | 0.12 | 0.21 | 0.94 | NT |
| Mtb H37Rv in J774 Cells ($IC_{50}$) | 0.21 | NT | NT | NT |
| Mtb Erdman in J774 Cells ($IC_{50}$) | <0.17 | NT | NT | NT |

TABLE 31

Comparison of Compound 23A vs. Standard TB Drugs in Culture and Intracellular Macrophage (THP1) Assay

| | MIC (μg/mL) | |
|---|---|---|
| Compound | Broth | Macrophage Cells |
| 23A | 0.01 | 0.03 |
| Isoniazid | 0.21 | 0.012 |
| Rifampin | 0.03 | 0.008 |
| Ethambutol | 2.55 | 1.26 |
| Pyrazinamide | >12.3 | >2.5 |
| Linezolid | 0.53 | 0.37 |
| Moxifloxacin | 0.12 | 0.33 |

Mtb H37Ra was used as the test strain. The data show that Compound 23A has at least equivalent potency as approved anti-TB agents.

EXAMPLE 47

Efficacy of Compound 23A in Combination with Approved TB Agents

A checkerboard approach was used to determine the effect of co-administration of Compound 23A with approved anti-TB agents, using both broth culture and Intracellular. In order to assess whether the effects were antagonistic, additive or synergistic the Fractional Inhibitory Concentration (FIC) Index was calculated as follows:

$$FIC_{index} = \frac{MIC_A \text{ with } B}{MIC_A} + \frac{MIC_B \text{ with } A}{MIC_B}$$

The combination is considered antagonistic if the $FIC_{index}$ is great then 4, indifferent or additive if the $FIC_{index}$ between 0.5 and 4, and synergistic if the index is less index is an than 0.5. The results are tabulated below and show that Compound 23A was generally additive to the effect of approved anti-TB agents and may be synergistic when used in combination with TMC207 and Clofazimine. None of the drug combinations used showed antagonistic effects.

TABLE 32

| Cmpd 23A | Mtb in Broth Culture | | Intracellular Mtb | |
|---|---|---|---|---|
| with | Additive | Synergy | Additive | Synergy |
| Isoniazid | 0.75 | | 0.75 | |
| Rifampin | 0.63 | | 2.00 | |
| Moxifloxacin | 1.00 | | 1.00 | |
| TMC-207 | 1.00 | | | 0.50 |
| Amikaicin | 2.00 | | 2.00 | |
| Linezolid* | | 0.50 | 2.00 | |
| PA-824 | 2.00 | | 1.00 | |
| Ethambutol | 0.63 | | 2.00 | |
| Clofazimine | 2.00 | | | 0.50 |

What is claimed is:

1. A method of controlling, treating or reducing the advancement, severity or effects of a mycobacterium disease comprising administering to a patient in need thereof a therapeutically effective amount of:

(a) a compound of formula

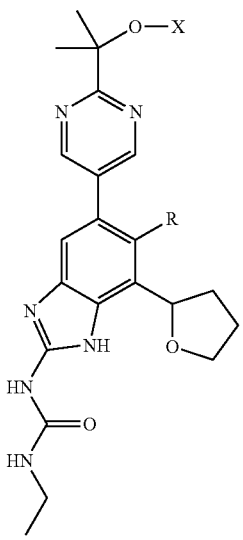

(I)

wherein R is hydrogen or fluorine; X is hydrogen, —PO(OH)2, —PO(OH)O⁻M⁺, —PO(O⁻)₂.2M⁺, or —PO(O⁻)₂.D²⁺; M⁺ is a pharmaceutically acceptable monovalent cation; and D²⁺ is a pharmaceutically acceptable divalent cation; or a pharmaceutically acceptable salt thereof; in combination with:

(b) one or more antibiotic compounds comprising a diarylquinolone, rifapentine, rifalazil, a nitroimidazole, a benzothiazinone, capreomycin, clofazimine, cycloserine, dapsone, a thiocarbamide, ethambutol, DC-159a, a nitrobenzthiazole, sutezolid (PNU-100480), AZD-5847, posizolid (AZD-2563), para-aminosalicylic acid, SQ-109, SQ-609, a capuramycin, a caprazene nucleoside, an isothiazoloquinolone, thioridazine, thiacetazone, dirithromycin, roxithromycin, telithromycin, azithromycin, clarithromycin, erythromycin, amikacin, kanamycin, streptomycin, levofloxacin, moxifloxacin, gatifloxacin, linezolid, rifalazil, meropenem, clavulanate, PA 824, pyrazinamide, TMC-207, oxazolidinine, nitroimidazole, or isoniazid, with the proviso that when the one or more antibiotic compounds is thioridazine, azithromycin, clarithromycin, erythromycin, amikacin, kanamycin, streptomycin, levofloxacin, moxifloxacin, gatifloxacin, linezolid, rifalazil, meropenem, clavulanate, or isoniazid, then an additional antibiotic is also present in the combination.

2. The method of claim 1, wherein said one or more antibiotic compounds comprises bedaquiline, rifapentine, moxifloxacin, linezolid, delaminid, or PA 824.

3. The method of claim 1, wherein said one or more antibiotic compounds comprises moxifloxacin, linezolid, rifalazil, meropenem, clavulanate, pyrazinamide, and isoniazid.

4. The method of claim 1 wherein at least one of the antibiotics is pyrazinamide.

5. The method of claim 1 wherein the compound of formula (I) is a compound of formula

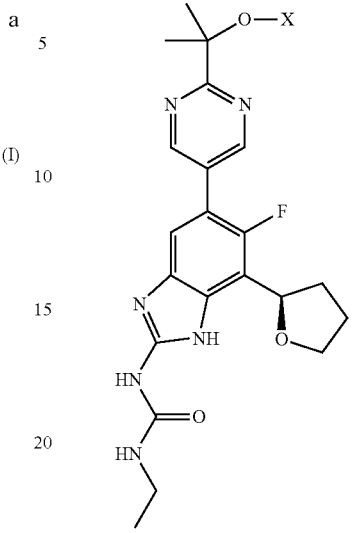

(IB)

wherein X is —PO(OH)₂, —PO(OH)O⁻M⁺, —PO(O⁻)₂.2M⁺, or —PO(O⁻)₂.D²⁺; M⁺ is a pharmaceutically acceptable monovalent cation; and D²⁺ is a pharmaceutically acceptable divalent cation; or a pharmaceutically acceptable salt thereof.

6. The method of claim 1 wherein the compound of formula (I) is a compound of formula

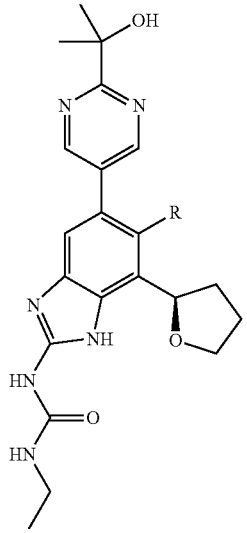

(IC)

wherein R is hydrogen or fluorine; or a pharmaceutically acceptable salt thereof.

7. The method of claim 1 wherein the compound of formula (I) is (R)-1-ethyl-3-(5-(2-(2-hydroxypropan-2-yl)pyrimidin-5-yl)-7-(tetrahydrofuran-2-yl)-1H-benzo[d]imidazol-2-yl)urea, or a pharmaceutically acceptable salt thereof.

8. The method of claim 1, wherein the compound of formula (I) is (R)-1-ethyl-3-(6-fluoro-5-(2-(2-hydroxypropan-2-yl)pyrimidin-5-yl)-7-(tetrahydrofuran-2-yl)-1H-benzo[d]imidazol-2-yl)urea, or a pharmaceutically acceptable salt thereof.

9. The method of claim 1, wherein the salt of formula (I) is a methanesulfonic acid salt of (R)-1-ethyl-3-(5-(2-(2-hydroxypropan-2-yl)pyrimidin-5-yl)-7-(tetrahydrofuran-2-yl)-1H-benzo[d]imidazol-2-yl)urea.

10. The method of claim 1, wherein the salt of formula (I) is a methanesulfonic acid salt of (R)-1-ethyl-3-(6-fluoro-5-(2-(2-hydroxypropan-2-yl)pyrimidin-5-yl)-7-(tetrahydrofuran-2-yl)-1H-benzo[d]imidazol-2-yl)urea.

11. The method according to claim 1, wherein the compound of formula (I) is disodium (R)-2-(5-(2-(3-ethylureido)-6-fluoro-7-(tetrahydrofuran-2-yl)-1H-benzo[d]imidazol-5-yl)pyrimidin-2-yl)propan-2-yl phosphate.

12. The method according to claim 1 wherein the mycobacterial disease is caused by *M. tuberculosis*, *M. avium* intracellulare, *M. ulcerans*, *M. kansasii*, *M. fortuitum*, *M. abcesses*, *M. leprae*, *M. africanum*, *M. marinum*, *M. avium* paratuberculosis, or *M. bovis*, *M. chelone*, *M. scrofulaceum*, *M. xenopi*, *M. intracellulare*, or *M. microti*.

13. A method according claim 1 wherein the compound of formula (I) is administered with only one antibiotic selected from rifapentine, TMC-207, SQ-109, a nitroimidazole, or an oxazolidinone.

14. A method according to claim 13 wherein the antibiotic is rifapentine.

15. A method according claim 13 further comprising administering pyrazinamide.

16. A method according to claim 13 wherein the compound of formula (I) is (R)-1-ethyl-3-(6-fluoro-5-(2-(2-hydroxypropan-2-yl)pyrimidin-5-yl)-7-(tetrahydrofuran-2-yl)-1H-benzo[d]imidazol-2-yl)urea, or a pharmaceutically acceptable salt thereof.

17. A method of treating tuberculosis comprising administering a therapeutically effective amount of:
(a) a compound of formula (I):

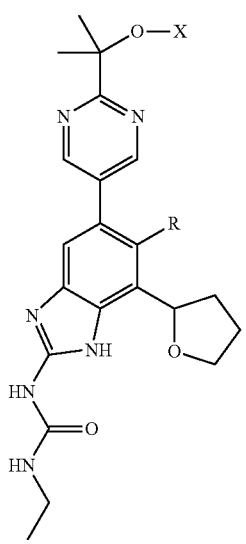

(I)

wherein R is hydrogen or fluorine; X is hydrogen, $-PO(OH)_2$, $-PO(OH)O^-M^+$, $-PO(O^-)_2.2M^+$, or $-PO(O^-)_2.D^{2+}$; $M^+$ is a pharmaceutically acceptable monovalent cation; and $D^{2+}$ is a pharmaceutically acceptable divalent cation; or a pharmaceutically acceptable salt thereof; in combination with:

(b) one or more antibiotic compounds comprising a diarylquinolone, rifapentine, rifalazil, a nitroimidazole, a benzothiazinone, capreomycin, clofazimine, cycloserine, dapsone, a thiocarbamide, ethambutol, DC-159a, a nitrobenzthiazole, sutezolid (PNU-100480), AZD-5847, posizolid (AZD-2563), para-aminosalicylic acid, SQ-109, SQ-609, a capuramycin, a caprazene nucleoside, an isothiazoloquinolone, thioridazine, moxifloxacin, gatifloxacin, linezolid, rifalazil, meropenem, clavulanate, or isoniazid, with the proviso that when the one or more antibiotic compounds is thioridazine, moxifloxacin, gatifloxacin, linezolid, rifalazil, meropenem, clavulanate, ad or isoniazid, then an additional antibiotic is also present in the combination.

18. The method of claim 1 wherein the one or more antibiotic compounds are TMC-207 and pyrazinamide.

19. The method of claim 1 wherein the one or more antibiotic compounds are rifapentine and pyrazinamide.

20. The method of claim 1 wherein the one or more antibiotic compounds are oxazolidinone and pyrazinamide.

21. The method of claim 1 wherein the one or more antibiotic compounds are nitroimidazole and pyrazinamide.

22. The method of claim 1 wherein the one or more antibiotic compounds are pyrazinamide and SQ-109.

23. The method of claim 1 wherein the one or more antibiotic compounds are TMC-207, SQ-109, and pyrazinamide.

24. The method of claim 1 wherein the one or more antibiotic compounds are SQ-109, clavulanate and meropenem.

25. The method of claim 1 wherein the one or more antibiotic compounds are rifapentine, SQ-109, and pyrazinamide.

26. The method of claim 1 wherein the one or more antibiotic compounds are oxazolidinone, SQ-109, and pyrazinamide.

27. The method of claim 1 wherein the one or more antibiotic compounds are nitroimidazole, SQ-109, and pyrazinamide.

28. The method of claim 1 wherein the one or more antibiotic compounds are clavulanate, meropenem, and SQ-109.

* * * * *